United States Patent
Zhou et al.

(10) Patent No.: US 11,840,517 B2
(45) Date of Patent: Dec. 12, 2023

(54) LAPPACONITINE DERIVATIVE WITH ANALGESIC ACTIVITY, AND PREPARATION AND APPLICATION THEREOF

(71) Applicant: Southwest Jiaotong University, Chengdu (CN)

(72) Inventors: Xianli Zhou, Chengdu (CN); Feng Gao, Chengdu (CN); Xiaohuan Li, Chengdu (CN); Yuzhu Li, Chengdu (CN); Shuai Huang, Chengdu (CN); Lin Chen, Chengdu (CN); Yinyong Zhang, Chengdu (CN)

(73) Assignee: Southwest Jiaotong University, Chengdu (CN)

( * ) Notice: Subject to any disclaimer, the term of this patent is extended or adjusted under 35 U.S.C. 154(b) by 0 days.

(21) Appl. No.: 17/581,920

(22) Filed: Jan. 22, 2022

(65) Prior Publication Data

US 2022/0144779 A1    May 12, 2022

(30) Foreign Application Priority Data

Apr. 19, 2021    (CN) .......................... 202110419203.4

(51) Int. Cl.
| | |
|---|---|
| *C07D 221/22* | (2006.01) |
| *C07D 401/12* | (2006.01) |
| *C07D 403/12* | (2006.01) |
| *C07D 405/12* | (2006.01) |
| *C07D 409/12* | (2006.01) |
| *A61P 29/00* | (2006.01) |
| *A61K 31/439* | (2006.01) |
| *A61K 31/4709* | (2006.01) |
| *C07D 223/32* | (2006.01) |

(52) U.S. Cl.
CPC .................. *C07D 223/32* (2013.01)

(58) Field of Classification Search
CPC .. C07D 221/22; C07D 401/12; C07D 403/12; C07D 405/12; C07D 409/12; A61K 31/439; A61K 31/4709; A61P 29/00
See application file for complete search history.

(56) References Cited

FOREIGN PATENT DOCUMENTS

| CN | 110872253 | * | 3/2020 |
| CN | 112358487 A | | 2/2021 |

OTHER PUBLICATIONS

Gabbasov et al., Amides of N-Deacetyllappaconitine and Amino Acids, Chemistry of Natural Compounds, vol. 54, No. 5, pp. 951-955 (Year: 2018).*
Romanov et al., New Acyl Derivatives of N-Deacetyllappaconitine, Chemistry of Natural Compounds, vol. 44, No. 3, pp. 346-351 (Year: 2008).*
Dzhakhangirov et al., Toxicity and Local Anesthetic Activity of Diterpenoid Alkaloids, Chemistry of Natural Compounds, vol. 43, No. 5, pp. 581-589 (Year: 2007).*
Ross et al., New Synthetic Derivatives of Aconitine, Delphonine and N-Deacetyllappaconitine, Heterocycles, vol. 32, No. 7, pp. 1307-1315 (Year: 1991).*
Yue J. The analysis of treatment effect on urethra syndrome by lappaconitini hydrobromidum and amitriptylinum [J] Journal of Qinghai Medical College, 1996, 17(2):1. DOI: CNKI:SUN:QHYX.0.1996-02-02.

* cited by examiner

*Primary Examiner* — Brenda L Coleman

(57) ABSTRACT

Provided herein are a lappaconitine derivative of formula (I), and a preparation and application thereof.

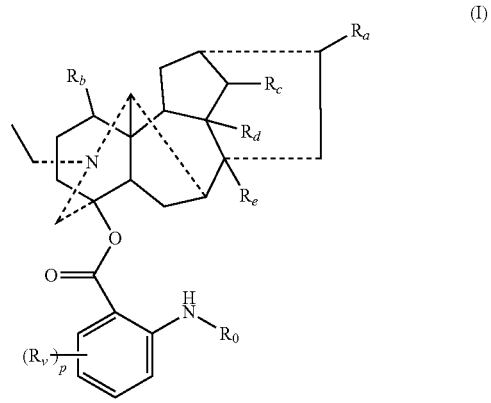

(I)

10 Claims, No Drawings

LAPPACONITINE DERIVATIVE WITH ANALGESIC ACTIVITY, AND PREPARATION AND APPLICATION THEREOF

CROSS-REFERENCE TO RELATED APPLICATIONS

This application claims the benefit of priority from Chinese Patent Application No. 202110419203.4, filed on Apr. 19, 2021. The content of the aforementioned application, including any intervening amendments thereto, is incorporated herein by reference in its entirety.

TECHNICAL FIELD

This application relates to pharmaceutical preparation, and more particularly to a lappaconitine derivative with analgesic activity, and a preparation and application thereof.

BACKGROUND

Lappaconitine (LA) is a C18-diterpenoid alkaloid naturally occurring in the root of *Aconitum sinomontanum* Nakai of the Ranunculaceae family, and is usually prepared into lappaconitine hydrobromide for clinical application. It has been reported that lappaconitine has analgesia, anti-inflammatory, apocatastasis and antipyretic effects.

Lappaconitine is particularly prominent in relieving inflammatory pain due to the excellent anti-inflammatory activity, and has been clinically used in the treatment of pain caused by rheumatoid arthritis. Yue Jianhua (Yue J. The analysis of treatment effect on urethra syndrome by lappaconitini hydrobromidum and amitriptylinum [J]*Journal of Qinghai Medical College*, 1996, 17(2):1. DOI: CNKI:SUN: QHYX.0.1996-02-023) as reported that lappaconitine can significantly alleviate urinary problems such as frequency, urgency and pain after urinary tract infection treatment by eliminating the chronic inflammation of the bladder caused by urinary tract infection.

Bureau of drug policy and administration of China has listed lappaconitine as an analgesic for mild and moderate pain in the three-step analgesic therapy for cancer patients, and the lappaconitine is mainly used for the mitigation of cancer pain in clinical practice. The analgesic mechanism of lappaconitine includes a general mechanism and a central mechanism. The former may be the analgesic mechanism of general antipyretic analgesics, while the latter is a special mechanism. The clinical application of lappaconitine mainly focuses on conventional pain treatment, especially the treatment of cancer pain, and recently, it has been gradually applied to the surgical analgesia and postoperative pain treatment.

Compared to the traditional analgesics, the lappaconitine has stronger analgesic effect, no dependence and no addiction. However, it also struggles with a narrow safety range and high toxicity, and may cause side effects such as chills, fever, allergic reactions, ototoxicity, arrhythmia and anaphylactic shock during the treatment.

Accordingly, the development of a new compound with low toxicity and high analgesic activity is of great significance to the clinical application of analgesics.

SUMMARY

An objective of the present disclosure is to provide a lappaconitine derivative with low toxicity and high analgesic activity, and a preparation and application thereof.

The technical solutions of the present disclosure are described as follows.

In a first aspect, the present disclosure provides a compound of formula (I), or a stereoisomer, a deuterated compound, a solvate, a prodrug, a metabolite or a pharmaceutically acceptable salt thereof

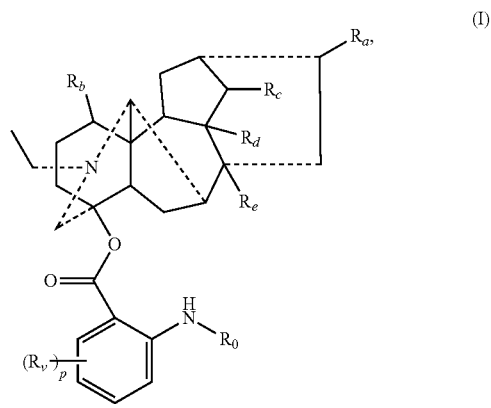

wherein $R_a$, $R_b$, $R_c$, $R_d$ and $R_e$ are each independently selected from the group consisting of hydroxyl, $C_{1-6}$ alkyl, $C_{1-6}$ alkoxy, $COOR_u$ and $OCOR_u$; wherein $R_u$ is hydrogen, $C_{1-6}$ alkyl, 5-6 membered aryl or 5-6 membered heteroaryl;

p is an integer selected from 0-4;

$R_v$ is each independently selected from the group consisting of hydrogen, hydroxyl, $C_{1-6}$ alkyl, $C_{1-6}$ alkoxy, halogen, $COOR_w$ and $OCOR_w$; wherein $R_w$ is hydrogen or $C_{1-6}$ alkyl;

$R_0$ is $COR_f$, $SO_2R_g$, $SOR_g$ or $C_{1-6}$ alkyl;

wherein $R_f$ is selected from the group consisting of $C_{2-6}$ alkyl, $C_{2-6}$ alkenyl, $C_{2-6}$ alkynyl, $MR_1$ 5-6 membered aryl substituted by one and more $R_x$, 5-6 membered heteroaryl substituted by one and more $R_x$, 3-8 membered saturated cycloalkyl substituted by one and more $R_x$, 3-8 membered saturated heterocyclic group substituted by one and more $R_x$, fused ring alkyl substituted by one and more $R_x$, heterofused ring group substituted by one and more $R_x$, bicycloalkyl group substituted by one and more $R_x$ and heterobicyclic group substituted by one and more $R_x$; wherein the $R_x$ is hydrogen, substituted or unsubstituted $C_{1-6}$ alkyl, substituted or unsubstituted $C_{1-6}$ alkoxy, $C_{2-6}$ alkenyl, $C_{2-6}$ alkynyl, $NR_3R_4$, $COOR_5$, $SO_2R_6$, halogen, cyano, nitro, hydroxyl, carboxy or phenyl; and a substituent group is halogen, $C_{1-6}$ alkyl or $C_{1-6}$ alkoxy;

M is O or NH; $R_1$ is $C_{1-6}$ alkyl, $C_{1-6}$ alkoxy, $C_{2-6}$ alkenyl, $C_{2-6}$ alkynyl, 5-6 membered aryl or 5-6 membered heteroaryl;

$R_g$ is $C_{1-6}$ alkyl, $C_{2-6}$ alkenyl, $C_{2-6}$ alkynyl or $L_1R_h$; wherein $L_1$ is absent or $C_{1-4}$ alkylene; $R_h$ is selected from the following groups substituted by one or more $R_y$: 5-6 membered aryl, 5-6 membered heteroaryl, 3-8 membered saturated cycloalkyl, 3-8 membered saturated heterocyclic group, fused ring alkyl, heterofused ring group, bicycloalkyl group and heterobicyclic group; wherein the $R_y$ is selected from the group consisting of hydrogen, substituted and unsubstituted $C_{1-6}$ alkyl, substituted and unsubstituted $C_{1-6}$ alkoxy, $C_{2-6}$ alkenyl, $C_{2-6}$ alkynyl, $NR_3R_4$, $COOR_5$, $SO_2R_6$, halogen, cyano, nitro, hydroxyl, carboxy and phenyl; and a substituent of the substituted $C_{1-6}$ alkyl and the substituted $C_{1-6}$ alkoxy is independently halogen, $C_{1-6}$ alkyl or $C_{1-6}$ alkoxy; and $R_3$, $R_4$, $R_5$ and $R_6$ are each independently selected from the group consisting of hydrogen and $C_{1-6}$ alkyl.

In some embodiments, the compound has a structure of formula (II):

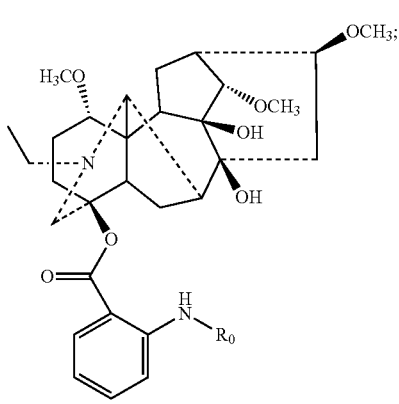

wherein $R_0$ is $COR_f$ or $SO_2R_g$;

wherein $R_f$ is $C_{2-6}$ alkyl, $C_{2-3}$ alkenyl, $C_{2-3}$ alkynyl, $MR_1$ or one of the following groups substituted by one or more $R_x$: 5-6 membered aryl, 5-6 membered heteroaryl, 3-6 membered saturated cycloalkyl, 3-6 membered saturated heterocyclic group, fused ring alkyl, heterofused ring group, bicycloalkyl group and heterobicyclic group; wherein the $R_x$ is selected from the group consisting of hydrogen, halogenated and unsubstituted $C_{1-4}$ alkyl, halogenated and unsubstituted $C_{1-4}$ alkoxy, $C_{2-4}$ alkenyl, $C_{2-4}$ alkynyl, $NR_3R_4$, $COOR_5$, $SO_2R_6$, halogen, cyano, nitro and phenyl;

M is O or NH; $R_1$ is $C_{1-4}$ alkyl, $C_{1-4}$ alkoxy, $C_{2-4}$ alkenyl, $C_{2-4}$ alkynyl, 5-6 membered aryl or 5-6 membered heteroaryl;

$R_g$ is $C_{1-6}$ alkyl, $C_{2-3}$ alkenyl, $C_{2-3}$ alkynyl or $L_1R_h$; wherein $L_1$ is absent or $C_{1-2}$ alkylene; $R_h$ is selected from the following groups substituted by one or more $R_y$: 5-6 membered aryl, 5-6 membered heteroaryl, 3-6 membered saturated cycloalkyl, 3-6 membered saturated heterocyclic group, fused ring alkyl, heterofused ring group, bicycloalkyl group and heterobicyclic group; wherein the $R_y$ is selected from the group consisting of hydrogen, halogenated and unsubstituted $C_{1-4}$ alkyl, halogenated and unsubstituted $C_{1-4}$ alkoxy, $C_{2-4}$ alkenyl, $C_{2-4}$ alkynyl, $NR_3R_4$, $COOR_5$, $SO_2R_6$, halogen, cyano, nitro and phenyl;

$R_3$, $R_4$, $R_5$ and $R_6$ are each independently selected from the group consisting of hydrogen and $C_{1-4}$ alkyl.

In some embodiments, the compound has a structure of formula (III):

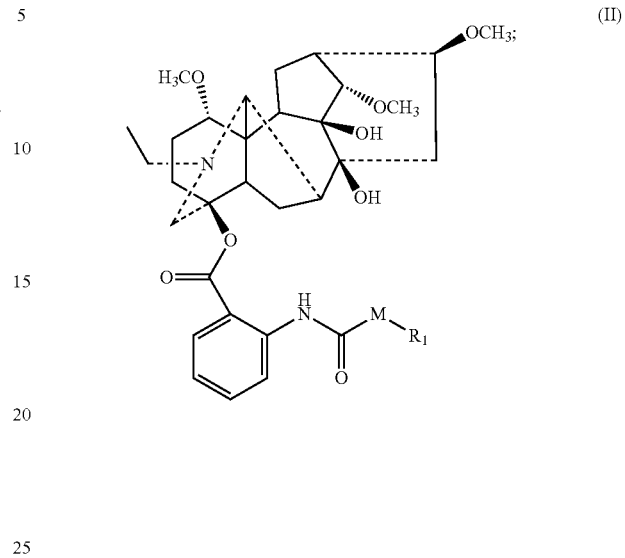

wherein M is O or NH;

$R_1$ is $C_{1-4}$ alkyl, $C_{1-4}$ alkoxy, $C_{2-4}$ alkenyl, $C_{2-4}$ alkynyl, 5-6 membered aryl or 5-6 membered heteroaryl.

In some embodiments, the compound has a structure of formula (IV):

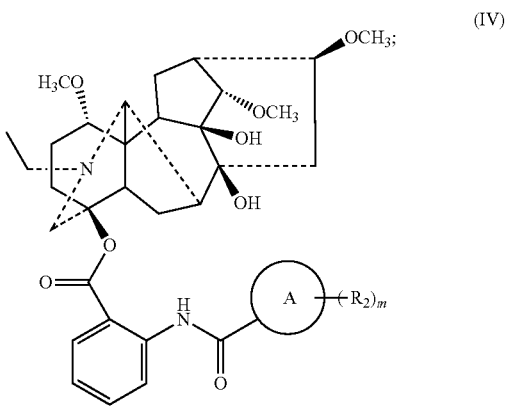

wherein m is an integer selected from 0-3;

$R_2$ is each independently selected from the group consisting of hydrogen, halogenated and unsubstituted $C_{1-4}$ alkyl, halogenated and unsubstituted $C_{1-4}$ alkoxy, $C_{2-4}$ alkenyl, $C_{2-4}$ alkynyl, $NR_3R_4$, $COOR_5$, $SO_2R_6$, halogen, cyano, nitro and phenyl; wherein $R_3$, $R_4$, $R_5$ and $R_6$ are each independently selected from the group consisting of hydrogen and $C_{1-4}$ alkyl; and ring A is 5-6 membered aryl, 5-6 membered heteroaryl, 3-6 membered saturated cycloalkyl or 3-6 membered saturated heterocyclic group.

In some embodiments, the compound has a structure of formula (V):

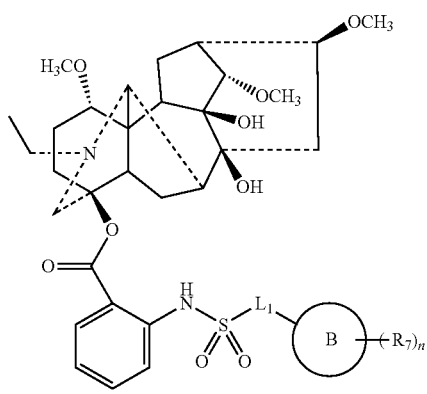

(V)

wherein L₁ is absent or $C_{1-2}$ alkylene;

n is an integer selected from 0-3;

$R_7$ is each independently selected from the group consisting of hydrogen, halogenated and unsubstituted $C_{1-4}$ alkyl, halogenated and unsubstituted $C_{1-4}$ alkoxy, $C_{2-4}$ alkenyl, $C_{2-4}$ alkynyl, $NR_3R_4$, $COOR_5$, $SO_2R_6$, halogen, cyano, nitro and phenyl; wherein $R_3$, $R_4$, $R_5$ and $R_6$ are each independently selected from the group consisting of hydrogen and $C_{1-4}$ alkyl; and ring B is 5-6 membered aryl, 5-6 membered heteroaryl, 3-6 membered saturated cycloalkyl, 3-6 membered saturated heterocyclic group, fused ring alkyl, heterofused ring group, bicycloalkyl group or heterobicyclic group.

In some embodiments, the compound has a structure selected from the group consisting of:

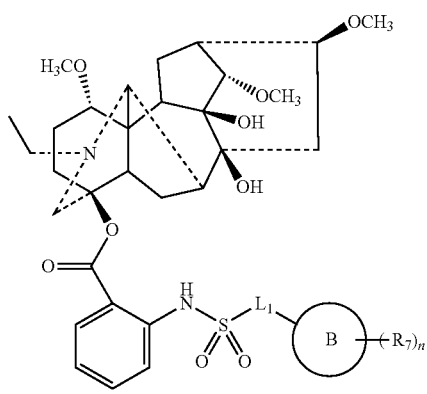
1

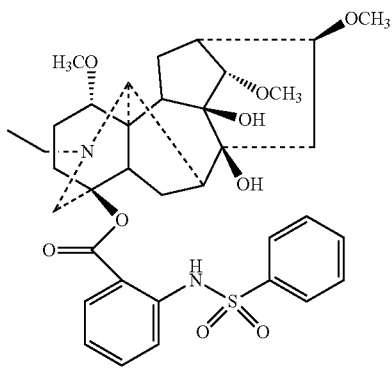
2

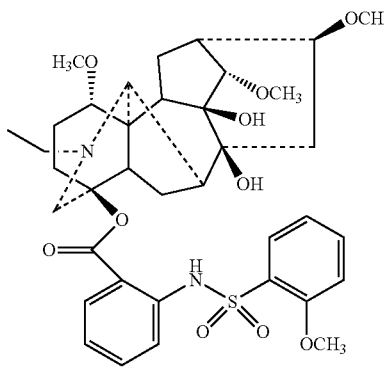
3

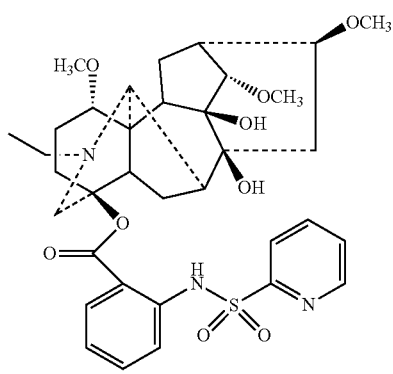
4

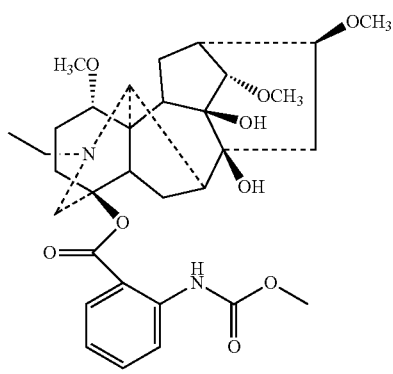
5

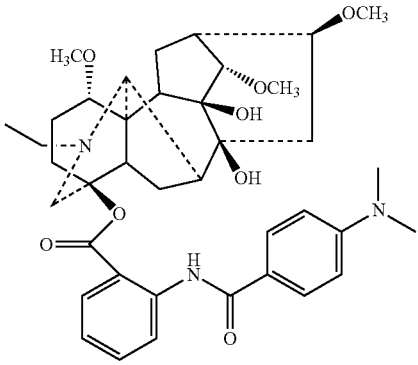
6

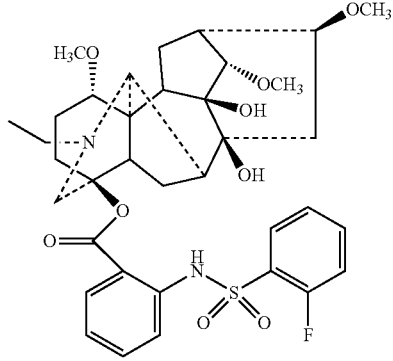

-continued

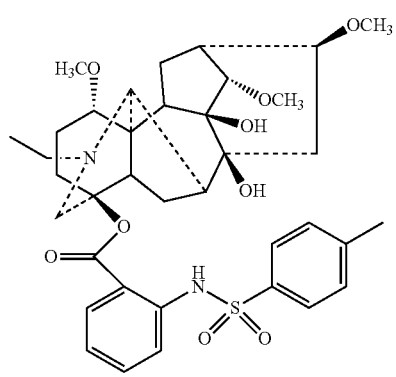
15
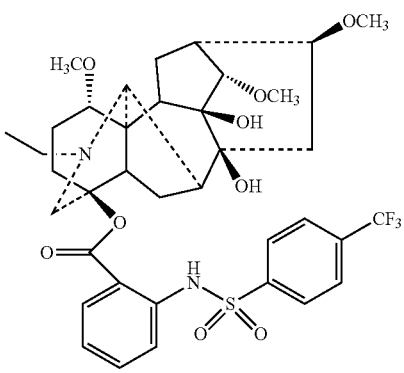
19
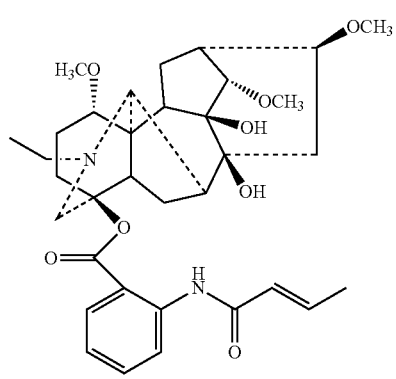
16
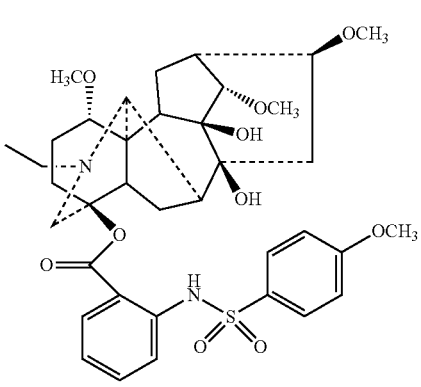
20
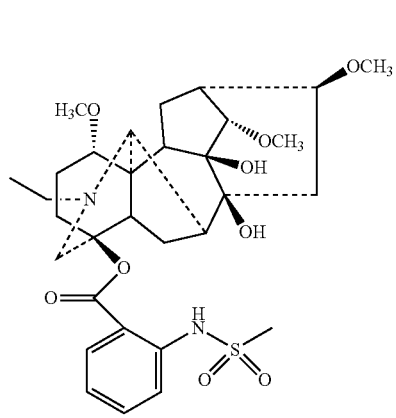
17
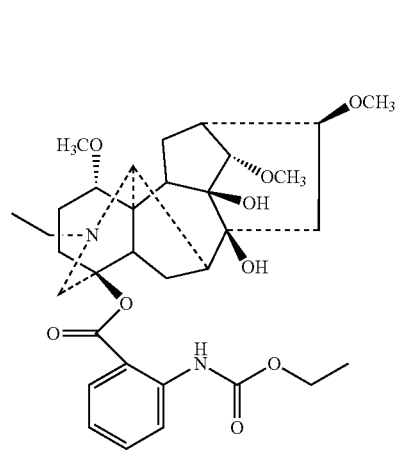
21
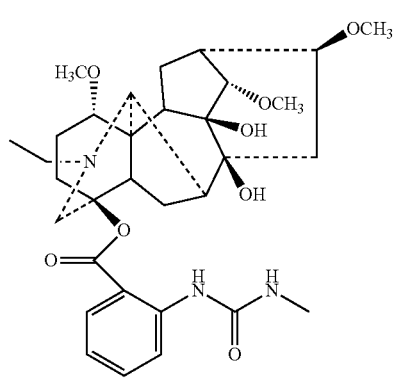
18
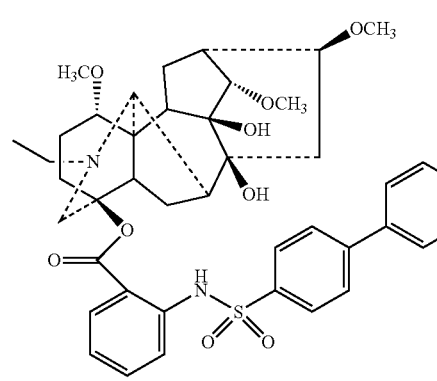
22

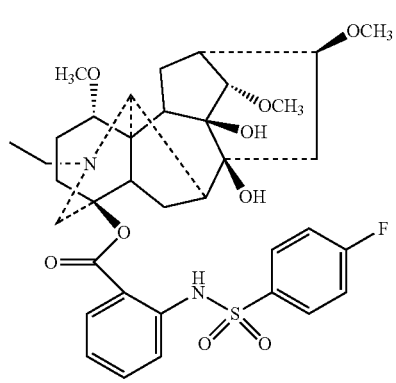
23
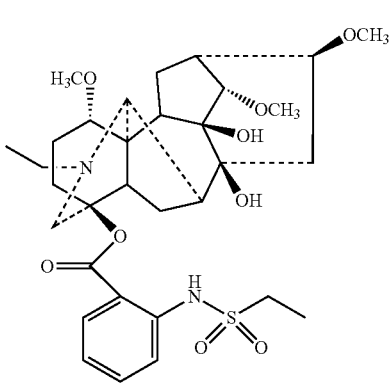
27
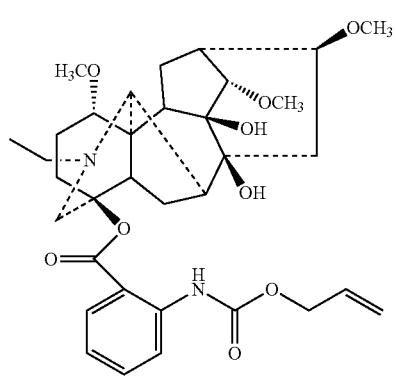
24
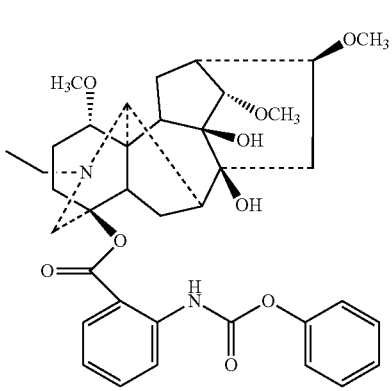
28
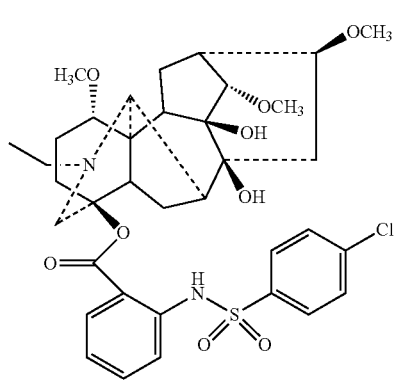
25
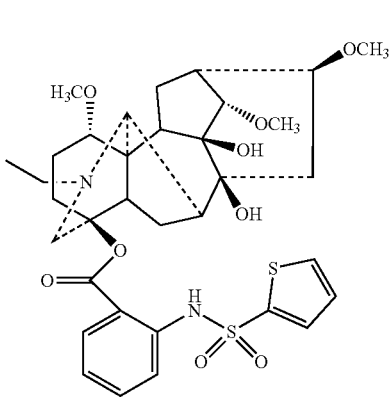
29
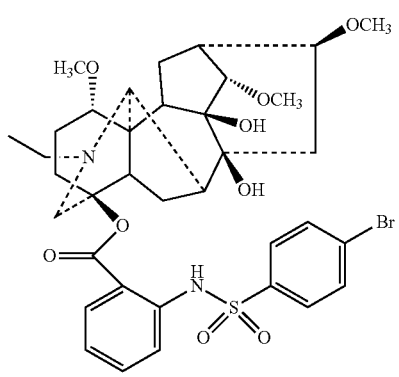
26
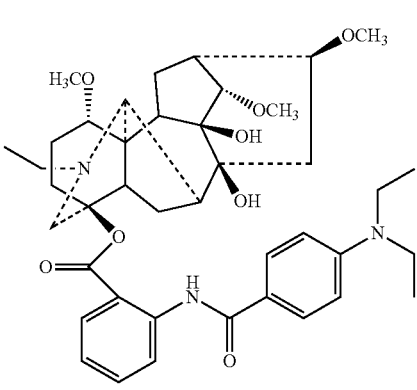
30

31
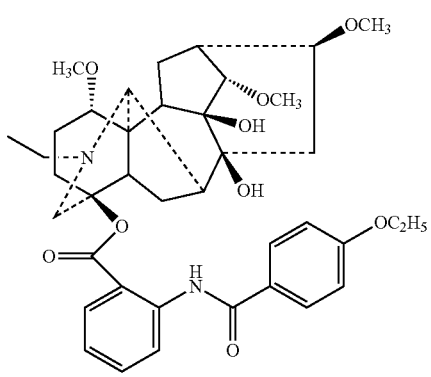
32
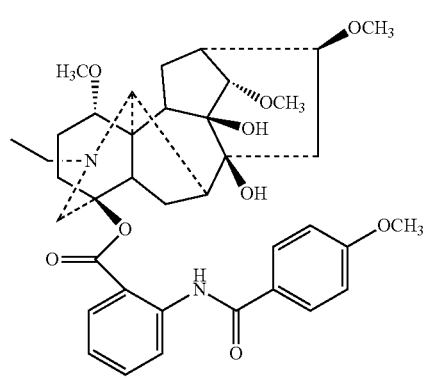
33
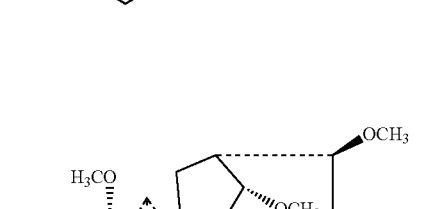
34
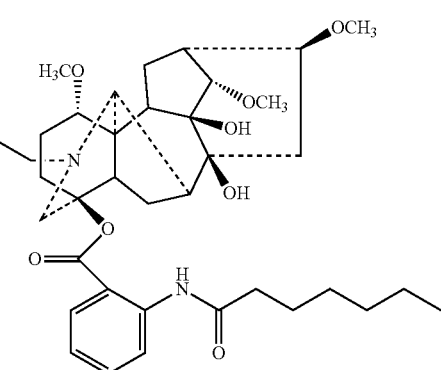
35
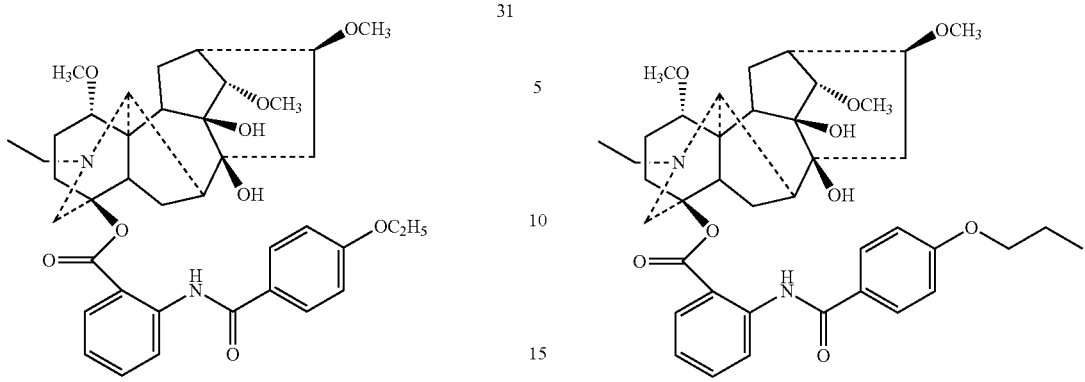
36
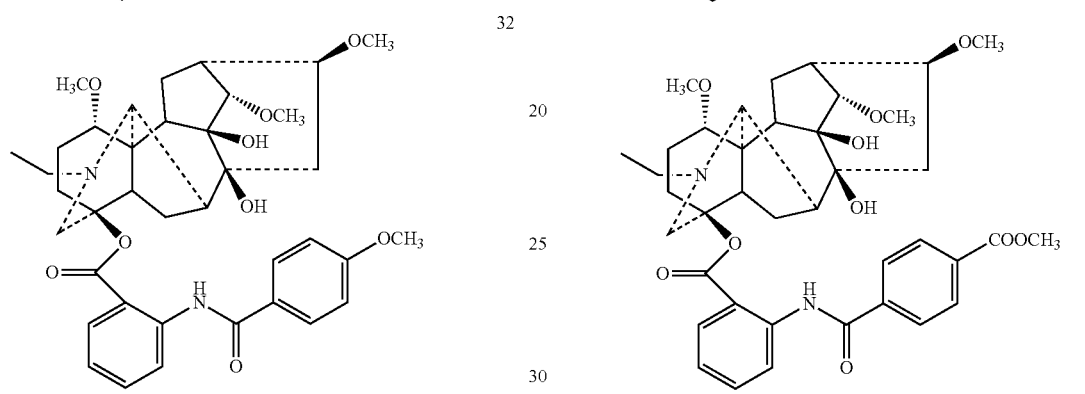
37
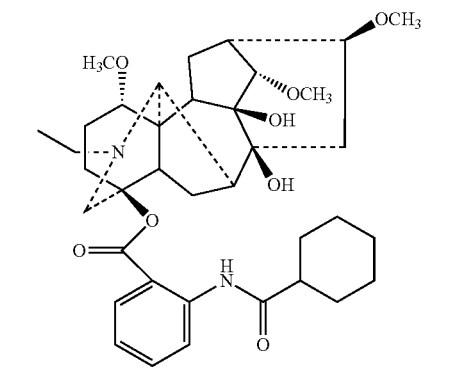
38
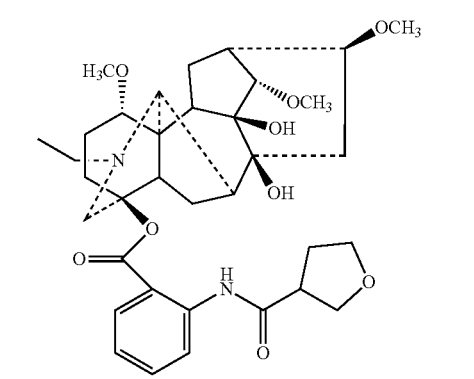

39
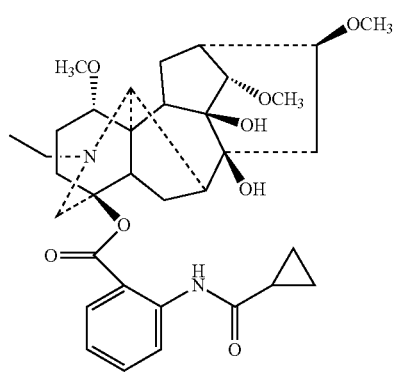
40
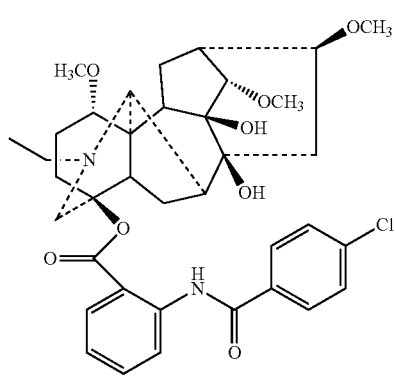
41
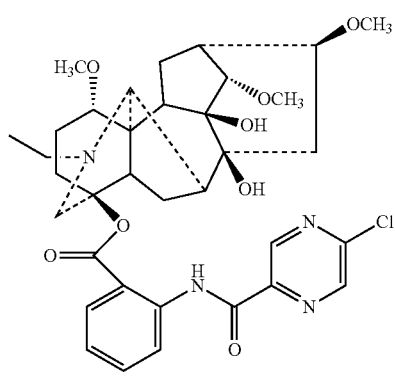
42
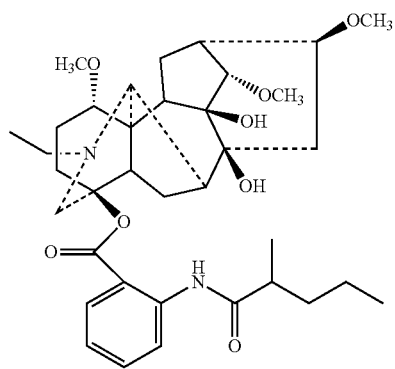
43
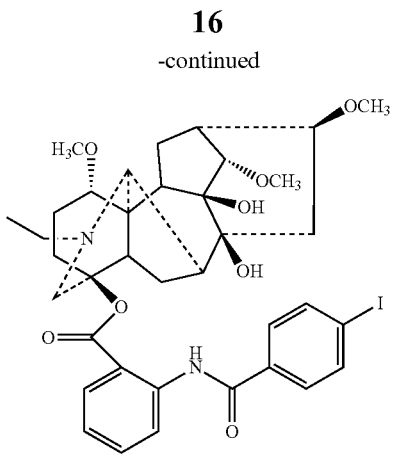
44
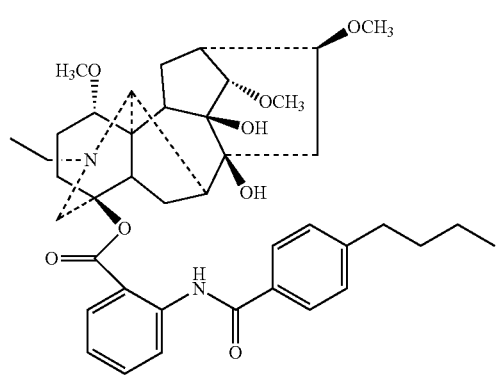
45
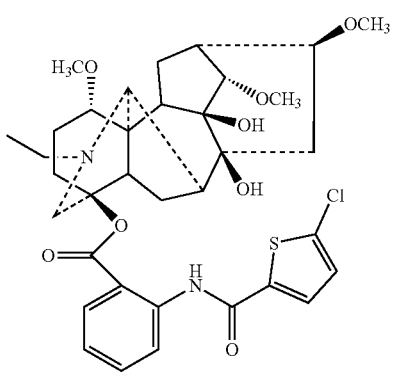
46
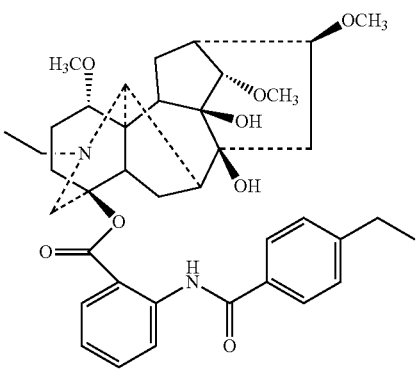

-continued

55

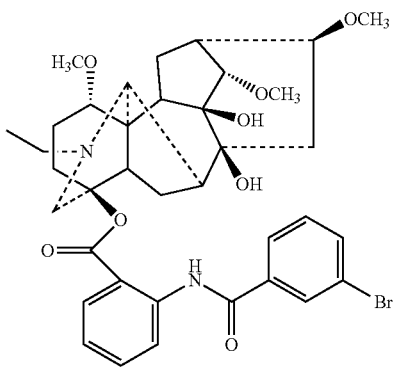

56

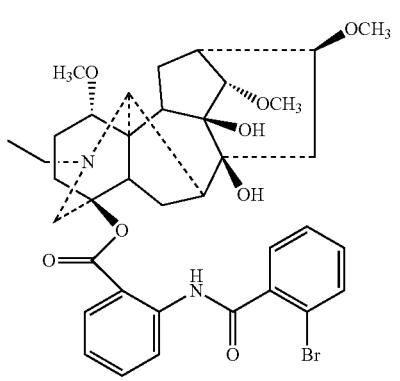

57

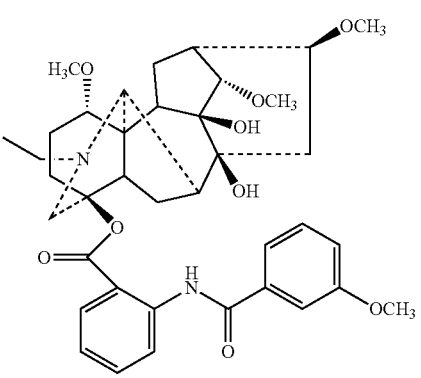

58

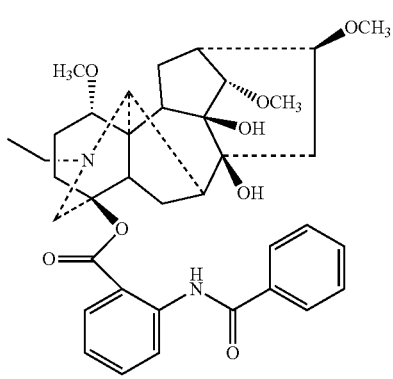

59

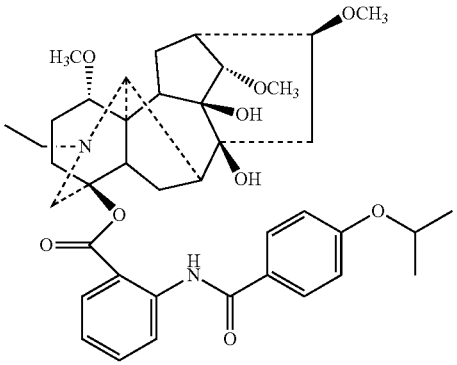

60

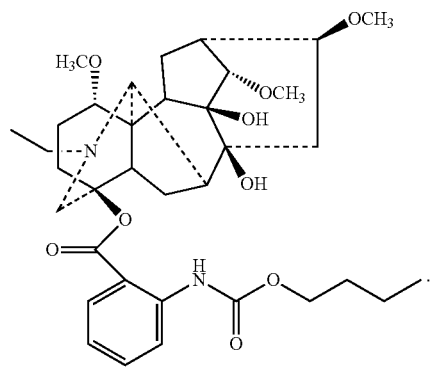

In a second aspect, the present disclosure provides an analgesic composition, made from the above-mentioned compound or a stereoisomer, a deuterated compound, a solvate, a prodrug, a metabolite or a pharmaceutically acceptable salt thereof and a pharmaceutically acceptable excipient.

In a third aspect, the present disclosure provides a method for relieving pain in a subject in need thereof, comprising: administering to the subject a pharmaceutically effective amount of the above-mentioned compound, or a stereoisomer, a deuterated compound, a solvate, a prodrug, a metabolite or a pharmaceutically acceptable salt thereof.

In some embodiments, the compound has low toxicity.

In some embodiments, a median lethal dose of the compound is higher than a median lethal dose of lappaconitine.

Experimental results show that the lappaconitine derivative provided herein has high analgesic activity, and low biological toxicity, can be used to prepare low-toxic analgesic pharmaceuticals, and has promising application prospects.

The preparation method of the lappaconitine derivative has simple operation and mild conditions, and is thus suitable for expanded production.

Unless otherwise specified, the initial definitions of groups or terms provided herein are applicable to the groups or terms throughout the specification. The terms not specifically defined herein can be understood by those skilled in the art based on the description of the present disclosure.

With respect to the compound represented by the formula (I), when the $R_g$ is the $L_1R_h$ and the $L_1$ is absent, the $R_g$ is the $R_h$.

The minimum and maximum content of carbon atoms in a hydrocarbon group are indicated by prefixes. For example, the prefix $C_{a-b}$ alkyl represents any alkyl group containing "a" to "b" carbon atoms. For example, $C_{1-6}$ alkyl refers to a straight or branched chain alkyl containing 1 to 6 carbon atoms.

The term "substitution" used herein refers to the replacement of one or more hydrogen atoms in a molecule with other different atoms or molecules, including one or more substitutions on the same or different atoms of the molecule.

The term "aryl" refers to groups of an all-carbon monocyclic or fused polycyclic (that is, rings that share adjacent pairs of carbon atoms) with a conjugated R-electron system, such as phenyl and naphthyl. The aryl ring may be fused to other cyclic groups (including saturated and unsaturated rings), but cannot contain heteroatoms such as nitrogen, oxygen and sulfur, and the point of connection to the parent must be on the carbon atom of the ring with the conjugated π-electron system. Aryl groups may be substituted or unsubstituted.

The term "heteroaryl" refers to a heteroaromatic group containing one to more heteroatoms. The heteroatoms referred herein include oxygen, sulfur and nitrogen. For example, furyl, thienyl, pyridyl, pyrazolyl, pyrrolyl, N-alkylpyrrolyl, pyrimidinyl, pyrazinyl, imidazolyl and tetrazolyl. The heteroaryl ring may be fused to an aryl, heterocyclic or cycloalkyl ring, and the ring connected to the parent structure is a heteroaryl ring. Heteroaryl groups may be optionally substituted or unsubstituted.

"Deuterated compound" is a compound on which one or more hydrogens are replaced with deuterium.

The term "bicycloalkyl" refers to a polycyclic cycloalkyl group in which two rings are linked by a single bond, e.g.,

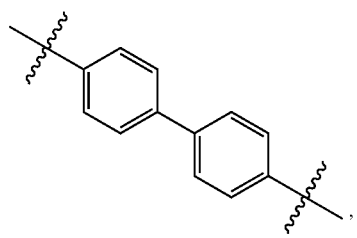 [SMILES: *c1ccc(-c2ccc(*)cc2)cc1]

The term "heterocyclic ring group" refers to a polycyclic group in which two rings are connected by a single bond, and at least one of the two rings is a heterocyclic ring, e.g.,

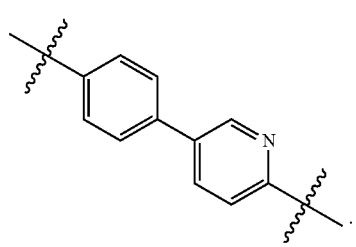 [SMILES: *c1ccc(-c2ccc(*)nc2)cc1]

The term "fused cycloalkyl" refers to a polycyclic cycloalkyl group in which two rings share two adjacent carbon atoms, e.g.,

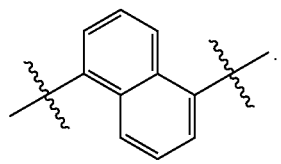 [SMILES: *c1cccc2c(*)cccc12]

The term "hetero-fused ring group" refers to a polycyclic group in which two rings share two adjacent carbon atoms, and at least one of the two rings is a heterocyclic ring, e.g.,

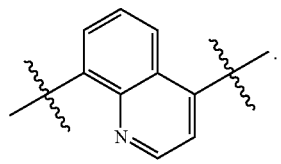 [SMILES: *c1ccnc2c(*)cccc12]

Halogen refers to fluorine, chlorine, bromine or iodine.

The term "pharmaceutically acceptable" means that a carrier, a diluent, an excipient and/or the formed salt is usually chemically or physically compatible with other ingredients constituting a certain pharmaceutical dosage form, and is physiologically compatible with the receptor.

The term "salt" refers to an acid or a basic salt formed by combining a compound or its stereoisomer with an inorganic or organic acid or a base, and may also refers to a zwitterionic salt (internal salt) or a quaternary ammonium salt such as an alkyl ammonium salt. These salts may be obtained directly in the final isolation and purification of the compound, and may also be obtained by mixing the compound or its stereoisomer with a certain amount of acid or base appropriately (for example, equivalent). These salts may be collected through collecting a precipitate in a solution through filtration, or recovered after evaporation of a solvent. These salts may also be obtained by freeze-drying after reacting in an aqueous medium.

The pharmaceutically acceptable salt described herein may be a hydrochloride, a sulfate, a citrate, a benzenesulfonate, a hydrobromide, a hydrofluoride, a phosphate, an acetate, a propionate, an oxalate, a malate, a succinate, a fumarate, a maleate, a tartrate or a trifluoroacetate.

Obviously, various modifications, replacements and alterations can be made by those skilled in the art without departing from the spirit of the present disclosure.

The present disclosure will be further described below with reference to the embodiments. It should be noted that the embodiments provided herein are not intended to limit the present disclosure, and technical solutions obtained based on this disclosure should fall within the scope of the present disclosure.

DETAILED DESCRIPTION OF EMBODIMENTS

The raw materials and equipment used herein are all known products and commercially available.

The target compound of the disclosure is synthesized according to the following route:

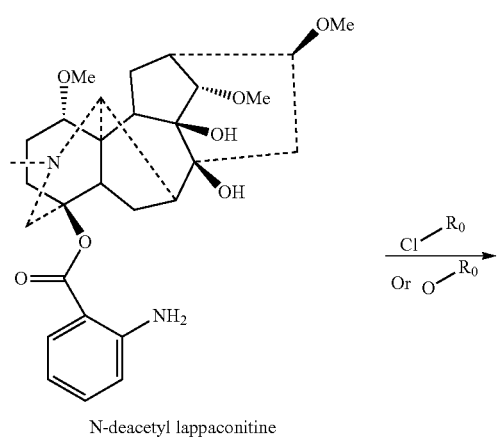

N-deacetyl lappaconitine

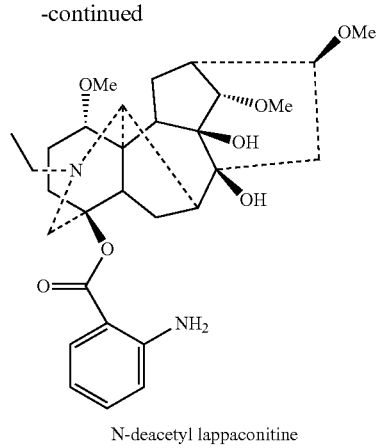

N-deacetyl lappaconitine

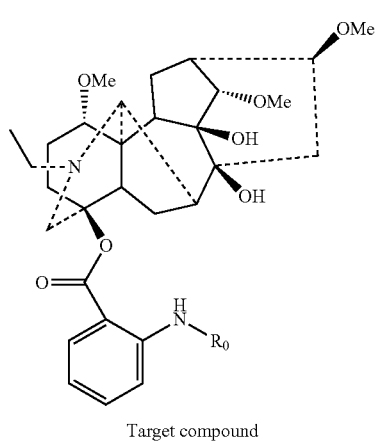

Target compound in which N-deacetyl lappaconitine is purchased or synthesized according to the following route.

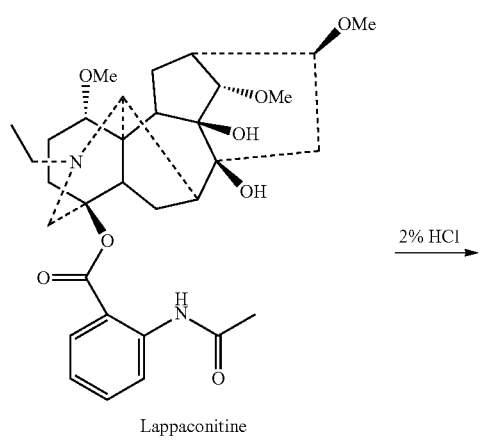

Lappaconitine

Example 1 Preparation of Compound 1 with Lappaconitine and Benzenesulfonyl Chloride 110 mg of N-deacetyl lappaconitine was added into a 5 mL round-bottom flask, and dissolved with 2 mL of dry dichloromethane. 200 μL of dry pyridine was dropwise added under the protection of Ar, and 98 mg of benzenesulfonyl chloride was introduced under an ice bath. The reaction mixture was reacted at 20° C., where the reaction was monitored by thin-layer chromatography. After reacted for 14 h, the reaction mixture was subjected to rotary evaporation, and purified by column chromatography to obtain 129 mg of a light yellow solid as a target compound 1 $C_{36}H_{46}N_2O_9S$ (93.2% yield), which was structurally shown as follows:

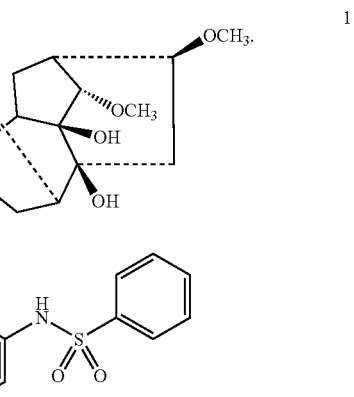

The target compound 1 was characterized as follows.

$^1$H-NMR (400 MHz, CDCl$_3$) δ: 10.51 (s, 1H), 7.79 (t, J=8.6 Hz, 3H), 7.63 (d, J=8.2 Hz, 1H), 7.50 (s, 1H), 7.41 (t, J=7.8 Hz, 3H), 6.99 (t, J=7.6 Hz, 1H), 3.53 (d, J=11.3 Hz, 2H), 3.43 (d, J=4.7 Hz, 1H), 3.40 (s, 3H), 3.31 (s, 3H), 3.29 (s, 3H), 3.16 (dd, J=10.2, 7.0 Hz, 1H), 2.98 (s, 1H), 2.67-2.45 (m, 5H), 2.43-2.34 (m, 3H), 2.32-2.26 (m, 2H), 2.14-1.95 (m, 4H), 1.68 (t, J=15.0 Hz, 1H), 1.41 (s, 1H), 1.28 (s, 1H), 1.12 (t, J=7.2 Hz, 3H).

$^{13}$C-NMR (100 MHz, CDCl$_3$): δ 167.2, 139.7, 134.3, 133.0, 131.5, 129.1, 129.1, 127.3, 127.3, 123.3, 119.9, 117.6, 90.3, 85.2, 84.2, 83.0, 78.7, 75.8, 61.6, 58.1, 56.7, 56.3, 55.5, 51.1, 50.0, 49.1, 48.7, 47.7, 45.1, 36.5, 31.9, 26.9, 26.4, 24.2, 18.6, 13.7.

HR-ESI-MS m/z: [(M+H)$^+$, 683.3052].

Example 2 Preparation of Compound 2 with Lappaconitine and 2-Methoxybenzenesulfonyl Chloride 120 mg of N-deacetyl lappaconitine was added into a 5 mL round-bottom flask, and dissolved with 2 mL of dry dichloromethane. 105 mg of dry pyridine was dropwise added under the protection of Ar, and 137 mg of 2-methoxybenzenesulfonyl chloride was introduced under an ice bath. The reaction mixture was reacted at 5° C., where the reaction was monitored by thin-layer chromatography. After reacted for 29.5 h, the reaction mixture was filtered to collect a filter cake, which was separated and purified by column chromatography to obtain 116 mg of a white foamy solid as a target compound 2 C$_{37}$H$_{48}$N$_2$O$_{10}$S (73.6% yield), which was structurally shown as follows:

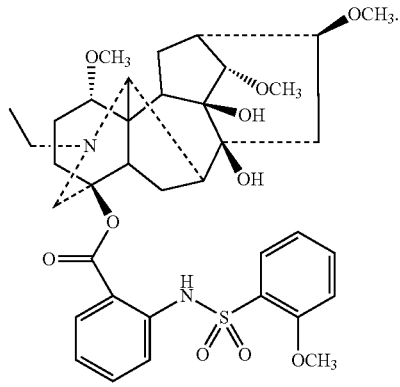

The target compound 2 was characterized as follows.

$^1$H-NMR (400 MHz, CDCl$_3$) δ: 11.11 (s, 1H), 8.00 (d, J=7.8 Hz, 1H), 7.83 (d, J=9.4 Hz, 1H), 7.64 (d, J=8.4 Hz, 1H), 7.46 (t, J=8.8 Hz, 1H), 7.32 (t, J=8.6 Hz, 1H), 7.00 (t, J=7.6 Hz, 1H), 6.90 (t, J=8.8 Hz, 2H), 3.85 (s, 3H), 3.58 (d, J=11.4 Hz, 1H), 3.53 (s, 1H), 3.41 (s, 3H), 3.32 (s, 3H), 3.31 (s, 3H), 3.19 (dd, J=10.2, 7.2 Hz, 1H), 3.01 (s, 1H), 2.70-2.36 (m, 10H), 2.18-1.92 (m, 5H), 1.86 (t, J=11.8 Hz, 1H), 1.54 (dd, J=15.0, 8.2 Hz, 1H), 1.36-1.24 (m, 1H), 1.12 (t, J=7.1 Hz, 3H).

$^{13}$C-NMR (100 MHz, CDCl$_3$) δ: 166.9, 156.7, 141.0, 135.1, 134.3, 131.5, 131.3, 126.6, 122.0, 120.1, 117.4, 115.9, 112.0, 90.2, 84.8, 84.2, 82.9, 78.6, 75.7, 61.7, 58.0, 56.6, 56.2, 56.0, 55.7, 51.0, 49.9, 49.1, 48.4, 47.6, 44.9, 36.3, 31.9, 26.9, 26.3, 24.2, 13.6.

HR-ESI-MS m/z: [(M+H)$^+$, 713.3173].

Example 3 Preparation of Compound 3 with Lappaconitine and 2-Pyridinesulfonic Acid 351 mg of 2-pyridinesulfonic acid was suspended in 5 mL of dry dichloromethane, to which 447 mg of triethylamine was introduced under an ice bath. The reaction mixture was stirred for 15 min to allow the 2-pyridinesulfonic acid to be completely dissolved. Then the reaction mixture was added with 624 mg of trifluoromethanesulfonic anhydride, reacted under an ice bath for 2 h. After that, 600 mg of N-deacetyl lappaconitine was added, and the reaction mixture was reacted in an ice bath, where the reaction was monitored by thin-layer chromatography. After reacted for 1.5 h, the reaction mixture was subjected to rotary evaporation, and purified by column chromatography to obtain 537 mg of a yellow foamy solid as a target compound 3 C$_{35}$H$_{45}$N$_3$O$_9$S (71.1% yield), which was structurally shown as follows:

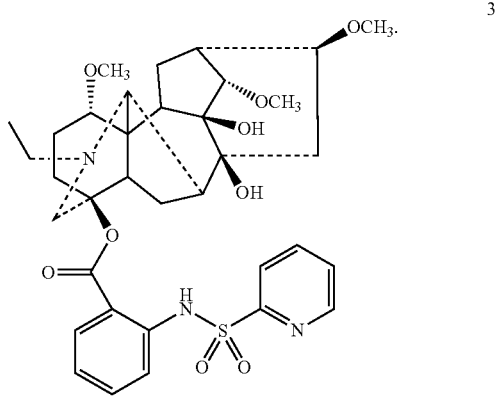

The target compound 3 was characterized as follows.

$^1$H-NMR (400 MHz, CDCl$_3$) δ: 10.94 (s, 1H), 8.63 (s, 1H), 8.03 (d, J=7.8 Hz, 1H), 7.87 (t, J=7.4 Hz, 1H), 7.79 (dd, J=20.7, 8.0 Hz, 2H), 7.48-7.37 (m, 2H), 7.00 (t, J=7.4 Hz, 1H), 3.60 (d, J=11.3 Hz, 2H), 3.45 (s, 1H), 3.41 (s, 3H), 3.32 (s, 3H), 3.30 (s, 3H), 3.22-3.15 (m, 1H), 3.00 (s, 1H), 2.72-2.63 (m, 2H), 2.50 (dd, J=13.2, 6.6 Hz, 3H), 2.37 (dt, J=18.0, 6.4 Hz, 4H), 2.20-1.94 (m, 6H), 1.53 (dd, J=14.6, 8.0 Hz, 1H), 1.36-1.23 (m, 1H), 1.12 (t, J=7.1 Hz, 3H).

$^{13}$C-NMR (100 MHz, CDCl$_3$) δ: 167.0, 156.9, 150.1, 140.3, 138.1, 134.2, 131.3, 127.0, 123.0, 122.7, 119.3, 117.3, 90.2, 85.1, 84.2, 82.9, 78.7, 75.7, 61.6, 58.0, 56.6, 56.2, 55.3, 51.0, 49.9, 49.1, 48.6, 47.6, 44.9, 36.3, 31.8, 26.9, 26.3, 24.2, 13.6.

HR-ESI-MS m/z: [(M+H)$^+$, 684.3010].

Example 4 Preparation of Compound 4 with Lappaconitine and Methyl Chloroformate 100 mg of N-deacetyl lappaconitine was added into a 5 mL round-bottom flask, and dissolved with 2 mL of dry toluene. 112 mg of triethylamine was dropwise added under the protection of Ar, and 52 mg of methyl chloroformate was introduced under an ice bath. The reaction mixture was reacted under 30° C., where the reaction was monitored by thin-layer chromatography. After reacted for 0.5 h, the reaction mixture was further added with 800 mg of methyl chloroformate followed by reacting for 0.5 h. The reaction mixture was then subjected to rotary evaporation, and purified by column chromatography to obtain 100 mg of a light yellow foamy solid as a target compound 4 $C_{32}H_{44}N_2O$ (90.3% yield), which was structurally shown as follows:

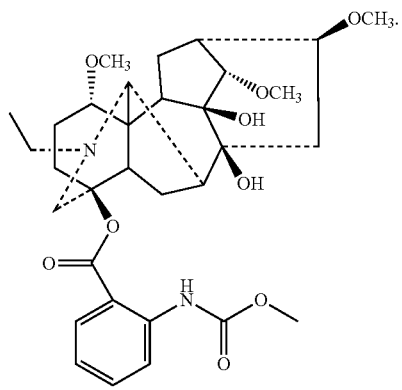

The target compound 4 was characterized as follows.

$^1$H-NMR (400 MHz, CDCl$_3$) δ: 10.54 (s, 1H), 8.39 (d, J=8.4 Hz, 1H), 7.91 (d, J=9.5 Hz, 1H), 7.49 (t, J=8.0 Hz, 1H), 6.98 (t, J=8.0 Hz, 1H), 3.77 (s, 3H), 3.61 (d, J=11.4 Hz, 1H), 3.54 (s, 1H), 3.44 (d, J=4.8 Hz, 1H), 3.41 (s, 3H), 3.31 (s, 3H), 3.29 (s, 3H), 3.18 (dd, J=10.2, 7.0 Hz, 1H), 3.00 (s, 1H), 2.72-2.65 (m, 2H), 2.61-2.46 (m, 4H), 2.44-2.35 (m, 3H), 2.31-2.22 (m, 2H), 2.15 (d, J=8.0 Hz, 1H), 2.12-2.06 (m, 1H), 2.01 (dd, J=14.8, 7.4 Hz, 2H), 1.83-1.68 (m, 1H), 1.59 (dd, J=15.2, 8.2 Hz, 1H), 1.11 (t, J=7.2 Hz, 3H).

$^{13}$C-NMR (100 MHz, CDCl$_3$) δ: 167.4, 154.2, 141.9, 134.5, 131.3, 121.6, 118.8, 115.6, 90.3, 84.6, 84.3, 83.0, 78.7, 75.8, 61.7, 58.1, 56.7, 56.3, 55.6, 52.4, 51.1, 50.0, 49.2, 48.8, 47.7, 45.0, 36.4, 31.9, 26.9, 26.4, 24.3, 13.7.

HR-ESI-MS m/z: [(M+H)$^+$, 601.3140].

Example 5 Preparation of Compound 5 with Lappaconitine and 4-Dimethylaminobenzoyl Chloride 300 mg of N-deacetyl lappaconitine was added into a 25 mL round-bottom flask, and dissolved with 5 mL of dry dichloromethane. 300 μL of dry pyridine was dropwise added under the protection of Ar. 300 mg of solid 4-dimethylaminobenzoyl chloride was dissolved with 5 mL of dry dichloromethane, and dropwise added to the round-bottom flask in an ice bath. The reaction mixture was reacted at 20° C., where the reaction was monitored by thin layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 323 mg of a light yellow foamy solid as a target compound 5 $C_{39}H_{51}N_3O_8$ (84.8% yield), which was structurally shown as follows:

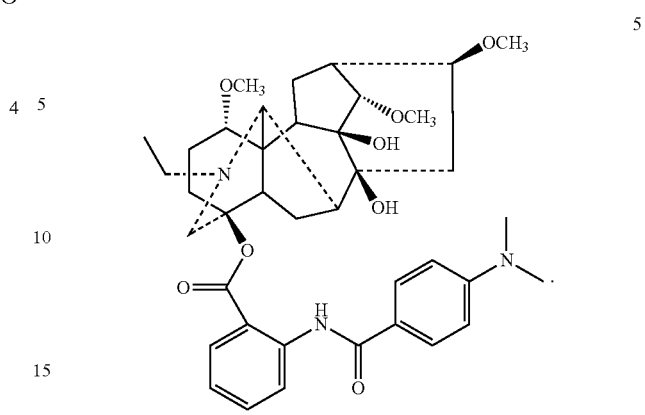

The target compound 5 was characterized as follows.

$^1$H-NMR (400 MHz, CDCl$_3$) δ: 11.86 (s, 1H), 8.90 (d, J=8.0 Hz, 1H), 7.99-7.91 (m, 2H), 7.95 (d, J=9.0 Hz, 1H), 7.53 (t, J=8.6 Hz, 1H), 7.02 (t, J=7.8 Hz, 1H), 6.76 (d, J=9.0 Hz, 1H), 5.30 (s, 1H), 4.12 (q, J=7.2 Hz, 1H), 3.62 (d, J=11.4 Hz, 1H), 3.56 (s, 1H), 3.45 (d, J=4.8 Hz, 1H), 3.41 (s, 3H), 3.32 (s, 3H), 3.30 (s, 3H), 3.21 (dd, J=10.4, 7.0 Hz, 1H), 3.06 (s, 6H), 3.02 (s, 1H), 2.74-2.65 (m, 2H), 2.64-2.47 (m, 4H), 2.46-2.35 (m, 3H), 2.27 (s, 1H), 2.17 (d, J=8.1 Hz, 2H), 2.12 (dd, J=12.4, 4.4 Hz, 1H), 2.04 (s, 1H), 1.65 (d, J=8.4 Hz, 1H), 1.26 (t, J=7.2 Hz, 1H), 1.13 (t, J=7.2 Hz, 3H).

$^{13}$C-NMR (100 MHz, CDCl$_3$) δ: 167.9, 166.0, 152.8, 142.7, 134.5, 131.2, 129.2×2, 121.9, 121.8, 120.5, 116.0, 111.3×2, 90.3, 84.5, 84.4, 83.1, 78.7, 75.8, 61.7, 58.1, 56.7, 56.3, 55.7, 51.1, 49.9, 49.2, 48.7, 47.7, 45.0, 40.2×2, 36.5, 31.9, 27.0, 26.4, 24.3, 13.7.

HR-ESI-MS m/z: [(M+H)$^+$, 690.3864].

Example 6 Preparation of Compound 6 with Lappaconitine and 2-Fluorobenzenesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 129 mg of 2-fluorobenzenesulfonyl chloride was introduced under an ice bath. The reaction mixture was reacted at 5° C., where the reaction was monitored by thin-layer chromatography. After reacted for 20 h, the reaction mixture was filtered to collect a filter cake, which was separated and purified by column chromatography to obtain 125 mg of a yellow-white foamy solid as a target compound 6 $C_{36}H_{45}FN_2O_9S$ (73.5% yield), which was structurally shown as follows:

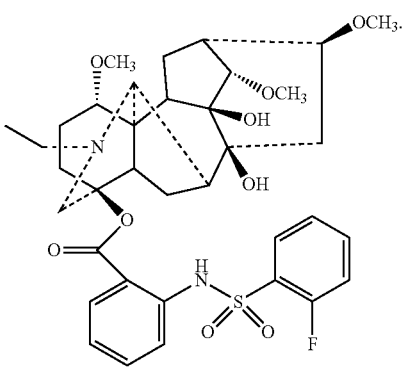

6

The target compound 6 was characterized as follows.

¹H-NMR (400 MHz, CDCl₃) δ: 7.95 (td, J=7.6, 1.8 Hz, 1H), 83 (dd, J=8.0, 1.8 Hz, 1H), 7.57 (d, J=8.4 Hz, 1H), 7.54-7.49 (m, 1H), 7.40-7.33 (m, 1H), 7.23 (t, J=7.8 Hz, 1H), 7.11 (t, J=9.2 Hz, 1H), 6.98 (t, J=7.6 Hz, 1H), 5.30 (s, 1H), 3.62 (d, J=11.6 Hz, 1H), 3.56 (s, 1H), 3.45 (d, J=4.8 Hz, 1H), 3.41 (s, 3H), 3.32 (s, 3H), 3.30 (s, 3H), 3.19 (dd, J=10.4, 7.0 Hz, 1H), 3.01 (s, 1H), 2.73-2.64 (m, 2H), 2.59-2.47 (m, 4H), 2.44-2.31 (m, 4H), 2.18-1.96 (m, 5H), 1.80-1.70 (m, 1H), 1.53 (dd, J=15.2, 8.2 Hz, 1H), 1.13 (t, J=7.2 Hz, 3H).

¹³C-NMR (100 MHz, CDCl₃) δ: 167.0, 139.9, 135.6, 134.2, 131.5, 131.0, 124.4, 122.9, 118.2, 117.3, 90.2, 85.2, 84.2, 83.0, 78.7, 77.5, 77.2, 76.8, 75.7, 61.6, 58.0, 56.6, 56.2, 55.4, 51.1, 49.9, 49.1, 48.7, 47.7, 44.9, 36.3, 31.8, 26.9, 26.2, 24.2, 13.6.

HR-ESI-MS m/z: [(M+H)⁺, 701.2905].

Example 7 Preparation of Compound 7 with Lappaconitine and 3-Fluorobenzenesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 129 mg of 3-fluorobenzenesulfonyl chloride was introduced under an ice bath. The reaction mixture was reacted at 5° C., where the reaction was monitored by thin-layer chromatography. After reacted for 16 h, the reaction mixture was purified by column chromatography to obtain 114 mg of a yellow-white foamy solid as a target compound 7 C₃H₄₅FN₂O₉S (73.5% yield), which was structurally shown as follows:

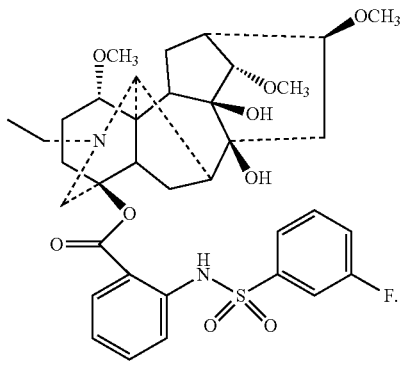

7

The target compound 7 was characterized as follows.

¹H-NMR (400 MHz, CDCl₃) δ: 7.79 (dd, J=8.0, 1.6 Hz, 1H), 7.62 (d, J=8.4 Hz, 1H), 7.56 (d, J=8.0 Hz, 1H), 7.51 (dt, J=8.2, 2.2 Hz, 1H), 7.46-7.35 (m, 2H), 7.19 (td, J=8.4, 2.6 Hz, 1H), 7.02 (t, J=7.6 Hz, 1H), 3.53 (d, J=11.4 Hz, 2H), 3.42 (d, J=5.0 Hz, 1H), 3.39 (s, 3H), 3.30 (s, 3H), 3.28 (s, 3H), 3.15 (dd, J=10.2, 7.0 Hz, 1H), 2.98 (s, 1H), 2.63 (dd, J=15.2, 7.6 Hz, 1H), 2.59-2.53 (m, 2H), 2.52-2.44 (m, 2H), 2.44-2.33 (m, 4H), 2.30 (d, J=7.2 Hz, 2H), 2.14-1.92 (m, 5H), 1.67 (m, 1H), 1.45 (dd, J=15.2, 8.2 Hz, 1H), 1.11 (t, J=7.2 Hz, 3H).

13C-NMR (100 MHz, CDCl3) δ: 167.1, 162.23 (d, J=251.6 Hz), 141.4 (d, J=6.7 Hz), 140.0, 134.4, 131.5, 130.9 (d, J=7.7 Hz), 123.6, 123.1 (d, J=3.3 Hz), 120.4, 120.0, 117.7, 114.8, 90.2, 85.3, 84.1, 83.0, 78.6, 75.7, 61.6, 58.0, 56.6, 56.2, 55.4, 51.0, 49.9, 49.0, 48.6, 47.6, 44.9, 36.3, 31.8, 26.9, 26.3, 24.2, 13.6.

HR-ESI-MS m/z: [(M+H)⁺, 701.2905].

Example 8 Preparation of Compound 8 with Lappaconitine and 1-Naphthalenesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 150 mg of 1-naphthalenesulfonyl chloride was introduced under an ice bath. The reaction mixture was reacted at 5° C., where the reaction was monitored by thin-layer chromatography. After reacted for 19 h, the reaction mixture was purified by column chromatography to obtain 108 mg of a yellow-white foamy solid as a target compound 8 C₄₀H₄₈N₂O₉S (66.7% yield), which was structurally shown as follows:

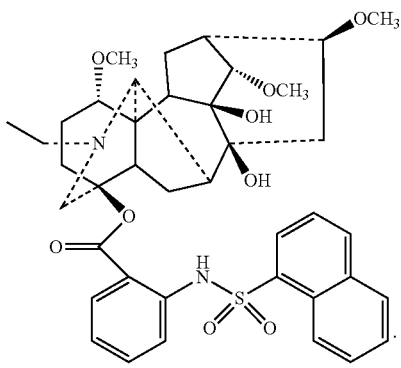

8

The target compound 8 was characterized as follows.

¹H-NMR (400 MHz, CDCl₃) δ: 11.19 (s, 1H), 8.68 (d, J=8.6 Hz, 1H), 8.32 (dd, J=7.4, 1.4 Hz, 1H), 8.00 (d, J=8.2 Hz, 1H), 7.87 (dd, J=8.2, 1.4 Hz, 1H), 7.70 (dd, J=8.0, 1.8 Hz, 1H), 7.64 (ddd, J=8.5, 6.9, 1.4 Hz, 1H), 7.56 (td, J=8.4, 1.2 Hz, 2H), 7.48 (t, J=7.8 Hz, 1H), 7.32 (ddd, J=8.6, 7.4, 1.8 Hz, 1H), 6.91-6.85 (m, 1H), 3.54 (d, J=11.6 Hz, 2H), 3.43 (d, J=4.0 Hz, 1H), 3.40 (s, 3H), 3.31 (s, 3H), 3.30 (s, 3H), 3.15 (dd, J=10.2, 7.2 Hz, 1H), 2.98 (s, 1H), 2.62-2.47 (m, 5H), 2.37 (m, 3H), 2.26 (d, J=7.4 Hz, 2H), 2.10-1.92 (m, 5H), 1.65-1.55 (m, 1H), 1.44-1.37 (m, 1H), 1.14 (t, J=7.2 Hz, 3H).

¹³C-NMR (100 MHz, CDCl₃) δ: 167.2, 140.6, 134.8, 134.3, 134.3, 134.3, 131.4, 130.4, 129.1, 128.4, 128.1, 127.0, 124.6, 124.0, 122.5, 118.2, 116.4, 90.2, 85.0, 84.2, 83.0, 78.7, 75.7, 61.6, 58.1, 56.7, 56.3, 55.4, 51.1, 50.0, 49.1, 48.7, 47.6, 45.0, 36.4, 31.7, 26.9, 26.3, 24.2, 13.7.

HR-ESI-MS m/z: [(M+H)$^+$, 733.3260].

Example 9 Preparation of Compound 9 with Lappaconitine and Benzylsulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 126.5 mg of benzylsulfonyl chloride was introduced under an ice bath. The reaction mixture was reacted at 20° C., where the reaction was monitored by thin-layer chromatography. After reacted for 4 h, the reaction mixture was subjected to rotary evaporation, and purified by column chromatography to obtain 86 mg of a milky white foamy solid as a target compound 9 $C_{37}H_{48}N_2O_9S$ (55.8% yield), which was structurally shown as follows:

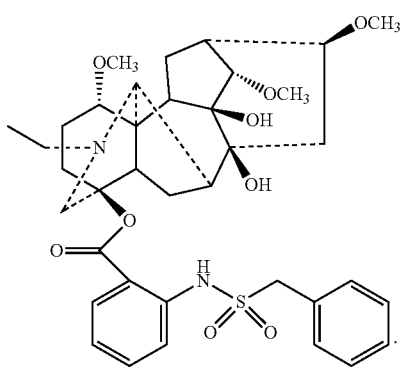

The target compound 9 was characterized as follows.

$^1$H-NMR (400 MHz, CDCl$_3$) δ: 10.42 (s, 1H), 7.90 (dd, J=8.0, 1.6 Hz, 1H), 7.67 (dd, J=8.4, 1.2 Hz, 1H), 7.46 (ddd, J=8.6, 7.4, 1.8 Hz, 1H), 7.27 (m, 2H), 7.26-7.23 (m, 1H), 7.13 (dt, J=6.6, 1.6 Hz, 2H), 7.04 (ddd, J=8.2, 7.4, 1.2 Hz, 1H), 4.38 (s, 2H), 3.55 (s, 1H), 3.47 (d, J=11.6 Hz, 1H), 3.44 (dd, J=4.9, 1.0 Hz, 1H), 3.41 (s, 3H), 3.31 (s, 3H), 3.28 (s, 3H), 3.16 (dd, J=10.2, 7.0 Hz, 1H), 2.99 (s, 1H), 2.69 (dd, J=15.2, 7.4 Hz, 1H), 2.60-2.46 (m, 4H), 2.45-2.35 (m, 3H), 2.30 (t, J=3.6 Hz, 2H), 2.16 (d, J=8.0 Hz, 2H), 2.11-1.95 (m, 3H), 1.67 (m, 1H), 1.53 (m, 1H), 1.10 (t, J=7.2 Hz, 3H).

$^{13}$C-NMR (100 MHz, CDCl$_3$) δ: 166.9, 141.4, 134.7, 131.8, 130.7×2, 129.0, 128.8×2, 128.4, 122.6, 117.5, 116.0, 90.3, 85.1, 84.2, 83.0, 78.7, 75.8, 61.7, 58.1, 56.7, 56.3, 55.4, 51.1, 49.9, 49.1, 48.8, 47.7, 45.0, 36.4, 31.9, 30.3, 26.9, 26.3, 24.3, 13.7.

HR-ESI-MS m/z: [(M+H)$^+$, 697.3236].

Example 10 Preparation of compound 10 with lappaconitine and 5-dimethylamino-1-naphthalenesulfonyl chloride 120 mg of N-deacetyl lappaconitine was added into a 5 mL round-bottom flask, and dissolved with 2 mL of dry dichloromethane. 105 mg of pyridine was dropwise added under the protection of Ar, and 150 mg of 5-dimethylamino-1-naphthalenesulfonyl chloride was introduced under an ice bath. The reaction mixture was reacted at 5° C., where the reaction was monitored by thin-layer chromatography. After reacted for 19 h, the reaction mixture was purified by column chromatography to obtain 160 mg of a yellow-white foamy solid as a target compound 10 $C_{42}H_{53}N_3O_9S$ (66.7% yield), which was structurally shown as follows:

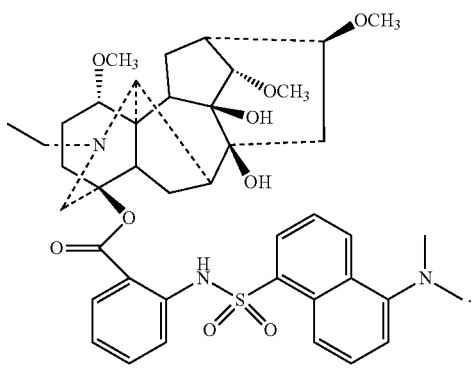

The target compound 10 was characterized as follows.

$^1$H-NMR (400 MHz, CDCl$_3$) δ: 8.49 (dd, J=8.6, 1.2 Hz, 1H), 8.34 (d, J=7.6 Hz, 2H), 7.73 (dd, J=8.0, 1.6 Hz, 1H), 7.54 (dd, J=8.8, 7.6 Hz, 2H), 7.47 (dd, J=8.6, 7.4 Hz, 1H), 7.31 (ddd, J=8.8, 7.4, 1.6 Hz, 1H), 7.13 (d, J=7.6 Hz, 1H), 6.87 (t, J=7.8 Hz, 1H), 3.59 (d, J=11.4 Hz, 1H), 3.43 (d, J=5.0 Hz, 1H), 3.40 (s, 3H), 3.31 (s, 3H), 3.30 (s, 3H), 3.16 (dd, J=10.4, 7.0 Hz, 1H), 2.99 (s, 1H), 2.83 (s, 6H), 2.66-2.47 (m, 6H), 2.45-2.34 (m, 4H), 2.28 (d, J=7.4 Hz, 2H), 2.21-1.93 (m, 6H), 1.49-1.43 (m, 1H), 1.15 (t, J=7.2 Hz, 3H).

$^{13}$C-NMR (100 MHz, CDCl$_3$) δ: 167.2, 151.9, 140.7, 134.4, 134.2, 131.4, 131.0, 130.4, 129.9, 129.6, 128.5, 123.0, 122.2, 119.0, 117.8, 116.2, 115.3, 90.2, 84.9, 84.2, 83.0, 78.6, 75.7, 61.6, 58.0, 56.7, 56.2, 55.4, 51.0, 49.9, 49.1, 48.7, 47.6, 45.5×2, 44.9, 36.3, 31.7, 26.9, 26.3, 24.2, 13.7.

HR-ESI-MS m/z: [(M+H)$^+$, 776.3541].

Example 11 Preparation of Compound 11 by Lappaconitine and (4-Nitrophenyl) Methanesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 156 mg of (4-nitrophenyl) methanesulfonyl chloride was introduced under an ice bath. The reaction mixture was reacted at 5° C., where the reaction was monitored by thin-layer chromatography. After reacted for 2 h, the reaction mixture was purified by column chromatography to obtain 77 mg of a white foamy solid as a target compound 11 $C_{37}H_{47}N_3O_{11}S$ (47.0% yield), which was structurally shown as follows:

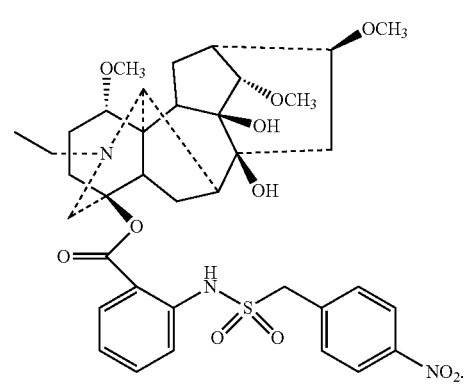

The target compound 11 was characterized as follows.

$^1$H-NMR (400 MHz, CDCl$_3$) δ: 10.52 (s, 1H), 8.13 (d, J=8.8 Hz, 2H), 7.94 (dd, J=8.0, 1.6 Hz, 1H), 7.75 (d, J=8.4 Hz, 1H), 7.51 (ddd, J=8.6, 7.3, 1.7 Hz, 1H), 7.33 (d, J=8.6 Hz, 2H), 7.10 (t, J=7.6 Hz, 1H), 4.46 (s, 2H), 3.54 (s, 1H), 3.47-3.42 (m, 2H), 3.40 (s, 3H), 3.30 (s, 3H), 3.27 (s, 3H), 3.15 (dd, J=10.2, 7.0 Hz, 1H), 2.98 (s, 1H), 2.69 (dd, J=15.2, 7.4 Hz, 1H), 2.59-2.48 (m, 2H), 2.48-2.40 (m, 3H), 2.40-2.34 (m, 2H), 2.34-2.28 (m, 2H), 2.14 (d, J=7.8 Hz, 2H), 2.08-1.93 (m, 3H), 1.72-1.62 (m, 1H), 1.50 (dd, J=15.0, 8.2 Hz, 1H), 1.07 (t, J=7.2 Hz, 3H).

$^{13}$C-NMR (100 MHz, CDCl$_3$) δ: 167.0, 148.2, 140.8, 135.7×2, 135.0, 132.1, 131.7, 123.9×2, 123.2, 117.5, 116.1, 90.2, 85.6, 84.0, 83.0, 78.7, 75.7, 61.6, 58.0, 57.1, 56.7, 56.3, 55.3, 51.1, 49.9, 49.0, 48.6, 47.7, 45.0, 36.4, 31.9, 26.8, 26.3, 24.3, 13.6.

HR-ESI-MS m/z: [(M+H)$^+$, 742.3052].

Example 12 Preparation of Compound 12 with Lappaconitine and 8-Quinoline Sulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 151 mg of 8-quinoline sulfonyl chloride was introduced under an ice bath. The reaction mixture was reacted at 5° C., where the reaction was monitored by thin-layer chromatography. After reacted for 18 h, the reaction mixture was filtered to collect a filter cake, which was separated and purified by column chromatography to obtain 122 mg of a yellow-white foamy solid as a target compound 12 C$_{39}$H$_{47}$N$_3$O$_9$S (75.3% yield), which was structurally shown as follows:

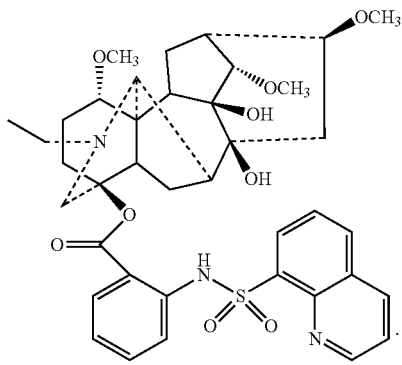

12

The target compound 12 was characterized as follows.

$^1$H-NMR (400 MHz, CDCl$_3$) δ: 11.57 (s, 1H), 9.03 (d, J=2.6 Hz, 1H), 8.53 (d, J=7.4 Hz, 1H), 8.14 (d, J=6.8 Hz, 1H), 7.97 (d, J=8.2 Hz, 1H), 7.78 (d, J=8.4 Hz, 1H), 7.72 (d, J=8.4 Hz, 1H), 7.57 (t, J=7.8 Hz, 1H), 7.46 (dd, J=8.4, 4.2 Hz, 1H), 7.31-7.25 (m, 1H), 6.83 (t, J=7.6 Hz, 1H), 3.62 (d, J=11.4 Hz, 1H), 3.54 (s, 1H), 3.45 (d, J=4.8 Hz, 1H), 3.41 (s, 3H), 3.32 (s, 6H), 3.22-3.15 (m, 1H), 3.01 (s, 1H), 2.64-2.57 (m, 4H), 2.55-2.48 (m, 2H), 2.43-2.38 (m, 4H), 2.14-1.97 (m, 5H), 1.83-1.74 (m, 1H), 1.46 (dd, J=15.2, 8.4 Hz, 1H), 1.16 (t, J=7.2 Hz, 3H).

$^{13}$C-NMR (100 MHz, CDCl$_3$) δ: 166.3, 151.3, 143.6, 140.8, 136.4, 135.8, 134.0, 134.0, 132.4, 131.4, 128.8, 125.2, 122.2, 121.9, 117.4, 116.4, 90.2, 84.5, 84.2, 83.0, 78.6, 75.7, 61.6, 58.0, 56.6, 56.2, 55.6, 51.0, 49.9, 49.1, 48.4, 47.6, 44.9, 36.3, 31.8, 26.9, 26.3, 24.1, 13.7.

HR-ESI-MS m/z: [(M+H)$^+$, 734.3103].

Example 13 Preparation of Compound 13 with Lappaconitine and 3-Methoxybenzenesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 137 mg of 3-methoxybenzenesulfonyl chloride was introduced under an ice bath. The reaction mixture was reacted at 5° C., where the reaction was monitored by thin-layer chromatography. After reacted for 1.5 h, the reaction mixture was purified by column chromatography to obtain 100 mg of a white foamy solid as a target compound 13 C$_{37}$H$_{48}$N$_2$O$_{10}$S (63.7% yield), which was structurally shown as follows:

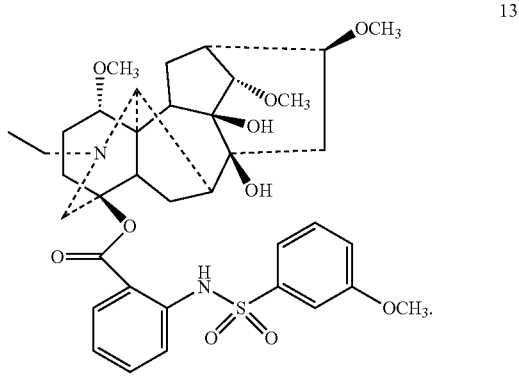

13

The target compound 13 was characterized as follows.

$^1$H-NMR (400 MHz, CDCl$_3$) δ: 10.61 (s, 1H), 7.79 (dd, J=8.0, 1.6 Hz, 1H), 7.63 (dd, J=8.4, 1.2 Hz, 1H), 7.45-7.35 (m, 2H), 7.33-7.26 (m, 2H), 7.04-6.98 (m, 2H), 3.76 (s, 3H), 3.56-3.51 (m, 2H), 3.43 (d, J=4.4 Hz, 1H), 3.40 (s, 3H), 3.30 (s, 3H), 3.28 (s, 3H), 3.16 (dd, J=10.2, 7.0 Hz, 1H), 2.98 (s, 1H), 2.63 (dd, J=15.2, 7.4 Hz, 1H), 2.59-2.53 (m, 2H), 2.52-2.45 (m, 2H), 2.42 (s, 1H), 2.40-2.35 (m, 2H), 2.29 (d, J=6.8 Hz, 2H), 2.14-1.93 (m, 5H), 1.70-1.62 (m, 1H), 1.46 (dd, J=15.0, 8.2 Hz, 1H), 1.11 (t, J=7.2 Hz, 3H).

$^{13}$C-NMR (100 MHz, CDCl$_3$) δ: 167.1, 159.8, 140.6, 140.4, 134.3, 131.4, 130.1, 123.3, 119.9, 119.6, 119.4, 117.6, 111.7, 90.2, 85.1, 84.2, 83.0, 78.7, 75.7, 61.6, 58.0, 56.7, 56.3, 55.7, 55.4, 51.0, 49.9, 49.1, 48.7, 47.6, 45.0, 36.4, 31.8, 26.9, 26.3, 24.2, 13.7.

HR-ESI-MS m/z: [(M+H)$^+$, 713.3121].

Example 14 Preparation of Compound 14 with Lappaconitine and Isopropyl Chloroformate 100 mg of N-deacetyl lappaconitine was added into a 5 mL round-bottom flask, and dissolved with 2 mL of dry tetrahydrofuran. 520 mg of isopropyl chloroformate was added under an ice bath and the protection of Ar. The reaction mixture was reacted at 60° C., where the reaction was monitored by thin-layer chromatography. After reacted for 1.5 h, the reaction mixture was subjected to rotatory evaporation, and purified by column chromatography to obtain 100 mg of a yellow foam solid as a target compound 14 C$_{34}$H$_{48}$N$_2$O$_9$ (86.2% yield), which was structurally shown as follows:

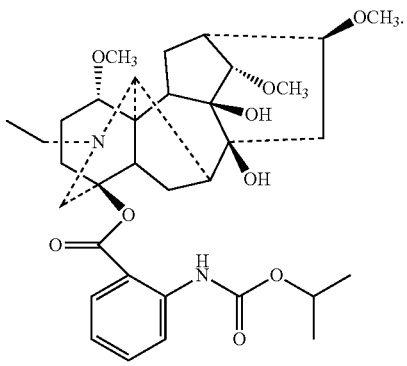

The target compound 14 was characterized as follows.

$^1$H-NMR (400 MHz, CDCl$_3$) δ: 10.39 (s, 1H), 8.42 (d, J=8.6 Hz, 1H), 7.90 (d, J=8.0 Hz, 1H), 7.47 (t, J=7.2 Hz, 1H), 6.96 (t, J=7.6 Hz, 1H), 5.04-4.97 (m, 1H), 3.60 (d, J=11.4 Hz, 1H), 3.55 (s, 1H), 3.43 (d, J=4.8 Hz, 1H), 3.40 (s, 3H), 3.31 (s, 3H), 3.29 (s, 3H), 3.18 (dd, J=10.2, 7.0 Hz, 2H), 3.00 (s, 1H), 2.69 (m, 2H), 2.60-2.46 (m, 4H), 2.44-2.34 (m, 3H), 2.29 (s, 1H), 2.18-1.98 (m, 4H), 1.79 (t, J=12.0 Hz, 1H), 1.59 (dd, J=15.0, 8.2 Hz, 1H), 1.31 (s, 3H), 1.29 (s, 3H), 1.11 (t, J=7.2 Hz, 3H).

$^{13}$C-NMR (100 MHz, CDCl$_3$) δ: 167.3, 153.4, 142.2, 134.4, 131.3, 121.3, 118.7, 115.5, 90.3, 84.5, 84.4, 83.0, 78.7, 75.7, 68.7, 61.6, 58.0, 56.6, 56.2, 55.6, 51.1, 50.0, 49.1, 48.7, 47.7, 45.0, 36.5, 32.0, 26.9, 26.3, 24.2, 22.2, 22.2, 13.7.

HR-ESI-MS m/z: [(M+H)$^+$, 629.3496].

Example 15 Preparation of Compound 15 with Lappaconitine and p-Toluenesulfonyl Chloride 100 mg of N-deacetyl lappaconitine was added into a 5 mL round-bottom flask, and dissolved with 1 mL of dry pyridine. 105 mg of p-toluenesulfonyl chloride was added under an ice bath and the protection of Ar. The reaction mixture was reacted at 50° C., where the reaction was monitored by thin-layer chromatography. After reacted for 6.5 h, the reaction mixture was subjected to rotatory evaporation, and purified by column chromatography to obtain 69 mg of a solid as a target compound 15 C$_{37}$H$_{48}$N$_2$O$_9$S, (53.7% yield), which was structurally shown as follows:

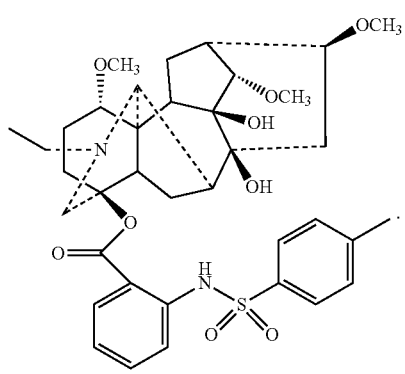

The target compound 15 was characterized as follows.

$^1$H-NMR (400 MHz, CDCl3) δ: 10.44 (s, 1H), 7.78 (d, J=8.0 Hz, 1H), 7.69 (d, J=8.3 Hz, 2H), 7.61 (d, J=8.0 Hz, 1H), 7.40 (t, J=8.6 Hz, 1H), 7.20 (d, J=8.2 Hz, 2H), 6.98 (t, J=8.2 Hz, 1H), 3.55 (d, J=11.6 Hz, 2H), 3.43 (d, J=4.6 Hz, 1H), 3.40 (s, 3H), 3.31 (s, 3H), 3.29 (s, 3H), 3.16 (dd, J=10.2, 7.2 Hz, 1H), 2.99 (s, 1H), 2.69-2.53 (m, 3H), 2.53-2.45 (m, 2H), 2.15-1.93 (m, 5H), 1.52-1.40 (m, 2H), 1.38-1.23 (m, 4H), 2.36 (s, 3H), 1.68 (t, J=15.8 Hz, 1H), 1.12 (t, J=7.2 Hz, 3H).

$^{13}$C-NMR (100 MHz, CDCl$_3$) δ: 167.16, 143.86, 140.64, 136.73, 134.27, 131.43, 129.72, 129.72, 127.38, 127.38, 123.04, 119.68, 117.40, 90.29, 85.07, 84.21, 83.03, 78.71, 75.79, 61.63, 58.07, 56.65, 56.28, 55.47, 51.12, 49.97, 49.13, 48.68, 47.70, 45.04, 36.47, 31.86, 26.90, 26.36, 24.22, 21.68, 13.66.

HR-ESI-MS m/z: [(M+H)$^+$, 697.3204].

Example 16 Preparation of Compound 16 with Lappaconitine and 2-Butenoyl Chloride 100 mg of N-deacetyl lappaconitine was added into a 5 mL round-bottom flask, and dissolved with 2 mL of dry dichloromethane. 200 l of dry pyridine was dropwise added under the protection of Ar, and 58 mg of 2-butenoyl chloride was introduced under an ice bath. The reaction mixture was reacted at 20° C., where the reaction was monitored by thin-layer chromatography. After reacted for 5 min, the reaction mixture was subjected to rotatory evaporation, and purified by column chromatography to obtain 105 mg of a light yellow solid as a target compound 16 C$_{34}$H$_{46}$N$_2$O$_8$ (64.8% yield), which was structurally shown as follows:

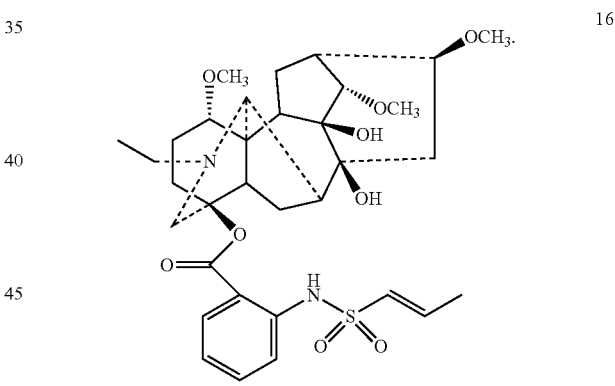

The target compound 16 was characterized as follows.

$^1$H-NMR (400 MHz, CDCl$_3$) δ: 11.15 (s, 1H), 8.76 (d, J=8.2 Hz, 1H), 7.93 (d, J=9.4 Hz, 1H), 7.50 (t, J=8.6 Hz, 1H), 7.00 (m, 2H), 6.02 (d, J=16.8 Hz, 1H), 3.58 (d, J=11.6 Hz, 1H), 3.56 (s, 1H), 3.43 (d, J=4.8 Hz, 1H), 3.40 (s, 3H), 3.31 (s, 3H), 3.29 (s, 3H), 3.18 (dd, J=10.2, 7.0 Hz, 1H), 3.00 (s, 1H), 2.73-2.62 (m, 2H), 2.60-2.47 (m, 4H), 2.43-2.35 (m, 3H), 2.29 (s, 1H), 2.19-2.05 (m, 3H), 2.01 (dd, J=14.8, 7.4 Hz, 1H), 1.92 (d, J=7.0 Hz, 3H), 1.81 (t, J=13.0 Hz, 2H), 1.59 (d, J=23.4 Hz, 1H), 1.12 (t, J=7.2 Hz, 3H).

$^{13}$C-NMR (100 MHz, CDCl$_3$) δ: 167.7, 164.6, 142.1, 141.3, 134.5, 131.3, 126.9, 122.4, 120.6, 116.1, 90.3, 84.8, 84.4, 83.1, 78.7, 75.8, 61.7, 58.1, 56.7, 56.3, 55.7, 51.1, 50.0, 49.1, 48.7, 47.8, 45.0, 36.5, 32.0, 27.0, 26.4, 24.3, 18.0, 13.7.

HR-ESI-MS m/z: [(M+H)$^+$, 611.3354].

Example 17 Preparation of Compound 17 with Lappaconitine and Methanesulfonyl Chloride 100 mg of N-deacetyl lappaconitine was added into a 5 mL round-bottom flask, and dissolved with 3 mL of dry tetrahydrofuran to dissolve. 75 mg of triethylamine was added under the protection of Ar, 98 mg of methanesulfonyl chloride was introduced under an ice bath. The reaction mixture was reacted at 20° C., where the reaction was monitored by thin-layer chromatography. After reacted for 0.5 h, the reaction mixture was subjected to rotatory evaporation, and purified by column chromatography to obtain 105 mg of a solid as a target compound 17 $C_{31}H_{44}N_2O_9S$ (91.8% yield), which was structurally shown as follows:

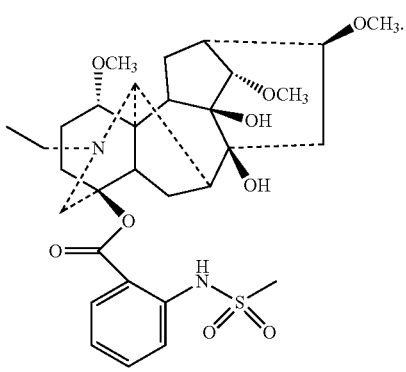

The target compound 17 was characterized as follows.

$^1$H-NMR (400 MHz, CDCl$_3$) δ: 10.51 (s, 1H), 7.93 (d, J=9.6 Hz, 1H), 7.67 (d, J=8.4 Hz, 1H), 7.50 (t, J=8.8 Hz, 1H), 7.06 (t, J=8.2 Hz, 1H), 3.58 (d, J=11.4 Hz, 1H), 3.54 (s, 1H), 3.43 (d, J=4.8 Hz, 1H), 3.40 (s, 3H), 3.30 (s, 3H), 3.28 (s, 3H), 3.17 (dd, J=10.4, 7.0 Hz, 1H), 3.05 (s, 3H), 3.00 (s, 1H), 2.73-2.61 (m, 2H), 2.59-2.44 (m, 4H), 2.37 (dd, J=7.4, 5.0 Hz, 3H), 2.30 (s, 1H), 2.17-1.93 (m, 4H), 1.82-1.72 (m, 1H), 1.56 (dd, J=15.2, 8.4 Hz, 1H), 1.41 (s, 1H), 1.11 (t, J=7.2 Hz, 3H).

$^{13}$C-NMR (100 MHz, CDCl$_3$) δ: 167.3, 141.1, 134.8, 131.9, 122.8, 118.0, 116.5, 90.3, 85.4, 84.2, 83.0, 78.7, 75.8, 61.6, 58.1, 56.6, 56.3, 55.6, 51.2, 50.0, 49.1, 48.7, 47.7, 45.0, 40.1, 36.5, 31.9, 26.9, 26.4, 24.3, 13.6.

HR-ESI-MS m/z: [(M+H)$^+$, 621.2888].

Example 18 Preparation of Compound 18 with Lappaconitine and Methylaminoformyl Chloride 150 mg of N-deacetyl lappaconitine was added into a 5 mL round-bottom flask, and dissolved with 5 mL of dichloromethane. 112 mg of triethylamine was added under the protection of Ar, and 200 mg of methylaminoformyl chloride was introduced under an ice bath. The reaction mixture was reacted at 70° C., where the reaction was monitored by thin-layer chromatography. After reacted for 6 h, the reaction mixture was subjected to rotatory evaporation, and purified by column chromatography to obtain 60 mg of a light yellow foamy solid as a target product 18 $C_{32}H_{45}N_3O_8$ (36.2% yield), which was structurally shown as follows:

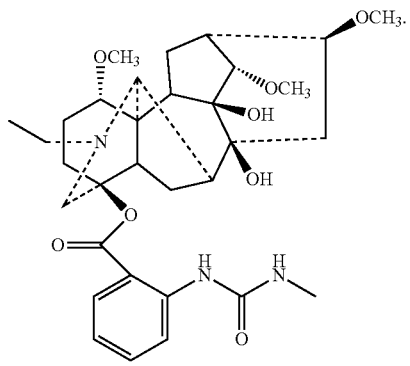

The target compound 18 was characterized as follows.

$^1$H-NMR (400 MHz, CDCl$_3$) δ: 10.36 (s, 1H), 8.48 (d, J=8.4 Hz, 1H), 7.87 (dd, J=8.0, 1.6 Hz, 1H), 7.45 (t, J=7.0 Hz, 1H), 6.90 (t, J=7.6 Hz, 1H), 3.60 (s, 1H), 3.54 (d, J=11.4 Hz, 1H), 3.47 (s, 1H), 3.44 (d, J=4.8 Hz, 1H), 3.41 (s, 3H), 3.31 (s, 3H), 3.29 (s, 3H), 3.17 (dd, J=10.2, 7.0 Hz, 1H), 3.00 (s, 1H), 2.88 (d, J=4.8 Hz, 3H), 2.67 (dd, J=15.2, 7.6 Hz, 1H), 2.60-2.46 (m, 5H), 2.44-2.34 (m, 3H), 2.32 (s, 1H) 2.32 (s, 1H), 2.16 (d, J=8.2 Hz, 1H), 2.09-1.97 (m, 3H), 1.85-1.75 (m, 1H), 1.58 (dd, J=15.2, 8.2 Hz, 1H), 1.11 (t, J=7.2 Hz, 3H).

$^{13}$C-NMR (100 MHz, CDCl$_3$) δ: 168.05, 155.97, 143.49, 134.45, 131.10, 120.65, 119.50, 115.03, 90.27, 84.45, 84.36, 83.05, 78.76, 75.76, 61.68, 58.07, 56.67, 56.27, 55.74, 51.10, 50.02, 49.13, 48.56, 47.76, 44.91, 36.49, 32.02, 27.69, 26.94, 26.39, 24.24, 13.65.

HR-ESI-MS m/z: [(M+H)$^+$, 600.3363].

Example 19 Preparation of Compound 19 with Lappaconitine and 4-Trifluoromethylbenzenesulfonyl Chloride 80 mg of N-deacetyl lappaconitine was added into a 5 mL round-bottom flask, and dissolved with 2 mL of dry dichloromethane. 200 μL of dry pyridine was dropwise added under the protection of Ar, and 143 mg of 4-trifluoromethylbenzenesulfonyl chloride was introduced under an ice bath. The reaction mixture was reacted at 20° C., where the reaction was monitored by thin-layer chromatography. After reacted for 2 h, the reaction mixture was subjected to rotatory evaporation, and purified by column chromatography to obtain 90 mg of a yellow oil product as a target compound 19 $C_{37}H_{45}F_3N_2O_9S$ (85.7% yield), which was structurally shown as follows:

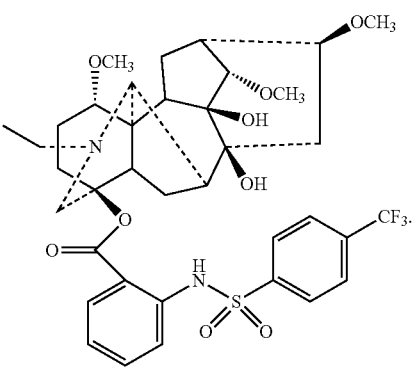

The target compound 19 was characterized as follows.

$^1$H-NMR (400 MHz, CDCl$_3$) δ: 7.93 (d, J=8.2 Hz, 2H), 7.81 (d, J=6.6 Hz, 1H), 7.66 (dd, J=17.4, 8.2 Hz, 3H), 7.45 (t, J=8.6 Hz, 1H), 7.05 (t, J=7.4 Hz, 1H), 5.29 (s, 1H), 3.51 (d, J=11.4 Hz, 2H), 3.43 (d, J=4.7 Hz, 1H), 3.40 (s, 3H), 3.30 (s, 3H), 3.29 (s, 3H), 3.16 (dd, J=10.2, 7.2 Hz, 1H), 2.98 (s, 1H), 2.64 (dd, J=15.2, 7.4 Hz, 1H), 2.58-2.44 (m, 4H), 2.44-2.34 (m, 3H), 2.14-1.95 (m, 5H), 2.31 (d, J=7.2 Hz, 1H), 1.66 (t, J=13.6 Hz, 1H), 1.46 (dd, J=15.1, 8.3 Hz, 1H), 1.42 (s, 1H), 1.36 (t, J=7.2 Hz, 3H).

$^{13}$C-NMR (100 MHz, CDCl$_3$) δ: 167.16, 143.19, 139.95, 134.85, 134.51, 131.65, 127.85, 127.9, 126.28, 126.25, 123.80, 120.02, 117.68, 90.27, 85.46, 84.15, 83.01, 78.71, 75.75, 61.60, 58.07, 56.65, 56.28, 55.44, 51.14, 49.95, 49.09, 48.61, 47.68, 45.00, 42.33, 36.48, 31.84, 26.86, 26.34, 24.23, 13.64.

HR-ESI-MS m/z: [(M+H)$^+$, 751.2958].

Example 20 Preparation of Compound 20 with Lappaconitine and 4-Methoxybenzenesulfonyl Chloride 120 mg of N-deacetyl lappaconitine was added into a 5 mL round-bottom flask, and dissolved with 2 mL of dry dichloromethane. 105 mg of pyridine was dropwise added under the protection of Ar, and 137 mg of 4-methoxybenzenesulfonyl chloride was introduced under an ice bath. The reaction mixture was reacted at 20° C., where the reaction was monitored by thin-layer chromatography. After reacted for 12 h, the reaction mixture was subjected to rotatory evaporation, and purified by column chromatography to obtain 150 mg of a milky white foamy solid as a target compound 20 C$_{37}$H$_{48}$N$_2$O$_{10}$S (93.8% yield), which was structurally shown as follows:

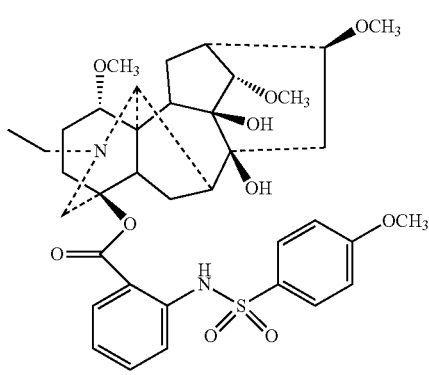

20

The target compound 20 was characterized as follows.

$^1$H-NMR (400 MHz, CDCl$_3$) δ: 10.54 (s, 1H), 7.79 (dd, J=8.0, 1.4 Hz, 1H), 7.73 (d, J=9.0 Hz, 2H), 7.62 (d, J=8.2 Hz, 1H), 7.44-7.38 (m, 1H), 6.99 (t, J=7.4 Hz, 1H), 6.87 (d, J=9.0 Hz, 2H), 3.81 (s, 3H), 3.53 (t, J=5.8 Hz, 2H), 3.43 (d, J=4.8 Hz, 1H), 3.40 (s, 3H), 3.31 (s, 3H), 3.29 (s, 3H), 3.17 (dd, J=10.2, 7.0 Hz, 1H), 2.99 (s, 1H), 2.67-2.60 (m, 1H), 2.61-2.54 (m, 2H), 2.54-2.45 (m, 2H), 2.45-2.34 (m, 3H), 2.31 (d, J=7.4 Hz, 1H), 2.26 (s, 1H), 2.20-1.91 (m, 5H), 1.75-1.66 (m, 1H), 1.47 (dd, J=14.6, 6.4 Hz, 1H), 1.12 (t, J=7.2 Hz, 3H).

$^{13}$C-NMR (100 MHz, CDCl$_3$) δ: 167.0, 163.1, 140.5, 134.2, 131.3, 131.0, 129.4, 129.4, 123.0, 119.8, 117.4, 114.2, 114.2, 90.1, 85.0, 84.0, 82.9, 78.6, 75.6, 61.5, 58.0, 56.6, 56.2, 55.6, 55.4, 51.0, 49.9, 49.0, 48.4, 47.6, 44.8, 36.3, 31.7, 26.7, 26.2, 24.1, 13.5.

Example 21 Preparation of Compound 21 with Lappaconitine and Ethyl Chloroformate 100 mg of N-deacetyl lappaconitine was added into a 5 mL round-bottom flask, and dissolved with 2 mL of dry dichloromethane. 112 mg of triethylamine was dropwise added under the protection of Ar, and 60 mg of ethyl chloroformate was introduced under an ice bath. The reaction mixture was reacted at 70° C., where the reaction was monitored by thin-layer chromatography. After reacted for 1 h, the reaction mixture was subjected to rotatory evaporation, and purified by column chromatography to obtain 102 mg of a yellow-white foamy solid as a target compound 21 C$_{33}$H$_{46}$N$_2$O$_9$ (90.3% yield), which was structurally shown as follows:

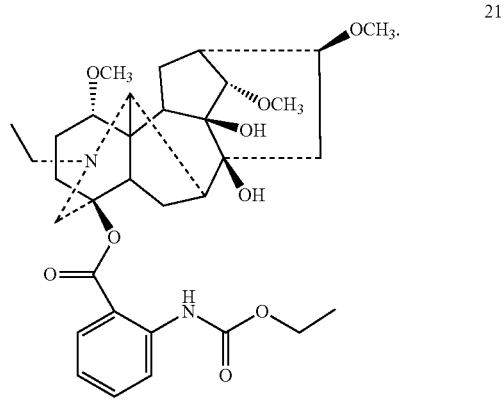

21

The target compound 21 was characterized as follows.

$^1$H-NMR (400 MHz, CDCl$_3$) δ: 10.47 (s, 1H), 8.41 (d, J=8.5 Hz, 1H), 7.91 (d, J=8.0 Hz, 1H), 7.48 (t, J=7.8 Hz, 1H), 6.97 (t, J=7.6 Hz, 1H), 4.22 (q, J=7.2 Hz, 2H), 3.61 (d, J=11.4 Hz, 1H), 3.54 (s, 1H), 3.44 (d, J=4.7 Hz, 1H), 3.41 (s, 3H), 3.31 (s, 3H), 3.29 (s, 3H), 3.18 (dd, J=10.2, 7.2 Hz, 1H), 3.00 (s, 1H), 2.73-2.64 (m, 2H), 2.61-2.46 (m, 5H), 2.40 (dd, J=15.4, 8.2 Hz, 4H), 2.20-1.91 (m, 6H), 1.84-1.73 (m, 2H), 1.60 (dd, J=15.2, 8.2 Hz, 1H), 1.12 (t, J=7.2 Hz, 3H)

$^{13}$C-NMR (100 MHz, CDCl$_3$) δ: 167.36, 153.77, 142.04, 134.40, 131.28, 121.44, 118.77, 115.56, 90.26, 84.58, 84.33, 83.03, 78.69, 75.74, 61.62, 61.20, 58.02, 56.62, 56.22, 55.59, 51.08, 49.97, 49.09, 48.74, 47.72, 44.94, 36.44, 31.94, 26.91, 26.34, 24.23, 14.65, 13.65.

HR-ESI-MS m/z: [(M+H)$^+$, 615.3331].

Example 22 Preparation of Compound 22 with Lappaconitine and 4-Phenylbenzenesulfonyl Chloride 120 mg of N-deacetyl lappaconitine was added into a 5 mL round-bottom flask, and dissolved with 2 mL of dry dichloromethane. 105 mg of pyridine was added under the protection of Ar, and 168 mg of 4-phenylbenzenesulfonyl chloride was introduced under an ice bath. The reaction mixture was reacted at 5° C., where the reaction was monitored by thin-layer chromatography. After reacted 21 h, the reaction mixture was subjected to rotatory evaporation, and purified by column chromatography to obtain 108 mg of a yellow-white foamy solid as a target compound 22 $C_{42}H_{50}N_2O_9S$ (64.3% yield), which was structurally shown as follows:

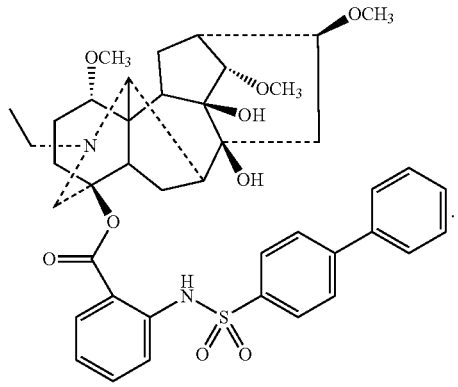

The target compound 22 was characterized as follows.

$^1$H-NMR (400 MHz, CDCl$_3$) δ: 10.66 (s, 1H), 7.86 (d, J=8.6 Hz, 2H), 7.80 (dd, J=8.0, 1.6 Hz, 1H), 7.67 (dd, J=8.4, 1.2 Hz, 1H), 7.62 (d, J=8.6 Hz, 2H), 7.57-7.53 (m, 2H), 7.44 (tdd, J=7.4, 3.0, 1.6 Hz, 3H), 7.39 (d, J=7.2 Hz, 1H), 7.02 (ddd, J=8.4, 7.4, 1.2 Hz, 1H), 3.54 (d, J=11.4 Hz, 1H), 3.52 (s, 1H), 3.42 (dd, J=4.8, 1.2 Hz, 1H), 3.40 (s, 3H), 3.30 (s, 3H), 3.28 (s, 3H), 3.14 (dd, J=10.3, 7.0 Hz, 1H), 2.96 (s, 1H), 2.63 (dd, J=15.2, 7.6 Hz, 1H), 2.59-2.32 (m, 8H), 2.30 (d, J=7.2 Hz, 1H), 2.10-1.91 (m, 5H), 1.67 (tdd, J=12.2, 5.4, 2.8, 1H), 1.46 (dd, J=15.4, 8.5 Hz, 1H), 1.10 (t, J=7.2 Hz, 3H).

$^{13}$C-NMR (100 MHz, CDCl$_3$) δ: 167.1, 145.9, 140.5, 139.2, 138.1, 134.4, 131.5, 129.2×2, 128.6, 127.8×2, 127.7×2, 127.4×2, 123.3, 120.0, 117.5, 90.2, 85.1, 84.2, 83.0, 78.7, 75.7, 61.6, 58.1, 56.7, 56.3, 55.4, 51.1, 49.9, 49.1, 48.6, 47.6, 45.0, 36.3, 31.8, 26.8, 26.3, 24.2, 13.6.

HR-ESI-MS m/z: [(M+H)$^+$, 759.3285].

Example 23 Preparation of Compound 23 from Lappaconitine and 4-Fluorobenzenesulfonyl Chloride 120 mg of N-deacetyl lappaconitine was added into a 5 mL round-bottom flask, and dissolved with 2 mL of dry dichloromethane. 105 mg of pyridine was added under the protection of Ar, and 129 mg of 4-fluorobenzenesulfonyl chloride was introduced under an ice bath. The reaction mixture was reacted at 20° C., where the reaction was monitored by thin-layer chromatography. After reacted for 2 h, the reaction mixture was subjected to rotatory evaporation, and purified by column chromatography to obtain 135 mg of a light yellow foamy solid as a target compound 23 $C_{36}H_{45}FN_2O_9S$ (87.1% yield), which was structurally shown as follows:

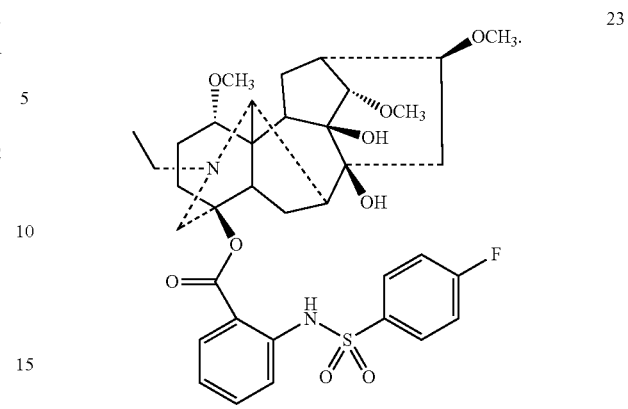

The target compound 23 was characterized as follows.

$^1$H-NMR (400 MHz, CDCl$_3$) δ: 10.35 (s, 1H), 7.81 (m, 3H), 7.62 (d, J=7.8 Hz, 1H), 7.43 (t, J=8.6 Hz, 1H), 7.08 (t, J=8.6 Hz, 2H), 7.02 (t, J=8.2 Hz, 1H), 3.53 (s, 1H), 3.50 (s, 1H), 3.43 (d, J=4.8 Hz, 1H), 3.40 (s, 3H), 3.31 (s, 3H), 3.29 (s, 3H), 3.17 (dd, J=10.2, 7.2 Hz, 1H), 2.99 (s, 1H), 2.63 (dd, J=15.2, 7.4 Hz, 1H), 2.59-2.45 (m, 4H), 2.44-2.35 (m, 3H), 2.32 (d, J=7.2 Hz, 1H), 2.27 (s, 1H), 2.15-1.92 (m, 5H), 1.76-1.66 (m, 1H), 1.46 (dd, J=15.2, 8.2 Hz, 1H), 1.12 (t, J=7.2 Hz, 3H).

$^{13}$C-NMR (100 MHz, CDCl$_3$) δ: 167.1, 165.3 (d, J=255.0 Hz), 140.3, 135.7, 134.4, 131.6, 130.1, 130.0, 123.5, 120.1, 117.6, 116.5, 116.2, 90.3, 85.3, 84.2, 83.0, 78.7, 75.8, 61.6, 58.1, 56.7, 56.3, 55.5, 51.1, 50.0, 49.1, 48.5, 47.7, 45.0, 36.5, 31.8, 26.9, 26.4, 24.2, 13.6.

HR-ESI-MS m/z: [(M+H)$^+$, 701.2905].

Example 24 Preparation of Compound 24 with Lappaconitine and Allyl Chloroformate 105 mg of N-deacetyl lappaconitine was added into a 5 mL round-bottom flask, and dissolved with 5 mL of dry toluene. 112 mg of triethylamine was added under the protection of Ar, and 67 mg of allyl chloroformate was added under an ice bath. The reaction mixture was reacted at 80° C., where the reaction was monitored by thin-layer chromatography. After reacted for 2.5 h, the reaction mixture was subjected to rotatory evaporation, and purified by column chromatography to obtain 115 mg of a white foamy solid as a target compound 24 $C_{34}H_{46}N_2O_9$ (95.0% yield), which was structurally shown as follows:

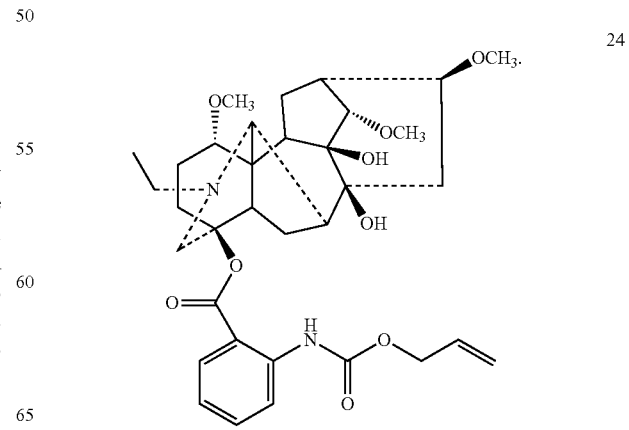

The target compound 24 was characterized as follows.

¹H-NMR (400 MHz, CDCl₃) δ: 10.57 (s, 1H), 8.40 (d, J=8.4 Hz, 1H), 7.91 (dd, J=8.0, 1.4 Hz, 1H), 7.49 (t, J=7.2 Hz, 1H), 6.98 (t, J=7.4 Hz, 1H), 6.07-5.90 (m, 1H), 5.37 (dd, J=17.2, 1.4 Hz, 1H), 5.25 (d, J=10.4 Hz, 1H), 4.66 (d, J=5.8 Hz, 2H), 3.61 (d, J=11.4 Hz, 1H), 3.54 (s, 1H), 3.44 (d, J=4.8 Hz, 1H), 3.41 (s, 3H), 3.31 (s, 3H), 3.29 (s, 3H), 3.18 (dd, J=10.2, 7.0 Hz, 1H), 3.00 (s, 1H), 2.73-2.65 (m, 2H), 2.60-2.46 (m, 4H), 2.44-2.33 (m, 3H), 2.27 (s, 1H), 2.15 (d, J=8.0 Hz, 2H), 2.09 (dd, J=12.5, 4.5 Hz, 1H), 2.01 (dd, J=14.8, 7.4 Hz, 2H), 1.83-1.73 (m, 1H), 1.60 (dd, J=15.2, 8.2 Hz, 1H), 1.11 (t, J=7.2 Hz, 3H). 13C-NMR (100 MHz, CDCl3) δ: 167.4, 153.4, 141.9, 134.4, 132.7, 131.3, 121.6, 118.8, 118.3, 115.7, 90.3, 84.7, 84.4, 83.1, 78.7, 75.8, 65.9, 61.7, 58.1, 56.7, 56.3, 55.6, 51.1, 50.0, 49.1, 48.8, 47.7, 45.0, 36.5, 32.0, 26.9, 26.4, 24.3, 13.7.

HR-ESI-MS m/z: [(M+H)⁺, 627.3347].

Example 25 Preparation of Compound 25 with Lappaconitine and 4-Chlorobenzenesulfonyl Chloride 150 mg of N-deacetyl lappaconitine was added into a 5 mL round-bottom flask, and dissolved with 2 mL of dichloromethane. 112 mg of triethylamine was added under the protection of Ar, and 116 mg of 4-chlorobenzenesulfonyl chloride was introduced under an ice bath. The reaction mixture was reacted at 20° C., where the reaction was monitored by thin-layer chromatography. After reacted for 3 h, the reaction mixture was subjected to rotatory evaporation, and purified by column chromatography to obtain 166 mg of a light yellow foamy solid as a target compound 25 $C_{36}H_{45}C_1N_2O_9S$ (83.8% yield), which was structurally shown as follows:

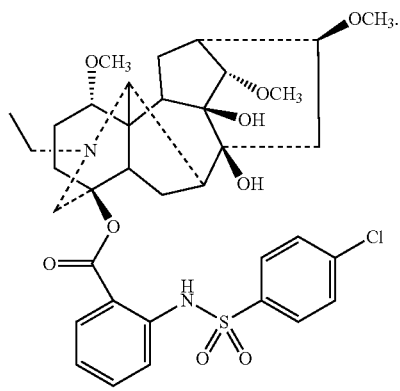

25

The target compound 25 was characterized as follows.

¹H-NMR (400 MHz, CDCl₃) δ: 10.36 (s, 1H), 7.80 (dd, J=8.0, 1.4 Hz, 1H), 7.72 (d, J=8.8 Hz, 2H), 7.62 (d, J=8.0 Hz, 1H), 7.46-7.41 (m, 1H), 7.38 (d, J=8.8 Hz, 2H), 7.04 (t, J=7.6 Hz, 1H), 3.53 (d, J=3.8 Hz, 1H), 3.49 (s, 1H), 3.43 (d, J=4.8 Hz, 2H), 3.40 (s, 3H), 3.31 (s, 3H), 3.29 (s, 3H), 3.17 (dd, J=10.2, 7.2 Hz, 1H), 2.99 (s, 1H), 2.64 (dd, J=15.2, 7.4 Hz, 1H), 2.59-2.45 (m, 4H), 2.43-2.35 (m, 3H), 2.32 (d, J=7.2 Hz, 1H), 2.26 (s, 1H), 2.13 (d, J=8.2 Hz, 1H), 2.10-2.06 (m, 1H), 2.04-1.92 (m, 2H), 1.71 (ddd, J=15.4, 9.2, 3.8, 1H), 1.46 (dd, J=15.0, 8.2 Hz, 1H), 1.12 (t, J=7.2 Hz, 3H).

¹³C-NMR (100 MHz, CDCl₃) δ: 167.0, 140.0, 139.4, 137.9, 134.3, 131.5, 129.3, 129.3, 128.7, 128.7, 123.6, 120.1, 117.6, 90.1, 85.1, 83.9, 82.9, 78.6, 75.6, 61.5, 57.9, 56.6, 56.2, 55.4, 51.0, 49.9, 49.0, 48.2, 47.6, 44.8, 36.3, 31.6, 26.6, 26.2, 24.1, 13.5.

HR-ESI-MS m/z: [(M+H)⁺, 717.2727].

Example 26 Preparation of Compound 26 with Lappaconitine and 4-Bromobenzenesulfonyl Chloride 120 mg of N-deacetyl lappaconitine was added into a 5 mL round-bottom flask, and dissolved with 2 mL of dichloromethane. 112 mg of triethylamine was added under the protection of Ar, and 141 mg of 4-bromobenzenesulfonyl chloride was introduced under an ice bath. The reaction mixture was reacted at 60° C., where the reaction was monitored by thin-layer chromatography. After reacted for 4 h, the reaction mixture was subjected to rotatory evaporation, and purified by column chromatography to obtain 65 mg of a light yellow foamy solid as a target compound 26 $C_{36}H_{45}BrN_2O_9S$ (38.7% yield), which was structurally shown as follows:

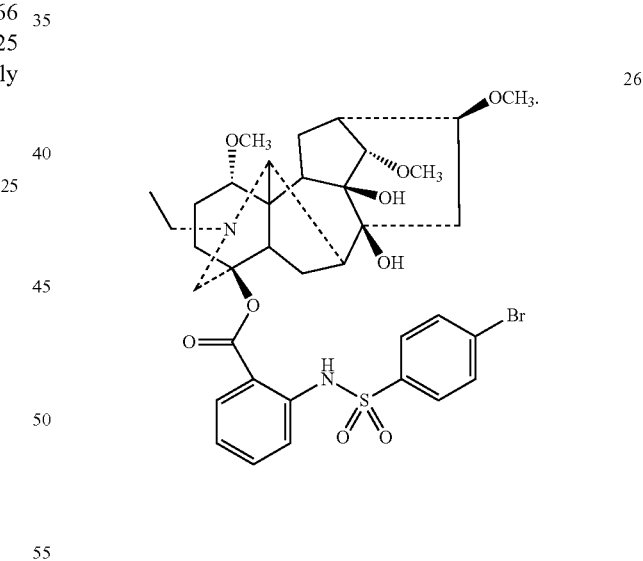

26

The target compound 26 was characterized as follows.

¹H-NMR (400 MHz, CDCl3) δ: 7.81 (dd, J=8.0, 1.4 Hz, 1H), 7.64 (m, 3H), 7.55 (d, J=8.7 Hz, 2H), 7.48-7.40 (m, 1H), 7.04 (t, J=8.2 Hz, 1H), 3.53 (d, J=2.8 Hz, 1H), 3.50 (s, 1H), 3.43 (d, J=4.8 Hz, 1H), 3.41 (s, 3H), 3.31 (s, 3H), 3.30 (s, 3H), 3.17 (dd, J=10.2, 7.0 Hz, 1H), 2.99 (s, 1H), 2.64 (dd, J=15.2, 7.4 Hz, 1H), 2.59-2.46 (m, 4H), 2.43-2.35 (m, 3H), 2.32 (d, J=7.2 Hz, 1H), 2.26 (s, 1H), 2.16-1.96 (m, 5H), 1.75-1.65 (m, 1H), 1.46 (dd, J=15.0, 8.3 Hz, 1H), 1.12 (t, J=7.2 Hz, 3H).

$^{13}$C-NMR (100 MHz, CDCl3) δ: 167.1, 140.1, 138.6, 134.4, 132.4, 132.4, 131.6, 128.8, 128.8, 128.1, 123.7, 120.2, 117.7, 90.2, 85.1, 84.0, 83.0, 78.6, 75.7, 61.6, 58.1, 56.7, 56.3, 55.5, 51.1, 49.9, 49.2, 48.2, 47.7, 44.9, 36.4, 31.6, 26.7, 26.3, 24.2, 13.5.

ESI-MS m/z: [(M+H)$^+$, 763.2000].

Example 27 Preparation of Compound 27 with Lappaconitine and Ethanesulfonyl Chloride 100 mg of N-deacetyl lappaconitine was dissolved into a 5 mL round-bottom flask, and dissolved with 5 mL of dichloromethane. 112 mg of triethylamine was added under the protection of Ar, and 71 mg of ethylsulfonyl chloride was introduced under an ice bath. The reaction mixture was reacted at 20° C., where the reaction was monitored by thin-layer chromatography. After reacted for 5 min, the reaction mixture was subjected to rotary evaporation, and purified by column chromatography to obtain 77 mg of a light yellow foamy solid as a target product 27 $C_{32}H_{46}N_2O_9S$ (65.8% yield), which was structurally shown as follows:

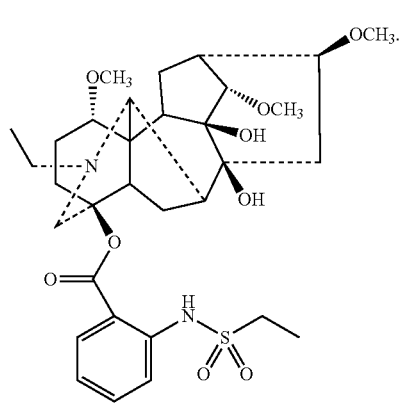

27

The target compound 27 was characterized as follows.

$^1$H-NMR (400 MHz, CDCl$_3$) δ: 10.36 (s, 1H), 7.93 (dd, J=8.0, 1.6 Hz, 1H), 7.71 (d, J=8.0 Hz, 1H), 7.54-7.44 (m, 1H), 7.05 (t, J=7.6 Hz, 1H), 3.59 (d, J=11.4 Hz, 1H), 3.53 (s, 1H), 3.44 (d, J=4.8 Hz, 2H), 3.41 (s, 3H), 3.31 (s, 3H), 3.29 (s, 3H), 3.21-3.12 (m, 3H), 3.00 (s, 1H), 2.73-2.62 (m, 2H), 2.60-2.46 (m, 4H), 2.45-2.34 (m, 3H), 2.27 (s, 1H), 2.15 (d, J=8.0 Hz, 1H), 2.09-2.07 (m, 1H), 2.04-1.95 (m, 2H), 1.78 (t, J=12.0 Hz, 1H), 1.57 (dd, J=15.0, 8.4 Hz, 1H), 1.34 (t, J=7.4 Hz, 3H), 1.11 (t, J=7.2 Hz, 3H).

$^{13}$C-NMR (100 MHz, CDCl$_3$) δ: 167.3, 141.2, 134.7, 131.8, 122.6, 117.9, 116.3, 90.2, 85.2, 84.1, 83.0, 78.6, 75.7, 61.6, 58.0, 56.6, 56.2, 55.5, 51.1, 49.9, 49.1, 48.4, 47.7, 46.5, 44.9, 36.4, 31.8, 27.0, 26.3, 24.2, 13.5, 8.2.

HR-ESI-MS m/z: [(M+H)$^+$, 635.3107].

Example 28 Preparation of Compound 28 with Lappaconitine and Phenyl Chloroformate 115 mg of N-deacetyl lappaconitine was added into a 5 mL round-bottom flask, and dissolved with 5 mL of dry toluene. 87 mg of phenyl chloroformate was introduced under an ice bath and the protection of Ar. The reaction mixture was reacted at 40° C., where the reaction was monitored by thin layer chromatography. After reacted for 0.5 h, the reaction mixture was washed with methanol to obtain a solid, and the solid was purified by column chromatography to obtain 53 mg of a light yellow solid as a target compound 28 $C_{37}H_{46}N_2O_9$ (37.9% yield), which was structurally shown as follows:

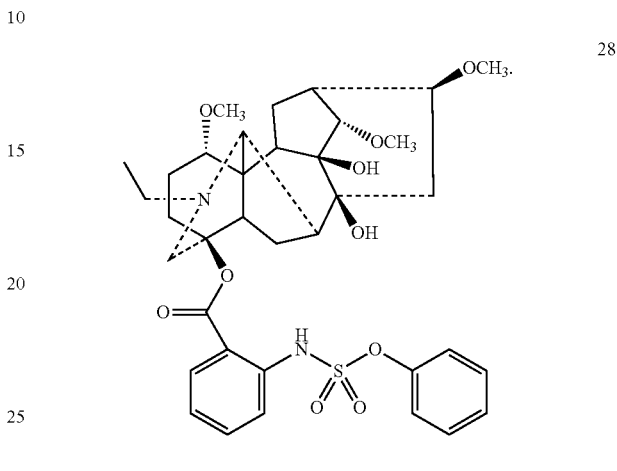

28

The target compound 28 was characterized as follows.

$^1$H-NMR (400 MHz, CDCl$_3$) δ: 10.94 (s, 1H), 8.42 (d, J=8.4 Hz, 1H), 7.96 (d, J=8.0 Hz, 1H), 7.51 (t, J=7.4 Hz, 1H), 7.39 (t, J=8.0 Hz, 2H), 7.21 (t, J=7.0 Hz, 3H), 7.04 (t, J=7.6 Hz, 1H), 3.64 (d, J=11.4 Hz, 1H), 3.55 (s, 1H), 3.45 (d, J=4.6 Hz, 1H), 3.41 (s, 3H), 3.32 (s, 3H), 3.30 (s, 3H), 3.20 (dd, J=10.2, 7.2 Hz, 1H), 3.02 (s, 1H), 2.76-2.68 (m, 2H), 2.61-2.47 (m, 4H), 2.45-2.36 (m, 3H), 2.28 (s, 1H), 2.19-1.94 (m, 5H), 1.88-1.77 (m, 1H), 1.62 (dd, J=15.2, 8.2 Hz, 1H), 1.13 (t, J=7.2 Hz, 3H).

$^{13}$C-NMR (100 MHz, CDCl$_3$) δ: 167.5, 151.9, 150.8, 141.5, 134.6, 131.4, 129.5, 129.5, 125.7, 122.2, 121.9, 121.9, 119.0, 116.1, 90.3, 84.9, 84.4, 83.1, 78.7, 75.8, 61.7, 58.1, 56.7, 56.3, 55.7, 51.2, 50.0, 49.2, 48.8, 47.8, 45.0, 36.5, 27.1, 27.0, 26.4, 24.3, 13.7.

HR-ESI-MS m/z: [(M+H)$^+$, 663.3340].

Example 29 Preparation of Compound 29 with Lappaconitine and 2-Thenoyl Chloride 120 mg of N-deacetyl lappaconitine was added into a 5 mL round-bottom flask, and dissolved with 2 mL of dry dichloromethane. 107 μL of pyridine was dropwise added under the protection of Ar, and 121 mg of 2-thenoyl chloride was introduced under an ice bath. The reaction mixture was reacted at 5° C., and the reaction was monitored by thin-layer chromatography. After reacted for 1.5 h, the reaction mixture was purified by column chromatography to obtain 80 mg of a yellow-white foamy solid as a target compound 29 $C_{34}H_{44}N_2O_9S_2$ (52.6% yield), which was structurally shown as follows:

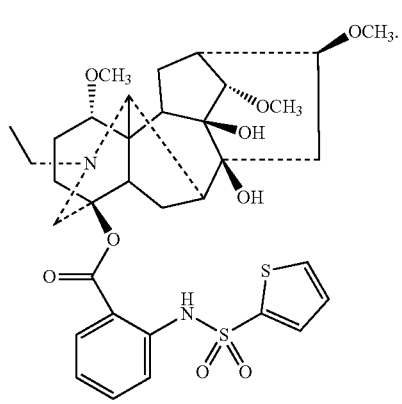

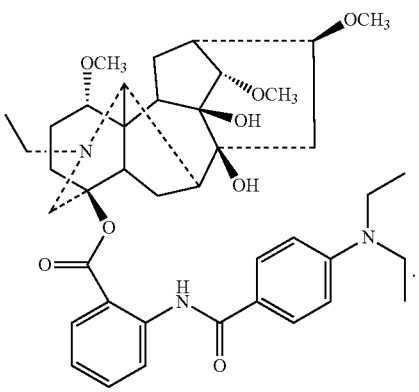

The target compound 29 was characterized as follows.

$^1$H-NMR (400 MHz, CDCl$_3$) δ: 7.82 (dd, J=8.0, 1.6 Hz, 1H), 7.71 (dd, J=8.4, 1.2 Hz, 1H), 7.54 (dd, J=3.8, 1.4 Hz, 1H), 7.51-7.43 (m, 2H), 7.05 (td, J=7.6, 1.2 Hz, 1H), 6.98 (dd, J=5.0, 3.8 Hz, 1H), 3.54 (d, J=11.6 Hz, 2H), 3.43 (d, J=5.0 Hz, 1H), 3.40 (s, 3H), 3.31 (s, 3H), 3.29 (s, 3H), 3.16 (dd, J=10.2, 7.2 Hz, 1H), 2.98 (s, 1H), 2.68-2.55 (m, 3H), 2.53-2.35 (m, 6H), 2.32 (d, J=7.4 Hz, 1H), 2.16-1.94 (m, 5H), 1.76-1.65 (m, 1H), 1.47 (dd, J=15.0, 8.2 Hz, 1H), 1.11 (t, J=7.2 Hz, 3H).

$^{13}$C-NMR (100 MHz, CDCl$_3$) δ: 167.1, 140.2, 140.1, 134.4, 132.8, 132.5, 131.4, 127.3, 123.6, 120.1, 117.7, 90.2, 85.1, 84.1, 83.0, 78.6, 75.7, 61.6, 58.1, 56.7, 56.3, 55.5, 51.1, 49.9, 49.2, 48.4, 47.6, 45.0, 36.4, 31.7, 26.7, 26.3, 24.2, 13.6.

HR-ESI-MS m/z: [(M+H)$^+$, 689.2659].

Example 30 Preparation of Compound 30 with Lappaconitine and 4-Diethylaminobenzoic Acid 172 mg of 4-diethylaminobenzoic acid was added into a 25 mL dry round-bottom flask, and dissolved by 10 mL of dry dichloromethane. A few drops of dimethylformamide were added, and 375 mg of oxalyl chloride was added under an ice bath. The reaction mixture was reacted at room temperature for 2 h to obtain 4-diethylaminobenzoyl chloride. 102 mg of N-deacetyl lappaconitine was added in another 25 mL round-bottom flask, and dissolved with 10 mL of dry dichloromethane. 105 μL of dry pyridine was dropwise added under the protection of Ar, and the prepared 4-diethylaminobenzoyl chloride was slowly dropwise added. The reaction mixture was reacted at 35° C., where the reaction was monitored by thin-layer chromatography. After reacted for 14 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 96 mg of a light yellow foamy solid as a target compound 30 C$_{41}$H$_{55}$N$_3$O$_8$ (71.2% yield), which was structurally shown as follows:

The target compound 30 was characterized as follows.

$^1$H-NMR (400 MHz, CDCl$_3$) δ: 11.81 (s, 1H), 8.89 (dd, J=8.6, 1.2 Hz, 1H), 7.95 (dd, J=8.0, 1.8 Hz, 1H), 7.91 (d, J=9.0 Hz, 2H), 7.52 (ddd, J=8.8, 7.2, 1.8 Hz, 1H), 7.01 (t, J=7.0 Hz, 1H), 6.72 (d, J=9.0 Hz, 2H), 3.62 (d, J=11.4 Hz, 1H), 3.56 (s, 1H), 3.46 (d, J=3.6 Hz, 1H), 3.44 (d, J=7.0 Hz, 3H), 3.41 (s, 3H), 3.32 (s, 3H), 3.30 (s, 3H), 3.21 (dd, J=10.4, 7.0 Hz, 1H), 3.02 (s, 1H), 2.74-2.65 (m, 2H), 2.61-2.48 (m, 4H), 2.47-2.36 (m, 3H), 2.32 (d, J=12.8 Hz, 1H), 2.26 (s, 1H), 2.20-2.09 (m, 3H), 2.06-1.94 (m, 2H), 1.85 (t, J=13.8 Hz, 1H), 1.67-1.62 (m, 1H), 1.22 (t, J=7.0 Hz, 6H), 1.14 (t, J=7.2 Hz, 3H).

$^{13}$C-NMR (100 MHz, CDCl$_3$) δ: 167.80, 165.85, 150.40, 142.72, 134.38, 131.18, 131.2, 129.45, 121.74, 120.72, 120.39, 115.91, 110.71, 110.7, 90.21, 84.40, 84.30, 83.01, 78.65, 75.66, 61.53, 57.98, 56.59, 56.18, 55.63, 51.04, 49.93, 49.05, 48.55, 47.68, 44.84, 44.52, 44.5, 36.41, 31.6, 26.97, 26.91, 26.33, 13.64, 12.63, 12.6.

HR-ESI-MS m/z: [(M+H)$^+$, 718.4086].

Example 31 Preparation of Compound 31 with Lappaconitine and 4-Ethoxybenzoyl Chloride 99 mg of N-deacetyl lappaconitine was added into a 25 ml round-bottom flask, and dissolved with 5 mL of dry dichloromethane. 105 μL of dry pyridine was dropwise added under the protection of Ar, and 102 mg of 4-ethoxybenzoyl chloride was slowly dropwise added. The reaction mixture was reacted at 20° C., where the reaction was monitored by thin-layer chromatography. After reacted for 2 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 90 mg of a light yellow foamy solid as a target compound 30 C$_{39}$H$_{50}$N$_2$O$_9$ (70.9% yield), which was structurally shown as follows:

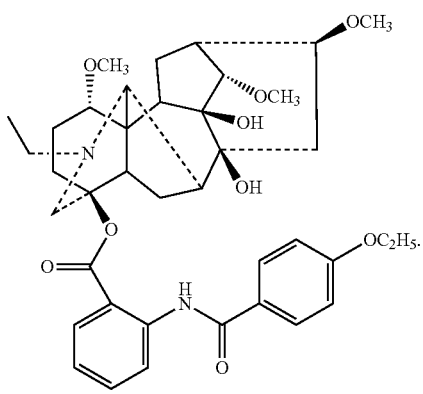

31

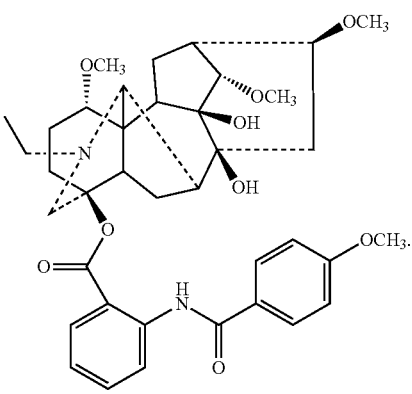

32

The target compound 31 was characterized as follows.

$^1$H-NMR (400 MHz, CDCl$_3$) δ: 11.94 (s, 1H), 8.87 (d, J=8.4 Hz, 1H), 8.10-7.89 (m, 3H), 7.55 (ddd, J=8.8, 7.4, 1.8 Hz, 1H), 7.05 (t, J=7.4 Hz, 1H), 7.00 (d, J=8.8 Hz, 2H), 4.11 (q, J=7.0 Hz, 2H), 3.60 (d, J=11.4 Hz, 1H), 3.56 (s, 1H), 3.45 (d, J=4.8 Hz, 1H), 3.41 (s, 3H), 3.32 (s, 3H), 3.30 (s, 3H), 3.21 (dd, J=10.4, 7.0 Hz, 1H), 3.02 (s, 1H), 2.70 (dd, J=15.0, 8.2 Hz, 2H), 2.60-2.48 (m, 4H), 2.45 (d, J=7.6 Hz, 1H), 2.40-2.36 (m, 2H), 2.28 (s, 1H), 2.20-2.07 (m, 3H), 2.06-1.96 (m, 2H), 1.86 (t, J=12.6 Hz, 1H), 1.65-1.59 (m, 1H), 1.45 (t, J=7.0 Hz, 3H), 1.13 (t, J=7.2 Hz, 3H).

$^{13}$C-NMR (100 MHz, CDCl$_3$) δ: 167.9, 165.5, 162.1, 142.3, 134.6, 131.3, 129.5, 129.5, 127.2, 122.4, 120.5, 116.3, 114.6, 114.6, 90.3, 84.7, 84.4, 83.1, 78.7, 75.8, 63.8, 61.7, 58.1, 56.7, 56.3, 55.7, 51.1, 49.9, 49.2, 48.6, 47.7, 45.0, 36.5, 31.9, 27.1, 27.0, 26.4, 24.3, 14.9.

HR-ESI-MS m/z: [(M+H)$^+$, 691.3702].

Example 32 Preparation of Compound 32 with Lappaconitine and 4-Methoxybenzoic Acid 120 mg of 4-methoxybenzoic acid was added in a 25 mL dry round-bottom flask, and dissolved with 10 mL of dry dichloromethane. A few drops of dimethylformamide was added, and 129 mg of oxalyl chloride was dropwise added under an ice bath. The reaction mixture was reacted at room temperature for 3 h to obtain 4-methoxybenzoyl chloride. 69 mg of N-deacetyl lappaconitine was added into another 25 mL round-bottom flask, and dissolved with 10 mL of dry dichloromethane. 300 μL of dry pyridine was dropwise added under the protection of Ar, and the prepared 4-methoxybenzoyl chloride was slowly dropwise added. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 33 mg of a light yellow foamy solid as a target compound 32 C$_{38}$H$_{48}$N$_2$O$_9$ (38.4% yield), which was structurally shown as follows:

The target compound 32 was characterized as follows.

$^1$H-NMR (400 MHz, CDCl$_3$) δ: 11.95 (s, 1H), 8.87 (d, J=8.4 Hz, 1H), 8.08-7.90 (m, 3H), 7.61-7.49 (m, 1H), 7.10-6.99 (m, 3H), 3.88 (s, 3H), 3.60 (d, J=11.6 Hz, 1H), 3.57 (s, 1H), 3.45 (d, J=4.8 Hz, 1H), 3.41 (s, 3H), 3.31 (s, 3H), 3.30 (s, 3H), 3.21 (dd, J=10.4, 7.0 Hz, 1H), 3.02 (s, 1H), 2.70 (dd, J=15.8, 8.4 Hz, 2H), 2.61-2.48 (m, 4H), 2.45 (d, J=7.8 Hz, 1H), 2.42-2.35 (m, 2H), 2.28 (s, 1H), 2.19-1.95 (m, 5H), 1.91-1.81 (m, 1H), 1.62 (dd, J=15.0, 8.2 Hz, 1H), 1.13 (t, J=7.2 Hz, 3H).

$^{13}$C-NMR (100 MHz, CDCl$_3$) δ: 167.9, 165.4, 162.6, 142.3, 134.6, 131.3, 129.5, 129.5, 127.4, 122.4, 122.4, 120.5, 116.2, 114.1, 90.2, 84.7, 84.3, 83.0, 78.7, 75.7, 61.6, 58.0, 56.7, 56.2, 55.7, 55.5, 51.1, 49.9, 49.1, 48.5, 47.7, 44.9, 36.4, 31.9, 27.0, 26.4, 24.2, 13.6.

HR-ESI-MS m/z: [(M+H)$^+$, 677.3514].

Example 33 Preparation of Compound 33 with Lappaconitine and Cyclopentacarboxylic Acid 116 mg of cyclopentacarboxylic acid in a 25 mL dry round-bottom flask, and dissolved with 5 mL of dry dichloromethane. A few drops of dimethylformamide was added, and 375 mg of oxalyl chloride was dropwise added under an ice bath. The reaction mixture was reacted at room temperature for 2 h to obtain cyclopentanoyl chloride. 107 mg of N-deacetyl lappaconitine was added into another 25 mL round-bottom flask, and dissolved with 10 mL of dry dichloromethane. 105 μL of dry pyridine was dropwise added under the protection of Ar, and the prepared cyclopentanoyl chloride was slowly dropwise added. The reaction mixture was reacted at 35° C., where the reaction was monitored by thin-layer chromatography. After reacted for 15 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 81 mg of a light yellow foamy solid to obtain a target compound 33 C$_{36}$H$_{50}$N$_2$O$_8$ (64.3% yield), which was structurally shown as follows:

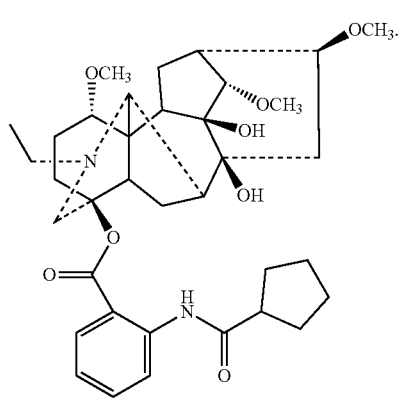

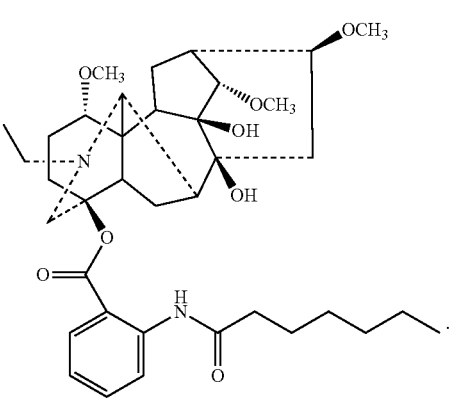

The target compound 33 was characterized as follows.

¹H-NMR (400 MHz, CDCl₃) δ: 11.10 (s, 1H), 8.71 (dd, J=8.6, 1.2 Hz, 1H), 7.92 (dd, J=8.2, 1.8 Hz, 1H), 7.49 (ddd, J=8.8, 7.4, 1.8 Hz, 1H), 7.01 (ddd, J=8.2, 7.4, 1.2 Hz, 1H), 3.58 (d, J=11.4 Hz, 1H), 3.55 (s, 1H), 3.44 (d, J=4.8 Hz, 1H), 3.41 (s, 3H), 3.31 (s, 3H), 3.30 (s, 3H), 3.19 (dd, J=10.4, 7.0 Hz, 1H), 3.01 (s, 1H), 2.78 (p, J=8.2 Hz, 1H), 2.73-2.62 (m, 2H), 2.61-2.47 (m, 4H), 2.40 (dt, J=14.4, 7.2 Hz, 3H), 2.26 (s, 1H), 2.19-2.07 (m, 3H), 2.05-1.94 (m, 3H), 1.93-1.85 (m, 2H), 1.82-1.75 (m, 2H), 1.68-1.55 (m, 5H), 1.13 (t, J=7.2 Hz, 3H).

¹³C-NMR (100 MHz, CDCl₃) δ: 175.5, 167.6, 142.0, 134.5, 131.2, 122.2, 120.4, 115.9, 90.2, 84.6, 84.3, 83.0, 78.7, 75.8, 61.7, 58.1, 56.7, 56.3, 55.6, 51.1, 49.9, 49.1, 48.7, 48.0, 47.7, 45.0, 36.4, 32.0, 30.6, 30.5, 26.9, 26.4, 26.0, 26.0, 24.2, 13.7.

HR-ESI-MS m/z: [(M+H)⁺, 639.2407].

Example 34 Preparation of Compound 34 with Lappaconitine and Heptanoyl Chloride 98 mg of N-deacetyl lappaconitine was added into a 25 mL round-bottom flask, and dissolved with 5 mL of dry dichloromethane. 105 μL of dry pyridine was dropwise added under the protection of Ar, and 77 mg of heptanoyl chloride was slowly added. The reaction mixture was reacted at 20° C., where the reaction was monitored by thin-layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 90 mg of a light yellow foamy solid as a target compound 34 C₃₇H₅₄N₂O₈ (76.3% yield), which was structurally shown as follows:

The target compound 34 was characterized as follows.

¹H-NMR (400 MHz, CDCl₃) δ: 11.05 (s, 1H), 8.69 (d, J=8.6 Hz, 1H), 7.91 (dd, J=8.0, 1.6 Hz, 1H), 7.49 (t, J=8.0 Hz, 1H), 7.01 (t, J=7.8 Hz, 1H), 3.58 (d, J=11.6 Hz, 2H), 3.44 (d, J=5.0 Hz, 1H), 3.40 (s, 3H), 3.31 (s, 3H), 3.29 (s, 3H), 3.19 (dd, J=10.4, 7.0 Hz, 1H), 3.00 (s, 1H), 2.73-2.61 (m, 2H), 2.61-2.46 (m, 4H), 2.44-2.35 (m, 5H), 2.30 (s, 1H), 2.18-1.92 (m, 5H), 1.86-1.78 (m, 1H), 1.73 (p, J=7.6 Hz, 2H), 1.59 (dd, J=15.2, 8.2 Hz, 1H), 1.24 (d, J=6.8 Hz, 6H), 1.12 (t, J=7.2 Hz, 3H), 0.89 (t, J=7.2 Hz, 3H).

¹³C-NMR (100 MHz, CDCl₃) δ: 172.4, 167.6, 141.9, 134.5, 131.2, 122.3, 120.4, 115.9, 90.3, 84.7, 84.3, 83.0, 78.7, 75.8, 61.7, 58.1, 56.7, 56.3, 55.6, 51.1, 50.0, 49.2, 48.7, 47.7, 45.0, 38.8, 36.4, 31.7, 29.0, 27.0, 26.9, 26.4, 25.6, 24.3, 22.7, 14.2, 13.7.

HR-ESI-MS m/z: [(M+H)⁺, 654.3979].

Example 35 Preparation of Compound 35 with Lappaconitine and n-Propoxybenzoic Acid 181 mg of 4-n-propoxybenzoic acid was added into a 25 mL dry round-bottom flask, and dissolved with 5 mL of dry dichloromethane. A few drops of dimethylformamide was added, and 381 mg of oxalyl chloride was dropwise added under an ice bath. The reaction mixture was reacted at room temperature for 2 h to obtain 4-n-propoxy benzoyl chloride. 89 mg of N-deacetyl lappaconitine was added to another 25 mL round-bottom flask, and dissolved with 10 mL of dry dichloromethane. 105 μL of dry pyridine was dropwise added under the protection of Ar, and the prepared 4-n-propoxy benzoyl chloride was slowly added. The reaction mixture was reacted at 35° C., where the reaction was monitored by thin-layer chromatography. After reacted for 15 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 50 mg of a light yellow foamy solid as a target compound 35 C₄₀H₅₂N₂O₉ (43.5% yield), which was structurally shown as follows:

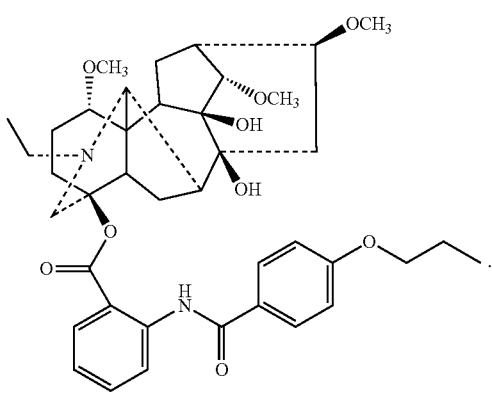

35

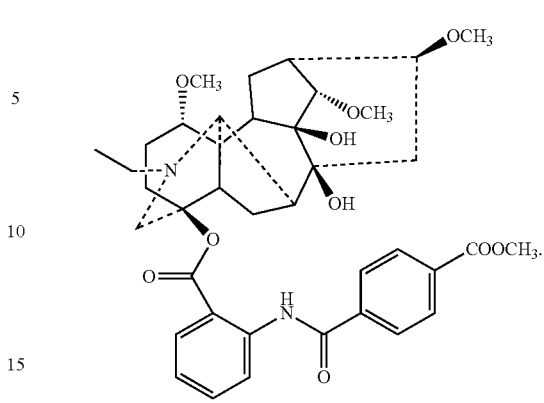

36

The target compound 35 was characterized as follows.

$^1$H-NMR (400 MHz, CDCl$_3$) δ: 11.94 (s, 1H), 8.87 (d, J=8.4 Hz, 1H), 7.98 (dd, J=8.2, 5.8 Hz, 3H), 7.55 (t, J=8.2 Hz, 1H), 7.06 (t, J=7.6 Hz, 1H), 7.01 (d, J=8.8 Hz, 2H), 4.00 (t, J=6.6 Hz, 2H), 3.61 (d, J=11.4 Hz, 1H), 3.56 (s, 1H), 3.45 (d, J=5.0 Hz, 1H), 3.41 (s, 3H), 3.31 (s, 3H), 3.30 (s, 3H), 3.21 (dd, J=10.2, 7.2 Hz, 1H), 3.02 (s, 1H), 2.73-2.64 (m, 2H), 2.60-2.48 (m, 4H), 2.45 (d, J=7.0 Hz, 1H), 2.38 (t, J=6.6 Hz, 2H), 2.27 (s, 1H), 2.20-2.07 (m, 3H), 2.06-1.97 (m, 2H), 1.84 (q, J=7.0 Hz, 2H), 1.62 (dd, J=15.2, 8.4 Hz, 2H), 1.13 (t, J=7.2 Hz, 3H), 1.06 (t, J=7.4 Hz, 3H).

$^{13}$C-NMR (100 MHz, CDCl$_3$) δ: 167.89, 165.50, 162.28, 142.30, 134.56, 131.29, 129.45, 129.4, 127.16, 122.35, 120.49, 116.24, 114.60, 114.6, 90.28, 84.72, 84.35, 83.05, 78.71, 75.77, 69.81, 61.63, 58.06, 56.68, 56.26, 55.66, 51.12, 49.94, 49.12, 48.59, 47.71, 44.98, 36.45, 31.93, 27.03, 26.39, 24.24, 22.61, 13.69, 10.61.

HR-ESI-MS m/z: [(M+H)$^+$, 705.3805].

The target compound 36 was characterized as follows.

$^1$H-NMR (400 MHz, CDCl$_3$) δ: 12.15 (s, 1H), 8.87 (dd, J=8.6, 1.4 Hz, 1H), 8.19 (dd, J=8.4, 1.8 Hz, 2H), 8.08 (d, J=8.6 Hz, 2H), 7.98 (d, J=8.0 Hz, 1H), 7.61-7.53 (m, 1H), 7.10 (t, J=7.8 Hz, 1H), 3.95 (s, 3H), 3.59 (d, J=11.6 Hz, 1H), 3.56 (s, 1H), 3.44 (d, J=4.8 Hz, 1H), 3.40 (s, 3H), 3.31 (s, 3H), 3.30 (s, 3H), 3.20 (dd, J=10.3, 7.0 Hz, 1H), 3.01 (s, 1H), 2.74-2.63 (m, 2H), 2.60-2.48 (m, 4H), 2.44 (d, J=8.0 Hz, 1H), 2.38 (dd, J=7.8, 5.0 Hz, 2H), 2.29 (s, 1H), 2.20-1.95 (m, 5H), 1.91-1.81 (m, 1H), 1.60 (dd, J=15.2, 8.4 Hz, 1H), 1.13 (t, J=7.2 Hz, 3H).

$^{13}$C-NMR (100 MHz, CDCl$_3$) δ: 167.9, 166.5, 164.9, 141.7, 139.0, 134.7, 133.1, 131.4, 130.2, 130.2, 127.6, 127.6, 123.1, 120.6, 116.5, 90.3, 85.1, 84.3, 83.1, 78.7, 75.8, 61.7, 58.1, 56.7, 56.3, 55.6, 52.5, 51.2, 49.9, 49.2, 48.6, 47.7, 45.1, 36.5, 32.0, 27.0, 26.4, 24.3, 13.7.

HR-ESI-MS m/z: [(M+H)$^+$, 705.1904].

Example 36 Preparation of Compound 36 with Lappaconitine and Methyl 4-Chloroformyl Benzoate 216 mg of N-deacetyl lappaconitine was added into a 25 mL round-bottom flask, and dissolved with 5 mL of dry dichloromethane. 600 μL of dry pyridine was dropwise added under the protection of Ar, and 238.3 mg of methyl 4-chloroformyl benzoate was introduced under an ice bath. The reaction mixture was reacted at 20° C., where the reaction was monitored by thin-layer chromatography. After reacted for 19 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 200 mg of a light yellow foamy solid as a target compound 36 C$_{39}$H$_{48}$N$_2$O$_{10}$ (71.3% yield), which was structurally shown as follows:

Example 37 Preparation of Compound 37 with Lappaconitine and Cyclohexanecarboxylic Acid Chloride 107 mg of N-deacetyl lappaconitine was added into a 25 mL round-bottom flask, and dissolved with 5 mL of dry dichloromethane. 105 μL of dry pyridine was dropwise added under the protection of Ar, and 88 mg of cyclohexanecarboxylic acid chloride was slowly dropwise added. The reaction mixture was reacted at 20° C., where the reaction was monitored by thin-layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 60 mg of a light yellow foamy solid as a target compound 37 C$_{37}$H$_{52}$N$_2$O$_8$ (46.0% yield), which was structurally shown as follows:

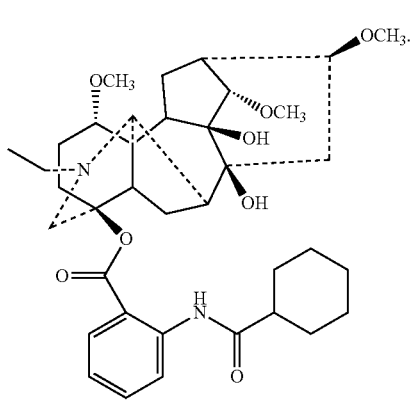

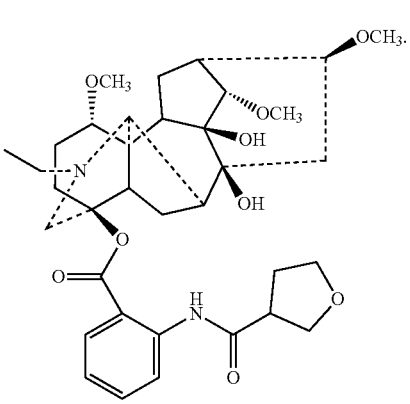

The target compound 37 was characterized as follows.

$^1$H-NMR (400 MHz, CDCl$_3$) δ: 11.06 (s, 1H), 8.71 (dd, J=8.5, 1.1 Hz, 1H), 7.92 (dd, J=8.0, 1.8 Hz, 1H), 7.48 (ddd, J=8.8, 7.4, 1.8 Hz, 1H), 7.01 (ddd, J=8.2, 7.4, 1.2 Hz, 1H), 3.58 (d, J=11.6 Hz, 1H), 3.55 (s, 1H), 3.44 (d, J=4.4 Hz, 1H), 3.41 (s, 3H), 3.32 (s, 3H), 3.30 (s, 3H), 3.20 (dd, J=10.4, 7.0 Hz, 1H), 3.01 (s, 1H), 2.73-2.60 (m, 2H), 2.60-2.47 (m, 4H), 2.43 (d, J=8.0 Hz, 1H), 2.38 (t, J=6.6 Hz, 1H), 2.31-2.25 (m, 2H), 2.18-2.07 (m, 3H), 2.03-1.96 (m, 3H), 1.87-1.80 (m, 3H), 1.73-1.48 (m, 6H), 1.32 (dd, J=23.8, 11.4 Hz, 3H), 1.13 (t, J=7.2 Hz, 3H).

$^{13}$C-NMR (100 MHz, CDCl$_3$) δ: 175.5, 167.5, 142.0, 134.4, 131.2, 122.3, 120.5, 116.1, 90.3, 84.6, 84.4, 83.0, 78.7, 75.8, 61.7, 58.1, 56.7, 56.3, 55.7, 51.1, 49.9, 49.1, 48.6, 47.7, 47.3, 45.0, 36.5, 31.9, 29.7, 29.7, 27.0, 26.4, 25.9, 25.8, 25.8, 24.2, 13.7.

HR-ESI-MS m/z: [(M+H)$^+$, 654.3873].

Example 38 Preparation of Compound 38 with Lappaconitine and 3-Tetrahydrofurancarboxylic Acid 116 mg of 3-tetrahydrofurancarboxylic acid was added into a 25 mL dry round-bottom flask, and dissolved with 10 mL of dry dichloromethane. A few drops of dimethylformamide were added, and 375 mg of oxalyl chloride was dropwise added under an ice bath. The reaction mixture was reacted at room temperature for 2 h to obtain 3-tetrahydrofuroyl chloride. 87 mg of N-deacetyl lappaconitine was added into another 25 mL round-bottom flask, and dissolved with 10 mL of dry dichloromethane. 105 μL of dry pyridine was added under the protection of Ar, and the prepared 3-tetrahydrofuroyl chloride was slowly dropwise added. The reaction mixture was reacted at 35° C., where the reaction was monitored by thin-layer chromatography. After reacted for 14 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 99 mg of a light yellow foamy solid as a target compound 38 C$_{35}$H$_{48}$N$_2$O$_9$ (96.1% yield), which was structurally shown as follows:

The target compound 38 was characterized as follows.

$^1$H-NMR (400 MHz, CDCl$_3$) δ: 11.23 (d, J=5.2 Hz, 1H), 8.67 (d, J=8.4 Hz, 1H), 7.93 (dd, J=8.0, 1.8 Hz, 1H), 7.50 (t, J=8.8 Hz, 1H), 7.09-7.00 (m, 1H), 4.10 (t, J=8.4 Hz, 1H), 4.03-3.95 (m, 2H), 3.88 (q, J=7.6 Hz, 1H), 3.60-3.54 (m, 2H), 3.44 (d, J=4.8 Hz, 1H), 3.41 (s, 3H), 3.31 (s, 3H), 3.30 (s, 3H), 3.22-3.11 (m, 2H), 3.01 (s, 1H), 2.73-2.62 (m, 2H), 2.59-2.47 (m, 4H), 2.45-2.35 (m, 3H), 2.32-2.23 (m, 3H), 2.18-1.94 (m, 5H), 1.87-1.77 (m, 1H), 1.59 (dd, J=15.2, 8.4 Hz, 1H), 1.12 (t, J=7.2 Hz, 3H).

$^{13}$C-NMR (100 MHz, CDCl$_3$) δ: 172.2, 167.6, 141.5, 134.5, 131.2, 122.7, 120.4, 116.1, 90.2, 84.8, 84.2, 83.0, 78.7, 75.7, 70.9, 68.6, 61.6, 58.0, 56.7, 56.2, 55.6, 51.1, 49.9, 49.1, 48.6, 47.7, 47.4, 44.9, 36.4, 32.0, 30.5, 26.9, 26.3, 24.2, 13.6.

HR-ESI-MS m/z: [(M+H)$^+$, 641.3510].

Example 39 Preparation of Compound 39 with Lappaconitine and Cyclopropanecarbonyl Chloride 198 mg of N-deacetyl lappaconitine was added into a 25 mL round-bottom flask, and dissolved with 5 mL of dry dichloromethane. 600 μL of dry pyridine was dropwise added under the protection of Ar, and 115 mg of cyclopropanecarbonyl chloride was introduced under an ice bath. The reaction mixture was reacted at 35° C., where the reaction was monitored by thin-layer chromatography. After reacted for 19 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 184 mg of a light yellow foamy solid as a target compound 39 C$_{34}$H$_{46}$N$_2$O$_8$ (82.6% yield), which was structurally shown as follows:

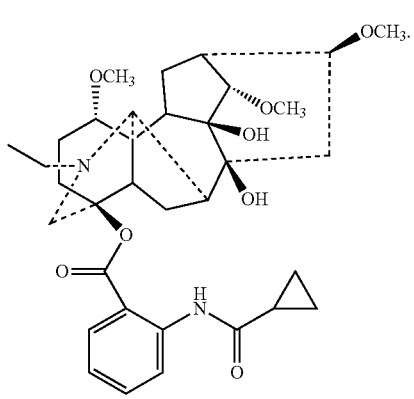

39

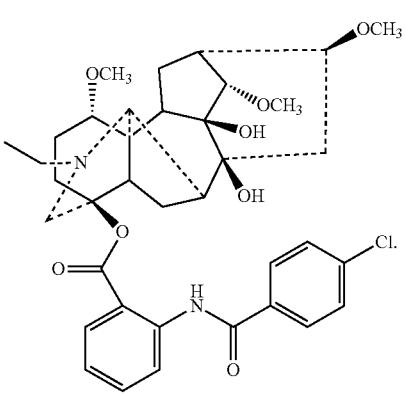

40

The target compound 39 was characterized as follows.

$^1$H-NMR (400 MHz, CDCl$_3$) δ: 11.31 (s, 1H), 8.67 (dd, J=8.6, 1.2 Hz, 1H), 7.93 (dd, J=8.0, 1.6 Hz, 1H), 7.47 (ddd, J=8.8, 7.4, 1.8 Hz, 1H), 7.00 (t, J=7.8 Hz, 1H), 3.59 (d, J=11.4 Hz, 1H), 3.54 (s, 1H), 3.44 (d, J=4.8 Hz, 1H), 3.41 (s, 3H), 3.31 (s, 3H), 3.30 (s, 3H), 3.19 (dd, J=10.3, 7.0 Hz, 1H), 3.01 (s, 1H), 2.74-2.64 (m, 2H), 2.62-2.46 (m, 5H), 2.43-2.35 (m, 3H), 2.27 (s, 1H), 2.18-1.96 (m, 5H), 1.87-1.77 (m, 1H), 1.67-1.56 (m, 1H), 1.13 (t, J=7.2 Hz, 3H), 1.08 (dd, J=4.4, 3.0 Hz, 2H), 0.86 (dd, J=7.8, 3.2 Hz, 2H).

$^{13}$C-NMR (100 MHz, CDCl$_3$) δ: 172.8, 167.7, 142.0, 134.5, 131.2, 122.2, 120.4, 115.7, 90.3, 84.7, 84.4, 83.0, 78.7, 75.8, 61.7, 58.1, 56.7, 56.3, 55.7, 51.1, 50.0, 49.2, 48.7, 47.7, 45.0, 36.5, 32.0, 27.0, 26.4, 24.3, 16.9, 13.7, 8.4, 8.3.

HR-ESI-MS m/z: [(M+H)$^+$, 611.3364].

The target compound 40 was characterized as follows.

$^1$H-NMR (400 MHz, CDCl$_3$) δ: 12.05 (s, 1H), 8.84 (d, J=8.8 Hz, 1H), 7.99-7.93 (m, 3H), 7.55 (t, J=8.0 Hz, 1H), 7.49 (d, J=8.6 Hz, 2H), 7.08 (d, J=7.4 Hz, 1H), 3.57 (d, J=10.8 Hz, 2H), 3.43 (d, J=4.8 Hz, 1H), 3.40 (s, 3H), 3.30 (s, 3H), 3.29 (s, 3H), 3.19 (dd, J=10.4, 7.2 Hz, 1H), 3.01 (s, 1H), 2.73-2.61 (m, 2H), 2.58-2.43 (m, 5H), 2.41-2.30 (m, 3H), 2.18-1.96 (m, 5H), 1.91-1.82 (m, 1H), 1.60 (dd, J=15.2, 8.2 Hz, 1H), 1.12 (t, J=7.2 Hz, 3H).

$^{13}$C-NMR (100 MHz, CDCl$_3$) δ: 167.9, 164.8, 141.9, 138.3, 134.7, 133.6, 131.4, 129.2, 129.2, 129.0, 129.0, 122.9, 120.5, 116.4, 90.3, 85.0, 84.3, 83.1, 78.7, 75.8, 61.7, 58.1, 56.7, 56.3, 55.7, 51.2, 49.9, 49.1, 48.6, 47.7, 45.1, 36.5, 32.0, 27.0, 26.4, 24.3, 13.7.

HR-ESI-MS m/z: [(M+H)$^+$, 681.1469].

Example 41 Preparation of Compound 41 with Lappaconitine and 5-Chloropyrazine-2-Carboxylic Acid 156 mg of 5-chloropyrazine-2-carboxylic acid was added into a 25 mL dry round-bottom flask, and dissolved with 10 mL of dry dichloromethane. A few drops of dimethylformamide was added, and 300 mg of oxalyl chloride was dropwise added under an ice bath. The reaction mixture was reacted at room temperature for 2 h to obtain 5-chloropyrazine-2-acid chloride. 88 mg of N-deacetyl lappaconitine was added into another 25 mL round-bottom flask, and dissolved with 10 mL of dry dichloromethane. 105 μL of dry pyridine was dropwise added under the protection of Ar, and the prepared 5-chloropyrazine-2-acid chloride was slowly dropwise added.

The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 84 mg of a light yellow foamy solid as a target compound 41 C35H43C1N4O8 (75.7% yield), which was structurally shown as follows:

Example 40 Preparation of Compound 40 with Lappaconitine and 4-Chlorobenzoyl Chloride 210 mg of N-deacetyl lappaconitine was added into a 25 mL round-bottom flask, and dissolved with 5 mL of dry dichloromethane. 600 μL of dry pyridine was added under the protection of Ar, and 200 mg of 4-chlorobenzoyl chloride was introduced under an ice bath. The reaction mixture was reacted at 20° C., where the reaction was monitored by thin-layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 240 mg of a light yellow foamy solid as a target compound 40 C$_{37}$H$_{45}$N$_2$O$_8$ (91.0% yield), which was structurally shown as follows:

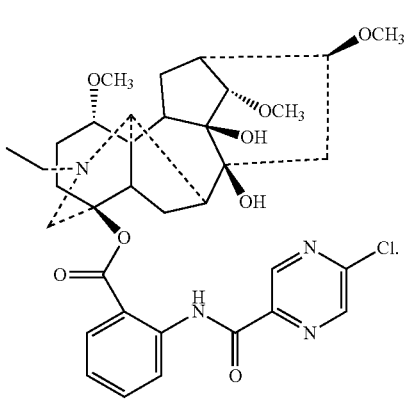

41

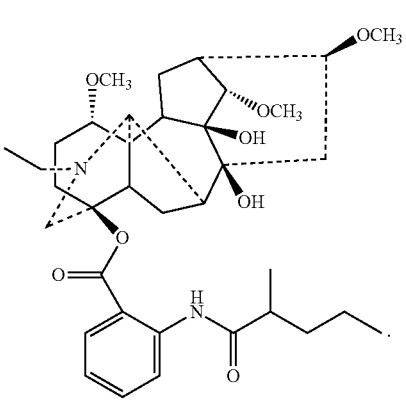

42

The target compound 41 was characterized as follows.

$^1$H-NMR (400 MHz, CDCl$_3$) δ: 12.75 (s, 1H), 9.25 (d, J=1.4 Hz, 1H), 8.86 (dd, J=8.6, 1.2 Hz, 1H), 8.76 (d, J=1.4 Hz, 1H), 8.00 (dd, J=8.0, 1.8 Hz, 1H), 7.58 (t, J=8.8 Hz, 1H), 7.14 (t, J=8.4 Hz, 1H), 3.63 (d, J=10.8 Hz, 1H), 3.54 (s, 1H), 3.45 (d, J=4.8 Hz, 1H), 3.41 (s, 3H), 3.32 (s, 3H), 3.31 (s, 3H), 3.21 (dd, J=10.2, 6.8 Hz, 1H), 3.02 (s, 1H), 2.69 (dd, J=14.8, 7.8 Hz, 2H), 2.61-2.35 (m, 8H), 2.26 (s, 1H), 2.18-2.08 (m, 3H), 2.02 (dd, J=15.0, 7.6 Hz, 2H), 1.86 (t, J=13.0 Hz, 1H), 1.14 (t, J=7.2 Hz, 3H).

$^{13}$C-NMR (100 MHz, CDCl$_3$) δ: 166.9, 161.3, 152.2, 144.5, 143.7, 140.4, 134.4, 131.5, 123.6, 120.9, 117.7, 90.3, 84.8, 84.3, 83.0, 78.7, 75.8, 61.6, 58.1, 56.7, 56.3, 55.7, 51.1, 49.9, 49.1, 47.7, 44.9, 36.4, 34.6, 31.9, 29.8, 27.0, 26.4, 24.2, 13.7.

HR-ESI-MS m/z: [(M+H)$^+$, 683.2892].

Example 42 Preparation of Compound 42 with Lappaconitine and 2-Methylvaleric Acid 130 mg of 2-methylvaleric acid was added into a 25 mL dry round-bottom flask, and dissolved with 10 mL of dry dichloromethane. A few drops of dimethylformamide were added, and 129 mg of oxalyl chloride was slowly dropwise added under an ice bath. The reaction mixture was reacted at room temperature for 2 h to obtain 2-methylvaleryl chloride. 101 mg of N-deacetyl lappaconitine was added into a 25 mL round-bottom flask, and dissolved with 10 mL of dry dichloromethane. 105 μL of dry pyridine was dropwise added under the protection of Ar, and the prepared 2-methylvaleryl chloride was slowly dropwise added. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 41 mg of a light yellow foamy solid as a target compound 42 C$_3$H$_{52}$N$_2$O$_8$ (35.6% yield), which was structurally shown as follows:

The target compound 42 was characterized as follows.

$^1$H-NMR (400 MHz, CDCl$_3$) δ: 11.09 (s, 1H), 8.71 (d, J=8.6 Hz, 1H), 7.92 (dd, J=8.0, 1.8 Hz, 1H), 7.49 (t, J=8.0 Hz, 1H), 7.02 (t, J=7.6 Hz, 1H), 3.59 (d, J=11.6 Hz, 1H), 3.55 (s, 1H), 3.44 (d, J=5.0 Hz, 1H), 3.41 (s, 3H), 3.31 (s, 3H), 3.30 (s, 3H), 3.19 (dd, J=10.4, 7.0 Hz, 1H), 3.01 (s, 1H), 2.72-2.63 (m, 2H), 2.60-2.47 (m, 4H), 2.45-2.34 (m, 4H), 2.27 (s, 1H), 2.19-1.96 (m, 5H), 1.88-1.69 (m, 3H), 1.60 (dd, J=15.3, 8.2 Hz, 1H), 1.42-1.36 (m, 3H), 1.24 (s, 2H), 1.12 (t, J=7.2 Hz, 3H), 0.93 (t, J=7.2 Hz, 3H).

HR-ESI-MS m/z: [(M+H)$^+$, 641.3828].

Example 43 Preparation of Compound 43 by Lappaconitine and 4-Iodobenzoic Acid 320 mg of 4-iodobenzoic acid was added into a 25 mL dry round-bottom flask, and dissolved with 10 mL of dry dichloromethane. A few drops of dimethylformamide were added, and 491 mg of oxalyl chloride were dropwise added under an ice bath. The reaction mixture was reacted at room temperature for 3 h to obtain 4-iodobenzoyl chloride. 210 mg of N-deacetyl lappaconitine was added into a 25 mL round-bottom flask, and dissolved with 10 mL of dry dichloromethane. 300 μL of dry pyridine was dropwise added under the protection of Ar, and the prepared 4-iodobenzoyl chloride was slowly dropwise added. The reaction mixture was reacted at 35° C., where the reaction was monitored by thin-layer chromatography. After reacted for 14 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 270 mg of a light yellow foamy solid as a target compound 43 C$_{37}$H$_{45}$IN$_2$O$_8$ (90.3% yield), which was structurally shown as follows:

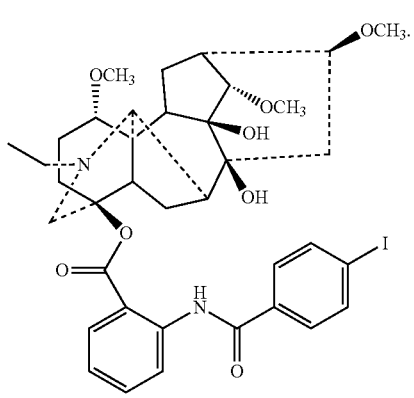

43

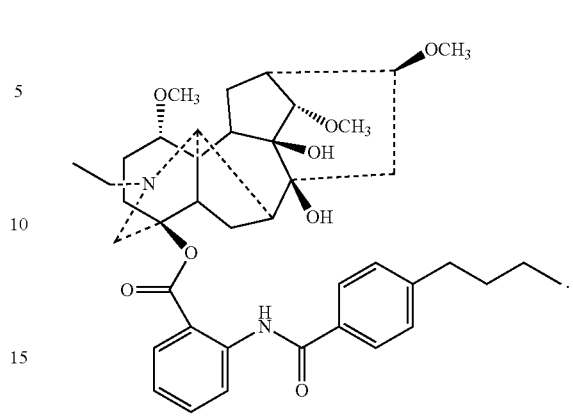

44

The target compound 43 was characterized as follows.

¹H-NMR (400 MHz, CDCl₃) δ: 12.06 (s, 1H), 8.83 (t, J=8.0 Hz, 1H), 7.96 (t, J=6.6 Hz, 1H), 7.87 (t, J=6.8 Hz, 2H), 7.73 (dd, J=8.2, 5.6 Hz, 2H), 7.55 (q, J=7.0 Hz, 1H), 7.07 (t, J=7.6 Hz, 1H), 3.72-3.66 (m, 2H), 3.56 (dd, J=11.4, 5.2 Hz, 1H), 3.40 (s, 3H), 3.31 (s, 3H), 3.29 (s, 3H), 3.23-3.15 (m, 1H), 3.00 (d, J=5.4 Hz, 1H), 2.74-2.60 (m, 2H), 2.59-2.40 (m, 5H), 2.37 (dd, J=7.8, 4.8 Hz, 2H), 2.19-1.94 (m, 6H), 1.90-1.80 (m, 1H), 1.59 (dt, J=14.6, 7.0 Hz, 1H), 1.12 (t, J=7.2 Hz, 3H).

¹³C-NMR (100 MHz, CDCl₃) δ: 167.9, 165.1, 141.8, 138.2, 138.2, 134.7, 134.6, 131.4, 129.2, 129.2, 122.9, 120.6, 116.4, 99.2, 90.3, 85.0, 84.3, 83.0, 76.8, 75.8, 61.7, 58.1, 56.7, 56.3, 55.6, 51.2, 49.9, 49.1, 48.6, 47.7, 45.0, 36.5, 32.0, 27.0, 26.4, 24.3, 13.7.

HR-ESI-MS m/z: [(M+H)⁺, 773.2341].

Example 44 Preparation of Compound 44 with Lappaconitine and 4-n-Butylbenzoic Acid 178 mg of 4-n-butylbenzoic acid was added into a 25 mL dry round-bottom flask, and dissolved with 5 mL of dry dichloromethane. A few drops of dimethylformamide were added, and 300 mg of oxalyl chloride was dropwise added under an ice bath. The reaction mixture was reacted at room temperature for 2 h to obtain 4-n-butylbenzoyl chloride. 106 mg of N-deacetyl lappaconitine in a 25 mL round-bottom flask, and dissolved with 10 mL of dry dichloromethane. 105 μL of dry pyridine was dropwise added under the protection of Ar, and the prepared 4-n-butylbenzoyl chloride was slowly dropwise added. The reaction mixture was reacted at 35° C., where the reaction was monitored by thin-layer chromatography. After reacted for 15 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 81 mg of a light yellow foamy solid as a target compound 44 $C_{41}H_{54}N_2O_8$ (59.1% yield), which was structurally shown as follows:

The target compound 44 was characterized as follows.

¹H-NMR (400 MHz, CDCl₃) δ: 11.99 (s, 1H), 8.89 (d, J=8.6 Hz, 1H), 8.05-7.87 (m, 3H), 7.56 (ddd, J=8.8, 7.4, 1.8 Hz, 1H), 7.33 (d, J=8.0 Hz, 2H), 7.11-7.02 (m, 1H), 3.61 (d, J=11.4 Hz, 1H), 3.56 (s, 1H), 3.45 (d, J=5.0 Hz, 1H), 3.41 (s, 3H), 3.32 (s, 3H), 3.30 (s, 3H), 3.21 (dd, J=10.4, 7.0 Hz, 1H), 3.02 (s, 1H), 2.71-2.66 (m, 3H), 2.59-2.48 (m, 4H), 2.46-2.35 (m, 3H), 2.27 (s, 1H), 2.20-2.09 (m, 3H), 2.07-1.95 (m, 2H), 1.90-1.81 (m, 1H), 1.69-1.58 (m, 3H), 1.38 (dq, J=15.0, 7.2 Hz, 3H), 1.13 (t, J=7.2 Hz, 3H), 0.94 (t, J=7.4 Hz, 3H).

¹³C-NMR (100 MHz, CDCl₃) δ: 167.8, 165.9, 147.4, 142.1, 134.5, 132.5, 131.3, 128.9, 128.9, 127.6, 127.6, 122.5, 120.5, 116.3, 90.3, 84.7, 84.3, 83.0, 78.7, 75.7, 61.6, 58.1, 56.7, 56.2, 55.6, 51.1, 49.9, 49.1, 48.6, 47.7, 44.9, 36.4, 35.7, 33.4, 31.9, 26.9, 26.4, 24.2, 22.4, 14.1, 13.7.

HR-ESI-MS m/z: [(M+H)⁺, 703.2626].

Example 45 Preparation of Compound 45 with Lappaconitine and 5-Chloro-2-Acyl Chloride Thiophene 99 mg of N-deacetyl lappaconitine was added into a 25 mL round-bottom flask, and dissolved with 5 mL of dry dichloromethane. 105 μL of dry pyridine was dropwise added under the protection of Ar, and 88 mg of 5-chloro-2-acyl chloride thiophene was slowly dropwise added. The reaction was reacted at 20° C., where the reaction was monitored by thin-layer chromatography. After reacted for 1.5, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 90 mg of a light yellow foamy solid as a target compound 45 $C_{35}H_{43}ClN_2O_8S$ (80.8% yield), which was structurally shown as follows:

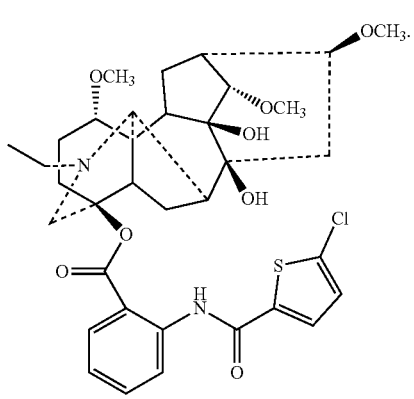

The target compound 45 was characterized as follows.

$^1$H-NMR (400 MHz, CDCl$_3$) δ: 12.02 (s, 1H), 8.73 (dd, J=8.6, 1.2 Hz, 1H), 7.97 (dd, J=8.0, 1.6 Hz, 1H), 7.57-7.51 (m, 2H), 7.10-7.04 (m, 1H), 6.98 (d, J=4.2 Hz, 1H), 3.59 (d, J=11.4 Hz, 1H), 3.56 (s, 1H), 3.45 (d, J=4.8 Hz, 1H), 3.41 (s, 3H), 3.32 (s, 3H), 3.31 (s, 3H), 3.21 (dd, J=10.4, 7.0 Hz, 1H), 3.02 (s, 1H), 2.74-2.63 (m, 2H), 2.61-2.48 (m, 4H), 2.45 (d, J=8.0 Hz, 1H), 2.42-2.36 (m, 2H), 2.27 (s, 1H), 2.20-2.07 (m, 3H), 2.06-1.96 (m, 2H), 1.92-1.82 (m, 1H), 1.60 (dd, J=15.0, 8.0 Hz, 1H), 1.13 (t, J=7.2 Hz, 3H).

$^{13}$C-NMR (100 MHz, CDCl$_3$) δ: 168.0, 159.5, 141.6, 139.2, 136.5, 134.7, 131.4, 128.0, 127.5, 122.8, 120.3, 116.1, 90.3, 85.1, 84.3, 83.1, 78.7, 75.8, 61.7, 58.1, 56.7, 56.3, 55.7, 51.2, 49.9, 49.1, 48.6, 47.7, 45.1, 36.5, 32.0, 27.0, 26.4, 24.3, 13.7.

HR-ESI-MS m/z: [(M+H)$^+$, 687.2567].

The target compound 46 was characterized as follows.

$^1$H-NMR (400 MHz, CDCl$_3$) δ: 11.99 (s, 1H), 8.89 (dd, J=8.6, 1.2 Hz, 1H), 7.96 (t, J=7.6 Hz, 3H), 7.56 (ddd, J=8.8, 7.4, 1.8 Hz, 1H), 7.35 (d, J=8.0 Hz, 2H), 7.06 (t, J=7.0 Hz, 1H), 3.61 (d, J=11.6 Hz, 1H), 3.56 (s, 1H), 3.45 (d, J=4.8 Hz, 1H), 3.41 (s, 3H), 3.32 (s, 3H), 3.30 (s, 3H), 3.21 (dd, J=10.4, 6.9 Hz, 1H), 3.02 (s, 1H), 2.77-2.65 (m, 4H), 2.61-2.48 (m, 4H), 2.45 (d, J=7.2 Hz, 1H), 2.40-2.36 (m, 2H), 2.27 (s, 1H), 2.19-1.97 (m, 5H), 1.91-1.81 (m, 1H), 1.62 (dd, J=15.2, 8.2 Hz, 1H), 1.28 (t, J=7.6 Hz, 3H), 1.13 (t, J=7.2 Hz, 3H).

$^{13}$C-NMR (100 MHz, CDCl$_3$) δ: 167.8, 165.9, 148.7, 142.2, 134.6, 132.6, 131.3, 128.4, 128.4, 127.7, 127.7, 122.5, 120.6, 116.4, 90.3, 84.8, 84.4, 83.1, 78.7, 75.8, 61.7, 58.1, 56.7, 56.3, 55.7, 51.1, 49.9, 49.1, 48.6, 47.7, 45.0, 36.5, 32.0, 29.0, 27.0, 26.4, 24.3, 15.4, 13.7.

HR-ESI-MS m/z: [(M+H)$^+$, 675.3637].

Example 46 Preparation of Compound 46 with Lappaconitine and 3-Ethylbenzoyl Chloride 220 mg of N-deacetyl lappaconitine was added in a 25 mL round-bottom flask, and dissolved with 5 mL of dry dichloromethane. 600 μL of dry pyridine was dropwise added under the protection of Ar, and 205 mg of 3-ethylbenzoyl chloride was introduced under an ice bath. The reaction mixture was reacted at 35° C., where the reaction was monitored by thin-layer chromatography. After reacted for 19 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 227 mg of a light yellow foamy solid as a target compound 46 C$_{39}$H$_{50}$N$_2$O$_8$ (83.0% yield), which was structurally shown as follows:

Example 47 Preparation of Compound 47 with Lappaconitine and 3,3-Dimethylbutyryl Chloride 102 mg of N-deacetyl lappaconitine was added into a 25 mL round-bottomed flask, and dissolved with 5 mL of dry dichloromethane. 105 μL of dry pyridine was dropwise added under the protection of Ar, and 78 mg of 3,3-dimethylbutyryl chloride was slowly dropwise added. The reaction mixture was reacted at 20° C., where the reaction was monitored by thin-layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 78 mg of a light yellow foamy solid as a target compound 47 C$_{36}$H$_{52}$N$_2$O$_8$ (64.8% yield), which was structurally shown as follows:

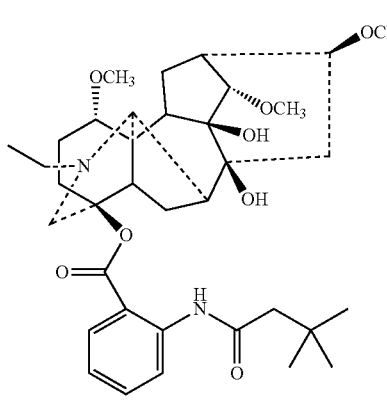

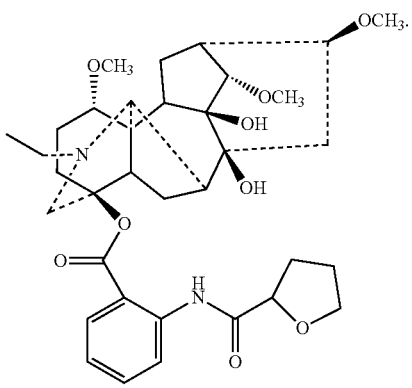

The target compound 47 was characterized as follows.

$^{1}$H-NMR (400 MHz, CDCl$_3$) δ: 10.97 (s, 1H), 8.69 (dd, J=8.6, 1.2 Hz, 1H), 7.91 (dd, J=8.0, 1.8 Hz, 1H), 7.49 (ddd, J=8.8, 7.4, 1.8 Hz, 1H), 7.02 (t, J=7.2 Hz, 1H), 3.58 (d, J=11.4 Hz, 1H), 3.55 (s, 1H), 3.44 (d, J=4.8 Hz, 1H), 3.41 (s, 3H), 3.31 (s, 3H), 3.30 (s, 3H), 3.19 (dd, J=10.4, 7.0 Hz, 1H), 3.01 (s, 1H), 2.71-2.61 (m, 2H), 2.60-2.45 (m, 5H), 2.44-2.35 (m, 3H), 2.28 (s, 2H), 2.18-2.07 (m, 3H), 2.05-1.96 (m, 2H), 1.85-1.76 (m, 1H), 1.59 (dd, J=15.2, 8.4 Hz, 1H), 1.12 (t, J=7.2 Hz, 3H), 1.10 (s, 9H).

$^{13}$C-NMR (100 MHz, CDCl$_3$) δ: 171.0, 167.5, 141.6, 134.3, 131.1, 122.3, 120.4, 116.1, 90.2, 84.6, 84.3, 83.0, 78.7, 75.7, 61.7, 58.0, 58.0, 56.7, 56.2, 55.6, 52.7, 51.0, 49.9, 49.1, 48.6, 47.7, 44.9, 36.4, 31.9, 31.4, 30.0, 29.9, 26.9, 26.3, 24.2, 13.7.

HR-ESI-MS m/z: [(M+H)$^+$, 641.3213].

Example 48 Preparation of Compound 48 with Lappaconitine and 2-Tetrahydrofurancarboxylic Acid 116 mg of 2-tetrahydrofurancarboxylic acid was added into a 25 mL dry round-bottom flask, and dissolved with 10 mL of dry dichloromethane. A few drops of dimethylformamide were added, and 375 mg of oxalyl chloride was dropwise added under an ice bath. The reaction mixture was reacted at room temperature for 2 h to obtain 2-tetrahydrofuroyl chloride. 99 mg of N-deacetyl lappaconitine was added into a 25 mL round-bottom flask, and dissolved with 10 mL of dry dichloromethane. 105 μL of dry pyridine was added under the protection of Ar, and the prepared 2-tetrahydrofuroyl chloride was slowly dropwise added. The reaction mixture was reacted at 35° C., where the reaction was monitored by thin-layer chromatography. After reacted for 14 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 99 mg of a light yellow foamy solid as a target compound 48 C$_{35}$H$_{48}$N$_2$O$_9$ (85.9% yield), which was structurally shown as follows:

The target compound 48 was characterized as follows.

$^{1}$H-NMR (400 MHz, CDCl$_3$) δ: 11.80 (d, J=5.2 Hz, 1H), 8.70 (d, J=8.6 Hz, 1H), 7.92 (d, J=8.0 Hz, 1H), 7.50 (t, J=8.8 Hz, 1H), 7.05 (ddd, J=8.4, 7.4, 1.2 Hz, 1H), 4.52 (dd, J=8.4, 5.0 Hz, 1H), 4.22-4.12 (m, 1H), 4.01 (q, J=7.4 Hz, 1H), 3.66 (d, J=11.4 Hz, 1H), 3.58 (d, J=11.6 Hz, 1H), 3.54 (d, J=5.6 Hz, 1H), 3.44 (d, J=4.8 Hz, 1H), 3.41 (s, 3H), 3.31 (s, 3H), 3.30 (s, 3H), 3.19 (dd, J=10.2, 6.8 Hz, 1H), 3.01 (s, 1H), 2.76-2.64 (m, 2H), 2.58-2.48 (m, 4H), 2.39-2.35 (m, 2H), 2.31-2.25 (m, 2H), 2.18-2.07 (m, 3H), 2.05-1.88 (m, 5H), 1.80-1.72 (m, 1H), 1.60 (dd, J=15.2, 8.4 Hz, 1H), 1.12 (t, J=7.2 Hz, 3H).

$^{13}$C-NMR (100 MHz, CDCl$_3$) δ: 173.0, 166.9, 140.5, 134.1, 131.1, 122.8, 120.4, 117.2, 90.2, 84.3, 83.0, 79.1, 78.6, 75.6, 69.8, 61.6, 57.9, 56.6, 56.2, 55.4, 51.0, 49.9, 49.1, 48.7, 48.3, 47.6, 44.8, 36.3, 31.8, 30.7, 26.9, 26.3, 25.4, 24.1, 13.6.

HR-ESI-MS m/z: [(M+H)$^+$, 641.3510].

Example 49 Preparation of Compound 49 with Lappaconitine and 4-Isopropylbenzoic Acid 120 mg of 4-isopropylbenzoic acid was added into a 25 mL dry round-bottom flask, and dissolved with 10 mL dry dichloromethane. A few drops of dimethylformamide were added, and 129 mg of oxalyl chloride was dropwise added under an ice bath. The reaction mixture was reacted at room temperature for 3 h to obtain 4-isopropylbenzoyl chloride. 69 mg of N-deacetyl lappaconitine was added into a 25 mL round-bottom flask, and dissolved with 10 mL of dry dichloromethane. 105 μL of dry pyridine was dropwise added under the protection of Ar, and the prepared 4-isopropylbenzoyl chloride was slowly dropwise added. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 103 mg of a light yellow foamy solid as a target compound 49 C$_{40}$H$_{52}$N$_2$O$_8$ (87.3% yield), which was structurally shown as follows:

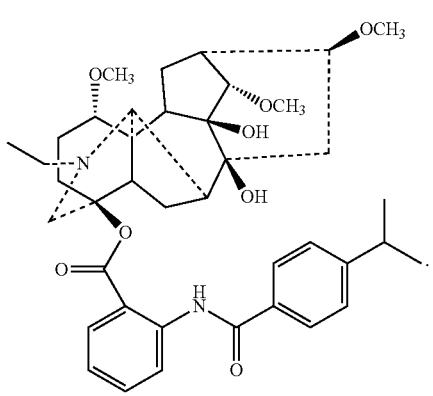

49

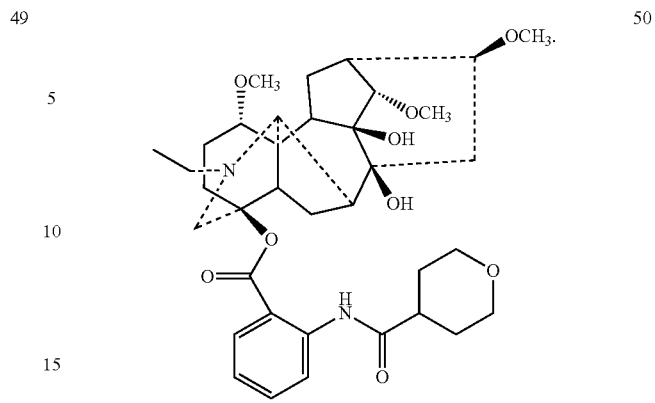

50

The target compound 49 was characterized as follows.

$^{1}$H-NMR (400 MHz, CDCl$_3$) δ: 11.99 (s, 1H), 8.89 (d, J=7.4 Hz, 1H), 8.00-7.94 (m, 3H), 7.55 (ddd, J=8.8, 7.4, 1.8 Hz, 1H), 7.38 (d, J=8.2 Hz, 2H), 7.10-7.02 (m, 1H), 3.60 (d, J=11.6 Hz, 1H), 3.56 (s, 1H), 3.44 (d, J=4.8 Hz, 1H), 3.41 (s, 3H), 3.31 (s, 3H), 3.30 (s, 3H), 3.21 (dd, J=10.4, 7.0 Hz, 1H), 3.02 (s, 1H), 2.98 (dd, J=14.0, 7.0 Hz, 1H), 2.74-2.64 (m, 2H), 2.60-2.47 (m, 4H), 2.45 (d, J=7.6 Hz, 1H), 2.42-2.35 (m, 2H), 2.30 (s, 1H), 2.19-1.97 (m, 5H), 1.91-1.81 (m, 1H), 1.62 (dd, J=15.2, 8.4 Hz, 1H), 1.29 (d, J=7.0 Hz, 6H), 1.13 (t, J=7.2 Hz, 3H).

$^{13}$C-NMR (100 MHz, CDCl$_3$) δ: 167.8, 165.9, 153.3, 142.2, 134.6, 132.7, 131.3, 127.7, 127.7, 127.0, 127.0, 122.5, 120.6, 116.4, 90.3, 84.7, 84.4, 83.1, 78.7, 75.8, 61.7, 58.1, 56.7, 56.3, 55.7, 51.1, 49.9, 49.2, 48.6, 47.7, 45.0, 36.5, 34.3, 32.0, 29.8, 27.0, 26.4, 23.9, 24.3, 13.7.

HR-ESI-MS m/z: [(M+H)$^{+}$, 689.3871].

Example 50 Preparation of Compound 50 with Lappaconitine and Tetrahydrofuran-4-Carbonyl Chloride 68 mg of N-deacetyl lappaconitine was added into a 25 mL round-bottom flask, and dissolved with 5 mL of dry dichloromethane. 300 μL of dry pyridine was dropwise added under the protection of Ar, and a 60 mg of tetrahydrofuran-4-carbonyl chloride was slowly dropwise added. The reaction mixture was reacted at 20° C., where the reaction was monitored by thin-layer chromatography. After reacted for 18 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 32 mg of a light yellow foamy solid as a target compound 50 C$_{36}$H$_{50}$N$_2$O$_9$ (39.1% yield), which was structurally shown as follows:

The target compound 50 was characterized as follows.

$^{1}$H-NMR (400 MHz, CDCl$_3$) δ: 11.20 (s, 1H), 8.69 (d, J=8.5 Hz, 1H), 7.93 (dd, J=8.0, 1.6 Hz, 1H), 7.50 (t, J=7.6 Hz, 1H), 7.03 (t, J=7.6 Hz, 1H), 4.07 (d, J=11.8 Hz, 2H), 3.58-3.46 (m, 4H), 3.44 (d, J=4.8 Hz, 1H), 3.41 (s, 3H), 3.31 (s, 3H), 3.30 (s, 3H), 3.20 (dd, J=10.3, 6.9 Hz, 1H), 3.01 (s, 1H), 2.69 (dd, J=15.2, 7.6 Hz, 1H), 2.64-2.46 (m, 6H), 2.46-2.35 (m, 3H), 2.29 (s, 1H), 2.19-1.96 (m, 5H), 1.95-1.87 (m, 4H), 1.91-1.81 (m, 1H), 1.59 (dd, J=15.2, 8.2 Hz, 1H), 1.12 (t, J=7.2 Hz, 3H).

$^{13}$C-NMR (100 MHz, CDCl$_3$) δ: 173.5, 167.7, 141.8, 134.6, 131.3, 122.6, 120.5, 90.3, 84.8, 84.4, 83.1, 78.7, 75.8, 67.5, 61.7, 58.1, 56.7, 56.3, 55.7, 51.1, 49.9, 49.2, 48.6, 47.7, 45.1, 44.0, 36.5, 32.0, 31.7, 29.8, 29.3, 29.3, 27.0, 26.4, 24.3, 13.7.

HR-ESI-MS m/z: [(M+H)$^{+}$, 655.3666].

Example 51 Preparation of Compound 51 with Lappaconitine and 5-Bromo-2-Thiophenecarboxylic Acid 246 mg of 5-bromo-2-thiophenecarboxylic acid was added into a 25 mL dry round-bottom flask, and dissolved with 10 mL of dry dichloromethane. A few drops of dimethylformamide were added, and 389 mg of oxalyl chloride was dropwise added under an ice bath. The reaction mixture was reacted at room temperature for 3 h to obtain 5-bromo-2-thiophene chloride. 168 mg of N-deacetyl lappaconitine was added into a 25 mL round-bottom flask, and dissolved with 10 mL of dry dichloromethane. 300 μL of dry pyridine was dropwise added under the protection of Ar, and the prepared 5-bromo-2-thiophene chloride was slowly dropwise added. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 223 mg of a light yellow foamy solid as a target product 51 C$_{35}$H$_{43}$BrN$_2$O$_8$S (98.7% yield), which was structurally shown as follows:

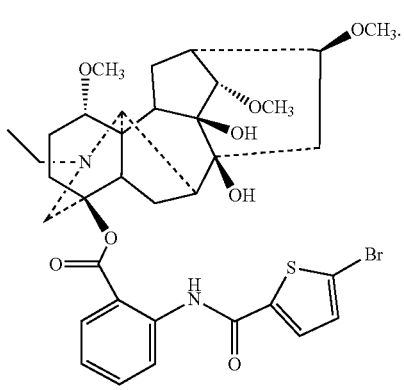

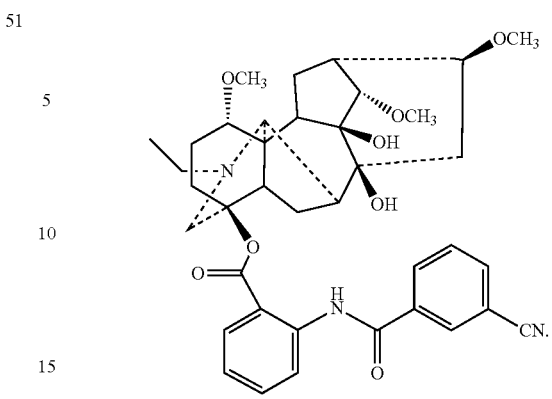

The target compound 51 was characterized as follows.

$^1$H-NMR (400 MHz, CDCl3) δ: 12.01 (s, 1H), 8.73 (dd, J=8.5, 1.1 Hz, 1H), 7.96 (dd, J=8.0, 1.6 Hz, 1H), 7.54 (ddd, J=8.8, 7.4, 1.8 Hz, 1H), 7.49 (d, J=4.0 Hz, 1H), 7.12 (d, J=4.0 Hz, 1H), 7.07 (ddd, J=8.2, 7.3, 1.2 Hz, 1H), 3.59 (d, J=11.4 Hz, 1H), 3.56 (s, 1H), 3.44 (d, J=4.8 Hz, 1H), 3.41 (s, 3H), 3.31 (s, 3H), 3.30 (s, 3H), 3.21 (dd, J=10.4, 7.0 Hz, 1H), 3.02 (s, 1H), 2.74-2.63 (m, 2H), 2.62-2.48 (m, 4H), 2.45 (d, J=8.0 Hz, 1H), 2.43-2.35 (m, 2H), 2.27 (s, 1H), 2.20-1.94 (m, 5H), 1.92-1.82 (m, 1H), 1.60 (dd, J=15.2, 8.4 Hz, 1H), 1.13 (t, J=7.2 Hz, 3H).

$^{13}$C-NMR (100 MHz, CDCl$_3$) δ: 168.0, 159.4, 142.1, 141.6, 134.7, 131.4, 131.1, 128.7, 122.9, 120.4, 119.3, 116.1, 90.3, 85.1, 84.3, 83.1, 78.7, 75.8, 61.7, 58.1, 56.7, 56.3, 55.7, 51.2, 49.9, 49.1, 48.6, 47.7, 45.1, 36.5, 32.0, 27.0, 26.4, 24.3, 13.7.

HR-ESI-MS m/z: [(M+H)$^+$, 733.2078].

Example 52 Preparation of Compound 52 with Lappaconitine and 3-Cyanobenzoyl Chloride 247 mg of 3-cyanobenzoic acid was added into a 25 mL dry round-bottom flask, and dissolved with 10 mL of dry dichloromethane. A few drops of dimethylformamide were added, and 639 mg of oxalyl chloride was dropwise added under an ice bath. The reaction mixture was reacted at room temperature for 3 h to obtain 3-cyanobenzoyl chloride. 190 mg of N-deacetyl lappaconitine was added into a 25 mL round-bottom flask, and dissolved with 10 mL of dry dichloromethane. 300 μL of dry pyridine was dropwise added under the protection of Ar, and the prepared 3-cyanobenzoyl chloride was slowly dropwise introduced. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 201 mg of a light yellow foamy solid as a target compound 52 C$_{38}$H$_{45}$N$_3$O$_8$ (83.5% yield), which was structurally shown as follows:

The target compound 52 was characterized as follows.

$^1$H-NMR (400 MHz, CDCl$_3$) δ: 12.18 (s, 1H), 8.83 (dd, J=8.6, 1.2 Hz, 1H), 8.31 (s, 1H), 8.24 (dd, J=8.0, 1.6 Hz, 1H), 8.00 (d, J=6.4 Hz, 1H), 7.84 (d, J=7.8 Hz, 1H), 7.67 (t, J=7.8 Hz, 1H), 7.58 (ddd, J=8.8, 7.4, 1.8 Hz, 1H), 7.12 (t, J=7.8 Hz, 1H), 3.58 (d, J=11.4 Hz, 1H), 3.55 (s, 1H), 3.44 (d, J=4.8 Hz, 1H), 3.41 (s, 3H), 3.31 (s, 3H), 3.30 (s, 3H), 3.22 (dd, J=10.4, 7.0 Hz, 1H), 3.02 (s, 1H), 2.74-2.62 (m, 2H), 2.60-2.42 (m, 5H), 2.38 (t, J=6.4 Hz, 2H), 2.28 (s, 1H), 2.22-1.95 (m, 5H), 1.95-1.85 (m, 1H), 1.60 (dd, J=15.2, 8.2 Hz, 1H), 1.13 (t, J=7.2 Hz, 3H).

$^{13}$C-NMR (100 MHz, CDCl$_3$) δ: 168.0, 163.5, 141.5, 136.5, 135.2, 134.8, 131.6, 131.5, 131.5, 129.9, 123.3, 120.6, 118.3, 116.6, 113.4, 90.3, 85.3, 84.2, 83.0, 78.7, 75.8, 61.6, 58.1, 56.7, 56.3, 55.7, 51.2, 49.9, 49.1, 48.5, 47.7, 45.1, 36.5, 32.0, 27.0, 26.4, 24.3, 13.7 HR-ESI-MS m/z: [(M+H)$^+$, 672.3356].

Example 53 Preparation of Compound 53 with Lappaconitine and 4-Trifluoromethoxybenzoyl Chloride 161 mg of 4-trifluoromethoxybenzoic acid was added into a 25 mL dry round-bottom flask, and dissolved with 10 mL of dry dichloromethane. A few drops of dimethylformamide were added, and 129 mg of oxalyl chloride was dropwise added under an ice bath. The reaction mixture was reacted at room temperature for 3 h to obtain 4-trifluoromethoxybenzoyl chloride. 103 mg of N-deacetyl lappaconitine was added in a 25 mL round-bottom flask, and dissolved with 10 mL of dry dichloromethane. 300 μL of dry pyridine was added under the protection of Ar, and the prepared 4-trifluoromethoxybenzoyl chloride was slowly dropwise introduced. The reaction mixture was reacted at 35° C., where the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 126 mg of a light yellow foamy solid as a target product 53 C$_{38}$H$_{45}$F$_3$N$_2$O$_9$ (91.3% yield), which was structurally shown as follows:

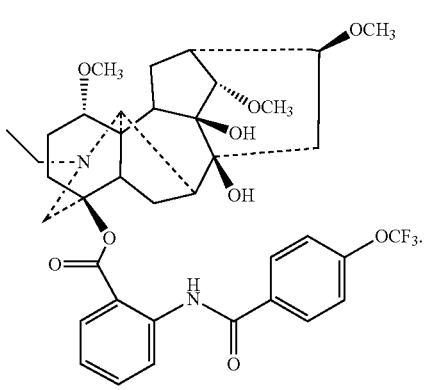

53

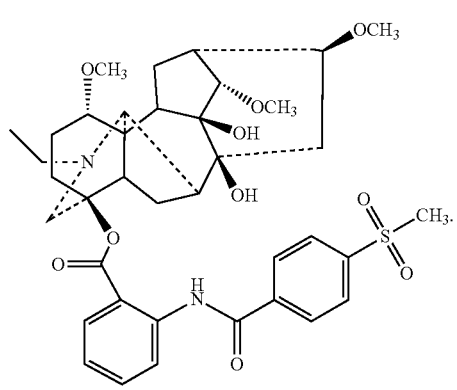

54

The target compound 53 was characterized as follows.

$^1$H-NMR (400 MHz, CDCl$_3$) δ: 12.09 (s, 1H), 8.83 (dd, J=8.6, 1.2 Hz, 1H), 8.06 (d, J=8.8 Hz, 2H), 7.97 (dd, J=8.0, 1.8 Hz, 1H), 7.56 (ddd, J=8.8, 7.4, 1.8 Hz, 1H), 7.35 (d, J=7.8 Hz, 2H), 7.11-7.06 (m, 1H), 3.62 (s, 1H), 3.57 (d, J=11.4 Hz, 1H), 3.43 (d, J=4.8 Hz, 1H), 3.40 (s, 3H), 3.30 (s, 3H), 3.29 (s, 3H), 3.20 (dd, J=10.4, 7.0 Hz, 1H), 3.01 (s, 1H), 2.73-2.60 (m, 2H), 2.59-2.42 (m, 4H), 2.41-2.35 (m, 2H), 2.18-2.07 (m, 2H), 2.05-1.92 (m, 3H), 1.92-1.83 (m, 3H), 1.59 (dd, J=15.2, 8.4 Hz, 1H), 1.12 (t, J=7.2 Hz, 3H).

$^{13}$C-NMR (100 MHz, CDCl$_3$) δ: 168.0, 164.4, 151.9, 141.8, 134.7, 133.5, 131.4, 129.5, 129.5, 129.5, 123.0, 120.9, 120.9, 120.5, 116.4, 90.3, 85.1, 84.3, 83.1, 78.7, 75.8, 61.7, 58.1, 56.7, 56.3, 55.7, 51.2, 49.9, 49.1, 48.5, 47.7, 45.1, 36.5, 32.0, 27.0, 26.4, 24.3, 13.7.

HR-ESI-MS m/z: [(M+H)$^+$, 731.3259].

Example 54 Preparation of Compound 54 with Lappaconitine and 4-(Methylsulfonyl)Benzoic Acid 295 mg of 4-(methylsulfonyl)benzoic acid was added into a 25 mL dry round-bottom flask, and dissolved with 10 mL of dry dichloromethane. A few drops of dimethylformamide were added, and 561 mg of oxalyl chloride was dropwise added under an ice bath. The reaction mixture was reacted at room temperature for 3 h to obtain 4-(methylsulfonyl)benzoyl chloride. 300 mg of N-deacetyl lappaconitine was added into a 25 mL round-bottom flask, and dissolved with 10 mL of dry dichloromethane. 300 μL of dry pyridine was dropwise added under the protection of Ar, and the prepared 4-(methanesulfonyl)benzoyl chloride was slowly dropwise introduced. The reaction mixture was reacted at 35° C., and the reaction was monitored by thin-layer chromatography. After reacted for 14 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 216 mg of a light yellow foamy solid as a target compound 54 $C_{38}H_{48}N_2O_{10}S$ (80.9% yield), which was structurally shown as follows:

The target compound 54 was characterized as follows.

$^1$H-NMR (400 MHz, CDCl$_3$) δ: 12.22 (s, 1H), 8.83 (d, J=8.6 Hz, 1H), 8.19 (d, J=7.8 Hz, 2H), 8.09 (d, J=8.6 Hz, 2H), 7.98 (d, J=8.0 Hz, 1H), 7.61-7.52 (m, 1H), 7.11 (t, J=7.8 Hz, 1H), 3.55 (d, J=12.0 Hz, 2H), 3.42 (d, J=4.8 Hz, 1H), 3.39 (s, 3H), 3.29 (s, 3H), 3.28 (s, 3H), 3.19 (dd, J=10.2, 7.2 Hz, 1H), 3.09 (s, 3H), 3.00 (s, 1H), 2.69 (dd, J=15.2, 7.6 Hz, 1H), 2.64-2.43 (m, 6H), 2.35 (dd, J=14.7, 10.0 Hz, 3H), 2.17-1.96 (m, 5H), 1.89 (t, J=14.8 Hz, 1H), 1.58 (dd, J=15.2, 8.4 Hz, 1H), 1.11 (t, J=7.2 Hz, 3H).

$^{13}$C-NMR (100 MHz, CDCl$_3$) δ: 168.0, 164.0, 143.4, 141.5, 140.1, 134.8, 131.5, 128.6, 128.6, 128.1, 128.1, 123.4, 120.6, 116.6, 90.3, 85.3, 84.3, 83.0, 78.7, 75.8, 61.7, 58.1, 56.7, 56.3, 55.7, 51.2, 49.9, 49.2, 48.4, 47.7, 45.1, 44.6, 36.4, 32.0, 27.0, 26.4, 24.3, 13.7.

HR-ESI-MS m/z: [(M+H)$^+$, 725.1605].

Example 55 Preparation of Compound 55 with Lappaconitine and 3-Bromobenzoyl Chloride 192 mg of N-deacetyl lappaconitine was added in a 25 mL round-bottom flask, and dissolved with 5 ml of dry dichloromethane. 600 μL of dry pyridine was dropwise added under the protection of Ar, and 233 mg of 3-bromobenzoyl chloride was introduced under an ice bath. The reaction mixture was reacted at 35° C., where the reaction was monitored by thin-layer chromatography. After reacted for 19 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 208 mg of a light yellow foamy solid as a target compound 55 $C_{37}H_{45}BrN_2O_8$ (81.0% yield), which was structurally shown as follows:

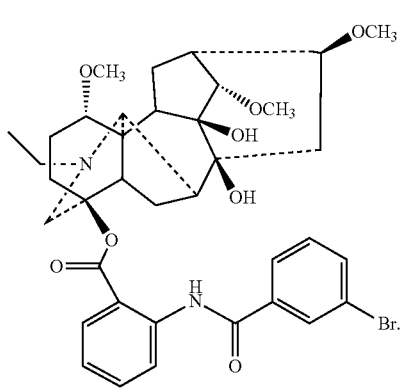

55

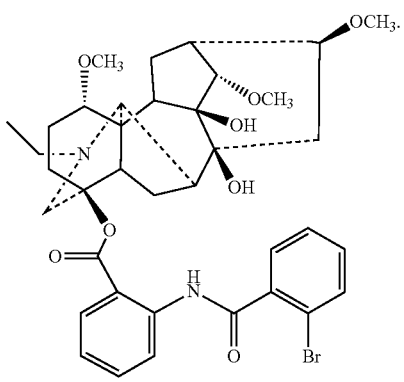

56

The target compound 55 was characterized as follows.

$^1$H-NMR (400 MHz, CDCl$_3$) δ: 12.04 (s, 1H), 8.83 (dd, J=8.5, 1.2 Hz, 1H), 8.19 (t, J=1.8 Hz, 1H), 7.98 (dd, J=8.0, 1.6 Hz, 1H), 7.91 (d, J=8.4 Hz, 1H), 7.68 (d, J=8.0 Hz, 1H), 7.57 (ddd, J=8.8, 7.4, 1.8 Hz, 1H), 7.41 (t, J=8.0 Hz, 1H), 7.10 (t, J=7.2 Hz, 1H), 3.61 (d, J=11.4 Hz, 1H), 3.56 (s, 1H), 3.44 (d, J=4.8 Hz, 1H), 3.41 (s, 3H), 3.31 (s, 3H), 3.30 (s, 3H), 3.21 (dd, J=10.4, 7.0 Hz, 1H), 3.02 (s, 1H), 2.75-2.64 (m, 2H), 2.60-2.48 (m, 4H), 2.46-2.35 (m, 3H), 2.27 (s, 1H), 2.20-1.96 (m, 5H), 1.86 (td, J=12.8, 12.0, 7.0 Hz, 1H), 1.61 (dd, J=15.2, 8.2 Hz, 1H), 1.13 (t, J=7.2 Hz, 3H).

$^{13}$C-NMR (100 MHz, CDCl$_3$) δ: 167.91, 164.36, 141.70, 137.18, 134.94, 134.69, 131.38, 131.29, 130.44, 125.68, 123.2, 123.02, 120.62, 116.54, 90.3, 85.1, 84.3, 83.1, 78.7, 75.8, 61.7, 58.1, 56.7, 56.3, 55.7, 51.2, 49.9, 49.2, 48.6, 47.7, 45.1, 36.5, 32.0, 27.0, 26.4, 24.3, 13.7.

HR-ESI-MS m/z: [(M+H)$^+$, 727.2495].

The target compound 56 was characterized as follows.

$^1$H-NMR (400 MHz, CDCl$_3$) δ: 11.43 (s, 1H), 8.87 (d, J=8.4 Hz, 1H), 7.99 (dd, J=8.2, 1.8 Hz, 1H), 7.68 (d, J=7.8 Hz, 1H), 7.63-7.57 (m, 2H), 7.44 (td, J=7.5, 1.2 Hz, 1H), 7.34 (td, J=7.8, 1.8 Hz, 1H), 7.15-7.11 (m, 1H), 3.53 (d, J=11.4 Hz, 2H), 3.45 (d, J=5.0 Hz, 1H), 3.43 (s, 3H), 3.33 (s, 3H), 3.30 (s, 3H), 3.19 (dd, J=10.3, 7.0 Hz, 1H), 3.01 (s, 1H), 2.70 (dd, J=15.2, 7.4 Hz, 1H), 2.65-2.59 (m, 1H), 2.58-2.46 (m, 4H), 2.44-2.37 (m, 3H), 2.29 (s, 1H), 2.20-1.95 (m, 5H), 1.88-1.78 (m, 1H), 1.60 (dd, J=15.2, 8.2 Hz, 1H), 1.11 (t, J=7.2 Hz, 3H).

$^{13}$C-NMR (100 MHz, CDCl$_3$) δ: 167.3, 166.5, 141.2, 138.6, 134.6, 133.9, 131.5, 131.3, 129.2, 127.8, 123.2, 120.7, 120.0, 116.8, 90.3, 84.9, 84.3, 83.0, 78.7, 75.8, 61.7, 58.1, 56.7, 56.3, 55.6, 51.1, 49.9, 49.1, 48.6, 47.7, 45.0, 36.4, 31.9, 26.9, 26.4, 24.2, 13.7.

HR-ESI-MS m/z: [(M+H)$^+$, 727.2495].

Example 57 Preparation of Compound 57 with Lappaconitine and 3-Methoxybenzoic Acid 140 mg of 3-methoxybenzoic acid was added into a 25 mL dry round-bottom flask, and dissolved with 5 mL of dry dichloromethane. A few drops of dimethylformamide were added, and 345 mg of oxalyl chloride were dropwise added under an ice bath. The reaction mixture was reacted at room temperature for 2 h to obtain cyclopentanecarbonyl chloride. 105 mg of N-deacetyl lappaconitine was added into a 25 mL round-bottom flask, and dissolved with 10 mL of dry dichloromethane. 105 μL of dry pyridine was dropwise added under the protection of Ar, and the prepared cyclopentanecarbonyl chloride was slowly dropwise introduced. The reaction mixture was reacted at 35° C., where the reaction was monitored by thin-layer chromatography. After reacted for 13 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 81 mg of a light yellow foamy solid as a target compound 57 C$_{38}$H$_{48}$N$_2$O$_9$ (91.6% yield), which was structurally shown as follows:

Example 56 Preparation of Compound 56 with Lappaconitine and 2-Bromobenzoyl Chloride 200 mg of N-deacetyl lappaconitine was added into a 25 mL round-bottom flask, and dissolved with 5 mL of dry dichloromethane. 600 μL of dry pyridine was dropwise added under the protection of Ar, and 115 mg of 2-bromobenzoyl chloride was introduced under an ice bath. The reaction mixture was reacted at 35° C., where the reaction was monitored by thin-layer chromatography. After reacted for 19 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 261 mg of a light yellow foamy solid as a target compound 56 C$_{37}$H$_{45}$BrN$_2$O$_8$ (97.5% yield), which was structurally shown as follows:

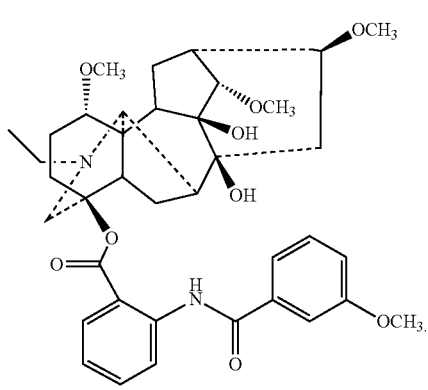

57

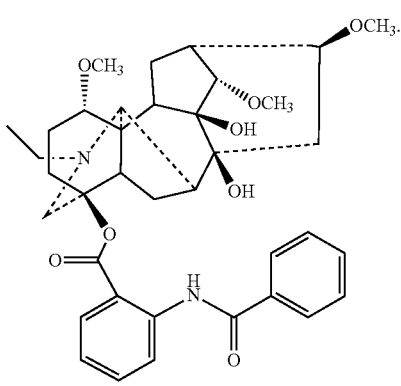

58

The target compound 57 was characterized as follows.

$^1$H-NMR (400 MHz, CDCl$_3$) δ: 12.06 (s, 1H), 8.90 (d, J=8.4 Hz, 1H), 8.00 (dd, J=8.0, 1.8 Hz, 1H), 7.64-7.55 (m, 3H), 7.46 (t, J=8.0 Hz, 1H), 7.17-7.07 (m, 2H), 3.92 (s, 3H), 3.63 (d, J=11.4 Hz, 1H), 3.58 (s, 1H), 3.47 (d, J=4.8 Hz, 1H), 3.44 (s, 3H), 3.34 (s, 3H), 3.32 (s, 3H), 3.22 (dd, J=10.3, 6.9 Hz, 1H), 3.04 (s, 1H), 2.77-2.67 (m, 2H), 2.63-2.49 (m, 4H), 2.48-2.37 (m, 3H), 2.30 (s, 1H), 2.21-2.10 (m, 3H), 2.04 (dd, J=14.8, 7.2 Hz, 2H), 1.91-1.82 (m, 1H), 1.64 (dd, J=15.1, 8.2 Hz, 1H), 1.15 (t, J=7.2 Hz, 3H).

$^{13}$C-NMR (100 MHz, CDCl$_3$) δ: 167.8, 165.6, 160.0, 141.9, 136.5, 134.5, 131.3, 129.9, 122.6, 120.4, 119.4, 118.6, 116.4, 112.4, 90.2, 84.8, 84.2, 83.0, 78.6, 75.7, 61.6, 58.0, 56.6, 56.2, 55.6, 51.0, 51.0, 49.9, 49.1, 48.5, 47.7, 44.9, 36.3, 31.9, 26.9, 26.3, 24.2, 13.6.

HR-ESI-MS m/z: [(M+H)$^+$, 676.6913].

The target compound 58 was characterized as follows.

$^1$H-NMR (400 MHz, CDCl$_3$) δ: 12.06 (s, 1H), 8.91 (d, J=8.4 Hz, 1H), 8.06 (d, J=6.0 Hz, 2H), 8.00 (dd, J=8.2, 1.6 Hz, 1H), 7.57 (dq, J=13.8, 6.6 Hz, 4H), 7.13-7.07 (m, 1H), 3.62 (d, J=11.6 Hz, 1H), 3.59 (s, 1H), 3.47 (d, J=4.8 Hz, 1H), 3.43 (s, 3H), 3.34 (s, 3H), 3.32 (s, 3H), 3.23 (dd, J=10.4, 7.0 Hz, 1H), 3.04 (s, 1H), 2.77-2.66 (m, 2H), 2.64-2.50 (m, 4H), 2.47 (d, J=7.7 Hz, 1H), 2.44-2.38 (m, 2H), 2.32 (s, 1H), 2.21-2.11 (m, 3H), 2.04 (dd, J=14.8, 7.2 Hz, 2H), 1.93-1.83 (m, 1H), 1.64 (dd, J=15.1, 8.2 Hz, 1H), 1.15 (t, J=7.1 Hz, 3H).

$^{13}$C-NMR (100 MHz, CDCl$_3$) δ: 167.8, 165.8, 142.0, 135.1, 134.6, 132.0, 131.3, 128.9, 128.9, 127.6, 127.6, 122.7, 120.5, 116.4, 90.2, 84.8, 84.3, 83.0, 78.7, 75.7, 61.6, 58.1, 56.7, 56.3, 55.6, 51.1, 49.9, 49.1, 48.6, 47.7, 45.0, 36.4, 31.9, 27.0, 26.4, 24.2, 13.7.

HR-ESI-MS m/z: [(M+H)$^+$, 646.7090].

Example 58 Preparation of Compound 58 with Lappaconitine and Benzoyl Chloride 207 mg of N-deacetyl lappaconitine was added into a 25 mL round-bottom flask, and dissolved with 5 mL of dry dichloromethane. 105 μL of dry pyridine was dropwise added under the protection of Ar, and 157 mg of benzoyl chloride was slowly dropwise introduced. The reaction mixture was reacted at 20° C., and the reaction was monitored by thin-layer chromatography. After reacted for 17 h, the reaction mixture was adjusted with a saturated aqueous sodium carbonate solution to pH 10, and then subjected to extraction with dichloromethane to obtain a dichloromethane layer. The dichloromethane layer was dried with anhydrous sodium sulfate, filtered to remove the solid sodium sulfate, subjected to rotary evaporation, and purified by column chromatography to obtain 212 mg of a light yellow foamy solid as a target product 58 C$_{37}$H$_{46}$N$_2$O$_8$ (91.6% yield), which was structurally shown as follows:

Example 59 Preparation of Compound 59 with Lappaconitine and 4-Isopropoxybenzoic Acid 182 mg of 4-isopropoxybenzoic acid was added into a 5 mL round-bottom flask, and dissolved with 2 mL of dry dichloromethane. Three drops of N,N-dimethylformamide (DMF) was added, and 0.3 mL of oxalyl chloride was dropwise added under an ice bath. The reaction mixture was reacted for 2 h followed by rotary evaporation to obtain 4-isopropoxybenzoyl chloride. 100 mg of N-deacetyl lappaconitine was added into a 5 mL round-bottom flask, and dissolved with 2 mL of dry dichloromethane. 200 μL of dry pyridine was dropwise added under the protection of Ar, and the prepared 4-isopropoxybenzoyl chloride was introduced under an ice bath. The reaction mixture was reacted at 20° C., where the reaction was monitored by thin-layer chromatography. After reacted for 16 h, the reaction mixture was subjected to rotary evaporation, and purified by column chromatography to obtain 21 mg of a white foamy solid as a target compound 59 C$_{40}$H$_{52}$N$_2$O$_9$ (16.8% yield), which was structurally shown as follows:

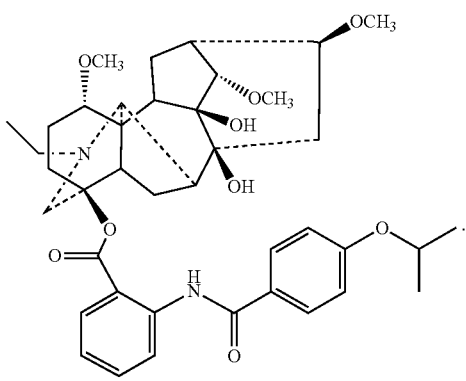

The target compound 59 was characterized as follows.

$^1$H-NMR (400 MHz, CDCl$_3$) δ: 11.92 (s, 1H), 8.87 (dd, J=8.6, 1.2 Hz, 1H), 8.12-7.85 (m, 3H), 7.54 (ddd, J=8.8, 7.4, 1.8 Hz, 1H), 7.04 (ddd, J=8.4, 7.4, 1.2 Hz, 1H), 6.98 (d, J=9.0 Hz, 2H), 4.65 (p, J=6.2 Hz, 1H), 3.61 (d, J=11.6 Hz, 1H), 3.57 (s, 1H), 3.44 (dd, J=4.8, 1.0 Hz, 1H), 3.41 (s, 3H), 3.31 (s, 3H), 3.30 (s, 3H), 3.20 (dd, J=10.4, 7.0 Hz, 1H), 3.02 (s, 1H), 2.74-2.65 (m, 2H), 2.58-2.50 (m, 3H), 2.46-2.36 (m, 3H), 2.34-2.24 (m, 2H), 2.18-2.09 (m, 3H), 2.06-1.94 (m, 2H), 1.91-1.81 (m, 1H), 1.62 (dd, J=15.2, 8.4 Hz, 1H), 1.38 (s, 3H), 1.36 (s, 3H), 1.13 (t, J=7.1 Hz, 3H)

$^{13}$C-NMR (100 MHz, CDCl$_3$) δ: 167.9, 165.5, 161.2, 142.3, 134.6, 131.3, 129.5, 129.5, 127.0, 122.3, 120.5, 116.2, 115.6, 115.6, 90.3, 84.7, 84.3, 83.0, 78.7, 75.8, 70.2, 61.6, 58.1, 56.7, 56.3, 55.7, 51.1, 49.9, 49.1, 48.5, 47.7, 45.0, 36.5, 31.9, 27.0, 26.4, 24.2, 22.1, 22.1, 13.7.

HR-ESI-MS m/z: [(M+H)$^+$, 705.3740].

Example 60 Preparation of Compound 60 with Lappaconitine and Butyl Chloroformate 100 mg of N-deacetyl lappaconitine was added in a 5 mL round-bottom flask, and dissolved with 2 mL of dry dichloromethane. 200 μL of dry pyridine was dropwise added under the protection of Ar, and 79 mg of butyl chloroformate was introduced under an ice bath. The reaction mixture was reacted at 20° C., where the reaction was monitored by thin-layer chromatography. After reacted for 2 h, the reaction mixture was subjected to rotary evaporation, and purified by column chromatography to obtain 107 mg of a white foamy solid as a target compound 60 C$_{35}$H$_{50}$N$_2$O$_9$ (90.3% yield), which was structurally shown as follows:

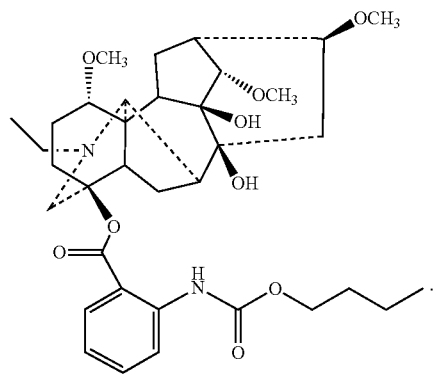

The target compound 60 was characterized as follows.

$^1$H-NMR (400 MHz, CDCl$_3$) δ: 10.46 (s, 1H), 8.41 (d, J=8.6 Hz, 1H), 7.90 (d, J=8.2 Hz, 1H), 7.52-7.43 (m, 1H), 6.96 (t, J=7.6 Hz, 1H), 4.16 (t, J=6.8 Hz, 2H), 3.60 (d, J=11.6 Hz, 1H), 3.55 (s, 1H), 3.43 (d, J=5.0 Hz, 1H), 3.40 (s, 3H), 3.31 (s, 3H), 3.29 (s, 3H), 3.18 (dd, J=10.4, 7.0 Hz, 1H), 3.00 (s, 1H), 2.74-2.63 (m, 2H), 2.74-2.63 (m, 4H), 2.43-2.34 (m, 3H), 2.28 (s, 1H), 2.15 (d, J=8.2 Hz, 1H), 2.09-1.95 (m, 4H), 1.84-1.74 (m, 1H), 1.67 (p, J=7.2 Hz, 2H), 1.60 (dd, J=15.2, 8.4 Hz, 1H), 1.42 (s, 2H), 1.11 (t, J=7.2 Hz, 3H), 0.95 (t, J=7.3 Hz, 3H).

$^{13}$C-NMR (100 MHz, CDCl$_3$) δ: 167.4, 153.9, 142.1, 134.4, 131.3, 121.4, 118.8, 115.6, 90.3, 84.6, 84.4, 83.0, 78.7, 75.8, 65.2, 61.7, 58.1, 56.7, 56.3, 55.6, 51.1, 50.0, 49.1, 48.7, 47.7, 45.0, 36.4, 32.0, 30.3, 26.9, 26.4, 24.2, 19.2, 13.9, 13.7.

HR-ESI-MS m/z: [(M+H)$^+$, 643.3640].

The beneficial effects of the present disclosure are demonstrated through the following experimental examples.

Experimental Example 1 Analgesic Activity and Toxicity Test of Lappaconitine Derivatives 1. Experimental Method Experimental Animals The experimental animals were Kunming mice (male:female=1:1), weighed 22±2 g, which were provided by Chengdu dossy experimental animals Co., ltd., China. The mice were kept in the animal room of the School of Life Science and Engineering, Southwest Jiaotong University, where the animal room was set at a temperature of 23±2° C., a humidity of 55±5% and a photoperiod of 16:8 h (L:D). Before the experiment, the mice were freely fed for 2-3 days with water and feed to adapt to the new environment. Then, the mice were treated by water fasting for 12 h. 10 animals were allocated to each group to ensure that there are at least 6 sets of valid data in each group. The animal experiments were carried out in strict accordance with the national regulations on the management of experimental animals.

Test Samples

The compounds prepared in the examples provided herein and the positive control lappaconitine were all dissolved with 0.1 mol/L HCl according to the amount of the substance ratio of 1:1, and then diluted with physiological saline to a concentration to be determined. The samples to be tested were the compounds prepared the examples provided herein; the positive control was lappaconitine; and the blank control was physiological saline containing 0.1 mol/L HCl.

The animals in the control groups were subjected to the same treatment as those in the experimental group except that the samples to be test were replaced with physiological saline.

Determination of Analgesic Activity Through an Acetic Acid-Induced Writhing Method 10 mice were randomly selected, male:female=1:1, were placed in independent cages. Each mouse was injected subcutaneously with the sample solution mentioned above at a dose of 0.1 mL/10 g body weight. After 15 min, a 0.7% acetic acid solution was intraperitoneally injected. The number of writhing reactions in each mouse within 15 minutes was recorded. The group that the mice were injected with physiological saline subcutaneously was the blank group; the group that the mice were injected with the sample to be tested was the experimental group; and the group that the mice were injected with lappaconitine was the positive group. The analgesic activity was represented by a percentage of the reduced number of writhing compared to the blank group (writhing inhibition rate), which were specifically as follows: writhing inhibition rate (analgesic activity)=(average number of writhing times in the blank group-average number of writhing times in the experimental group)/average number of writhing times in the blank group×100%.

Median Effective Dose ($ED_{50}$) Determination

The sample to be tested was dissolved with 0.1 mol/L HCl according to the amount of the substance ratio of 1:1, and diluted with physiological saline according to the proportional series to obtain at least 5 groups with different dose concentrations. The writhing inhibition rate of each dose group was tested according to the acetic acid-induced writhing method mentioned above. The obtained does-writhing inhibition data was entered into the statistical product and service solutions (SPSS) software (version 17.2), and the $ED_{50}$ of the sample to be tested was calculated through the Probit regression method.

Median Lethal Dose ($LD_{50}$) Determination

The sample to be tested was dissolved with 0.1 mol/L HCl according to the amount of the substance ratio of 1:1, and diluted with physiological saline according to the required concentration. 10 mice in each group were randomly selected, half of which are male and half of which were female, and were placed in independent cages. Each mouse was injected subcutaneously with different sample solutions to be tested according to a dose of 0.1 mL/10 g body weight. In the preliminary toxicity experiment, the measured concentration was 100 mg/kg, and then based on the survival rate of the experimental animals in the preliminary experiment, the sample to be tested was set to at least 5 groups with different concentration dose according to the proportional series. The survival rate of mice within 24 h was recorded. The obtained dose-survival rate data was input into the SPSS software (version 17.2), and the $LD_{50}$ of the sample was calculated according to the Probit regression method.

2. Experimental Results

TABLE 1

Analgesic activity of each compound

| Compound No. | Dosing concentration (mg/kg) | Analgesia rate ± SEM (%) |
|---|---|---|
| Lappaconitine | 10 | —[a] |
| | 3.5 | 56.57 ± 6.57** |
| Blank control | —[b] | 0.00 |
| 1 | 10 | 84.26 ± 3.05** |
| 2 | 10 | 71.23 ± 3.80** |
| 3 | 10 | 71.20 ± 2.72** |
| 4 | 10 | 71.14 ± 5.97** |
| 5 | 10 | 62.10 ± 5.02** |
| 6 | 10 | 60.27 ± 5.94** |
| 7 | 10 | 50.23 ± 6.85** |
| 8 | 10 | 49.25 ± 5.00** |
| 9 | 10 | 43.84 ± 4.50** |
| 10 | 10 | 42.47 ± 2.56** |

TABLE 1-continued

Analgesic activity of each compound

| Compound No. | Dosing concentration (mg/kg) | Analgesia rate ± SEM (%) |
|---|---|---|
| 11 | 10 | 42.39 ± 5.98** |
| 12 | 10 | 41.85 ± 3.80** |
| 13 | 3.5 | 37.06 ± 15.74 |
| 14 | 10 | 28.36 ± 4.98* |
| 15 | 3.5 | 27.66 ± 12.87 |
| 16 | 10 | 24.38 ± 8.46* |
| 17 | 10 | 22.75 ± 7.58* |
| 18 | 10 | 20.00 ± 6.67 |
| 19 | 10 | 19.44 ± 5.00 |
| 20 | 3.5 | 16.75 ± 6.09 |
| 21 | 10 | 16.42 ± 11.50 |
| 22 | 10 | 16.11 ± 10.56 |
| 23 | 3.5 | 14.72 ± 13.20 |
| 24 | 10 | 13.27 ± 9.00 |
| 25 | 10 | 11.67 ± 7.78 |
| 26 | 10 | 11.37 ± 7.58 |
| 27 | 10 | 4.02 ± 9.50 |
| 28 | 10 | 1.03 ± 10.26 |
| 29 | 10 | 1.03 ± 5.37 |
| 30 | 10 | 63.87 ± 5.09** |
| 31 | 10 | 62.83 ± 5.41** |
| 32 | 10 | 62.80 ± 5.77** |
| 33 | 10 | 56.94 ± 3.82** |
| 34 | 10 | 54.19 ± 6.15** |
| 35 | 10 | 48.39 ± 6.08** |
| 36 | 10 | 36.36 ± 9.54 |
| 37 | 10 | 34.47 ± 4.68** |
| 38 | 10 | 33.98 ± 8.92** |
| 39 | 5 | 33.50 ± 7.27* |
| 40 | 10 | 31.58 ± 12.59 |
| 41 | 10 | 31.53 ± 8.19* |
| 42 | 10 | 31.30 ± 10.69* |
| 43 | 10 | 31.10 ± 8.56 |
| 44 | 10 | 28.23 ± 7.88 |
| 45 | 10 | 27.75 ± 5.83 |
| 46 | 10 | 26.70 ± 7.95 |
| 47 | 10 | 24.88 ± 9.70 |
| 48 | 10 | 21.84 ± 12.64 |
| 49 | 10 | 21.00 ± 6.58 |
| 50 | 10 | 16.40 ± 8.07 |
| 51 | 10 | 12.83 ± 13.40 |
| 52 | 10 | 10.70 ± 12.06 |
| 53 | 10 | 9.95 ± 11.47 |
| 54 | 10 | 8.42 ± 12.69 |
| 55 | 10 | 3.40 ± 15.28 |
| 56 | 10 | 0.00 ± 7.45 |
| 57 | 10 | 0.00 ± 13.44 |
| 58 | 10 | 0.00 ± 10.95 |
| 59 | 10 | 61.08 ± 5.52** |
| 60 | 10 | 69.23 ± 3.42** |

[a]Unable to test due to lethality in mice;
[b]The blank control was physiological saline containing 0.1 mol/L HCl;
*P < 0.05,
**P < 0.01.

TABLE 2

$ED_{50}$ and $LD_{50}$ of the preferred compounds

| Compound No. | $ED_{50}$ (mg/kg) | $LD_{50}$ (mg/kg) |
|---|---|---|
| 1 | 6.1 | >600 |
| 2 | 5.5 | 300 |
| 3 | 4.7 | >400 |
| 4 | 1.2 | 10 |
| 5 | 6.1 | 300 |
| 30 | 7.5 | 275.5 |
| 31 | 6.6 | 314.7 |

TABLE 2-continued

ED$_{50}$ and LD$_{50}$ of the preferred compounds

| Compound No. | ED$_{50}$ (mg/kg) | LD$_{50}$ (mg/kg) |
|---|---|---|
| 32 | 4.4 | 296.4 |
| 59 | 8.1 | 195.8 |
| 60 | 4.2 | 21.2 |
| Lappaconitine | 3.5 | 11.7 |

Table 1 shows that the analgesic activity of most of compounds prepared in the examples provided herein is comparable to or higher than that of lappaconitine. The following compounds have significant activity: compounds 1, 2 and 3 in sulfonamide series derivatives; compounds 4 and 60 in carbamate series derivatives; and compounds 5, 30, 31, 32 and 59 in amide series derivatives. It should be noted that at a dosing concentration of 10 mg/kg, the lappaconitine as the positive control drug and some compounds would cause more than half of the experimental animal death from poisoning, and thus the concentration of these compounds in the analgesic activity test were set to 3.5 mg/kg.

The high-efficiency and low-toxicity compound with a writhing inhibition rate no less than 60% was further tested for ED$_{50}$ and LD$_{50}$. Table 2 shows that the ED$_{50}$ of compounds 1, 2, 3, 5, 30, 31, 32 and 59 has the same order of magnitude as that of lappaconitine, which is the positive control drug. Those eight compounds have an analgesic activity comparable to that of the lappaconitine, and the toxicity of those compounds is far lower than that of lappaconitine. In addition, the activity of compound 4 was doubled compared with lappaconitine, but the toxicity of the compound 4 did not increase significantly; the activity of compound 60 was equivalent to lappaconitine, but the toxicity was reduced by half.

The above experimental results demonstrate that the lappaconitine derivatives provided herein have good analgesic activity and less biological toxicity, and are suitable for preparing low-toxic analgesics.

What is claimed is:

1. A compound of formula (III), or a stereoisomer, a deuterated compound or a pharmaceutically acceptable salt thereof

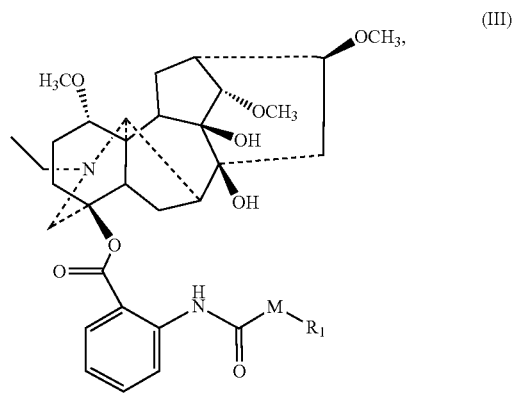

(III)

wherein M is O or NH;

R$_1$ is C$_{1-4}$ alkyl, C$_{1-4}$ alkoxy, C$_{2-4}$ alkenyl, C$_{2-4}$ alkynyl, 5-6 membered aryl or 5-6 membered heteroaryl.

2. A compound of formula (V), or a stereoisomer, a deuterated compound or a pharmaceutically acceptable salt thereof

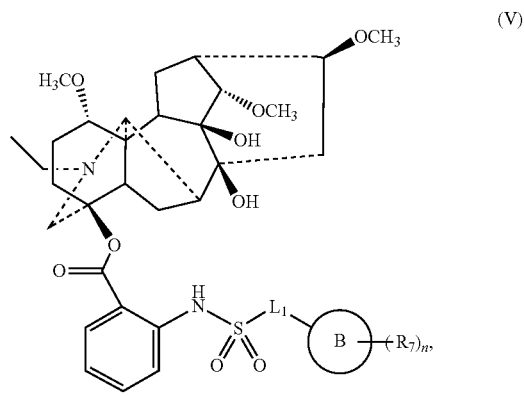

(V)

wherein L$_1$ is absent or C$_{1-2}$ alkylene;

n is an integer selected from 0-3;

R$_7$ is each independently selected from the group consisting of hydrogen, halogenated and unsubstituted C$_{2-4}$ alkyl, halogenated and unsubstituted C$_{1-4}$ alkoxy, C$_{2-4}$ alkenyl, C$_{2-4}$ alkynyl, NR$_3$R$_4$, COOR$_5$, SO$_2$R$_6$, halogen, cyano, nitro and phenyl; wherein R$_3$, R$_4$, R$_5$ and R$_6$ are each independently selected from the group consisting of hydrogen and C$_{1-4}$ alkyl; and ring B is 5-6 membered aryl, 5-6 membered heteroaryl, 3-6 membered saturated cycloalkyl, 3-6 membered saturated heterocyclic group, heterofused ring group, bicycloalkyl group or heterobicyclic group.

3. A compound, or a stereoisomer, a deuterated compound or a pharmaceutically acceptable salt thereof, the compound being selected from the group consisting of:

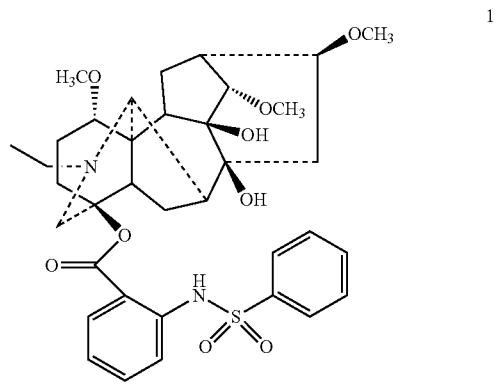

1

-continued
2
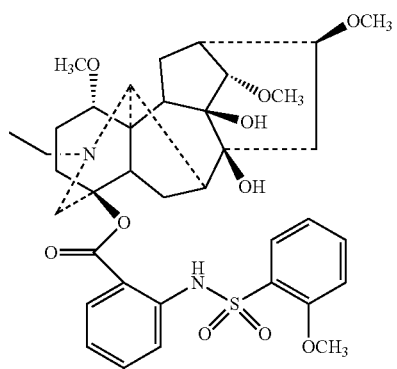
3
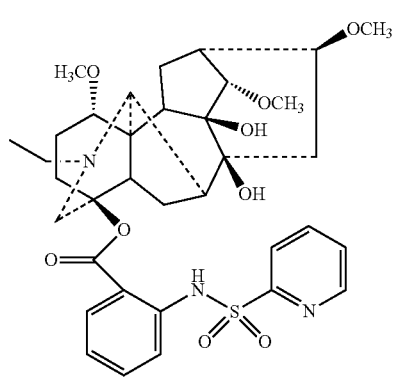
4
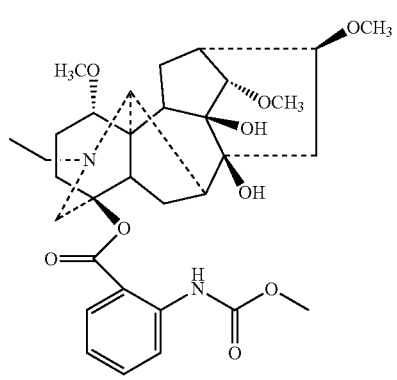
5
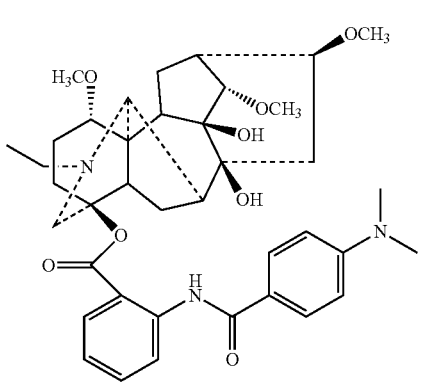
-continued
6
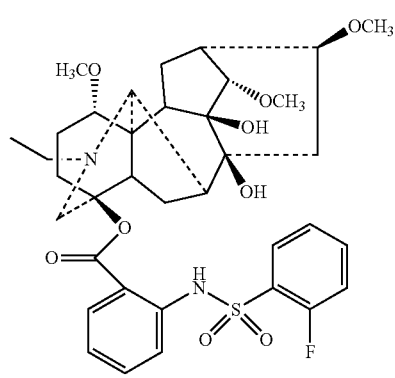
7
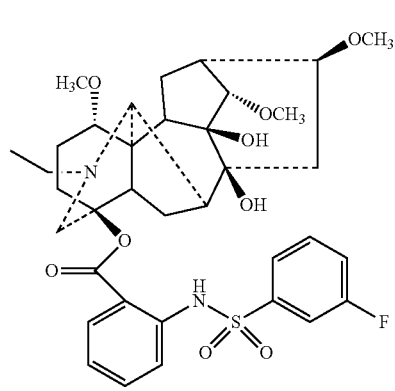
8
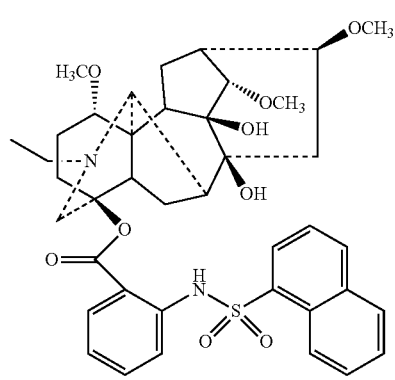
9
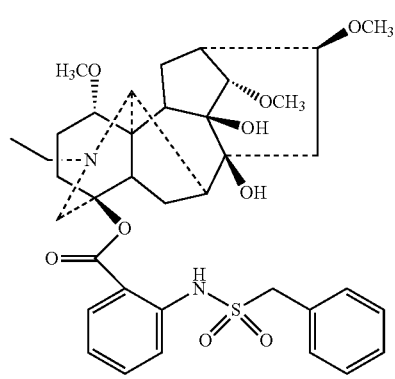

10
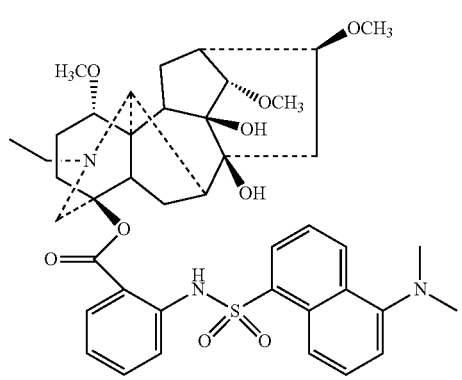
11
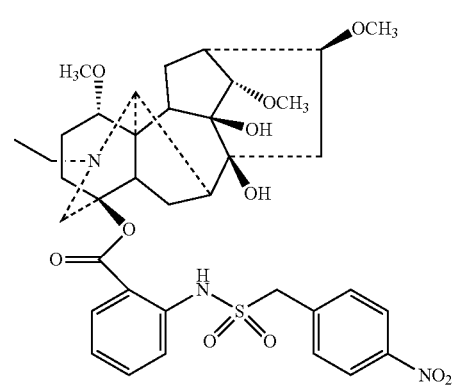
12
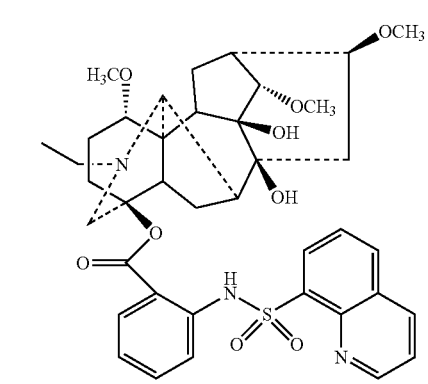
13
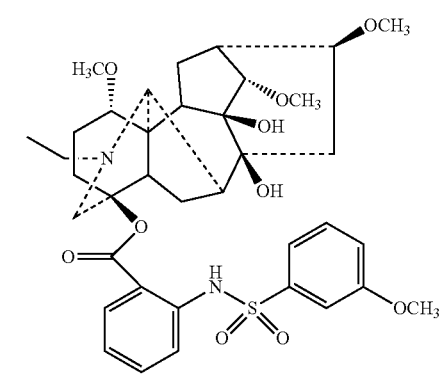
14
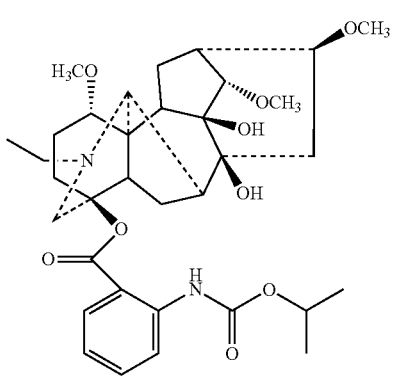
18
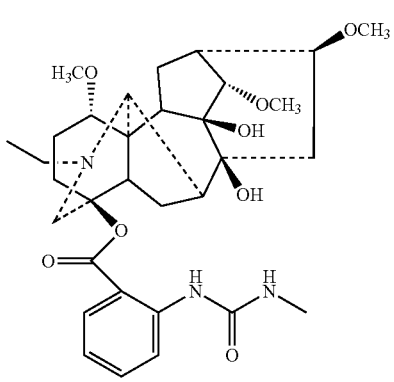
19
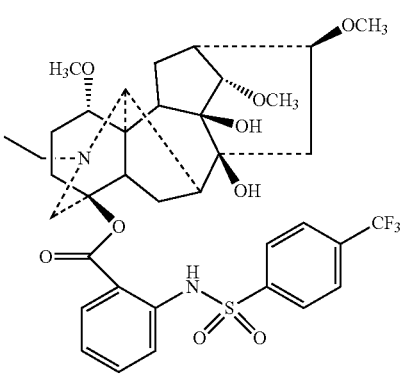
20
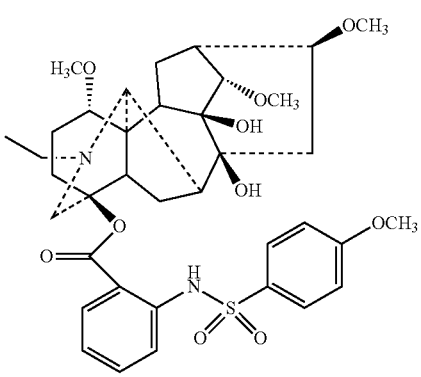

21
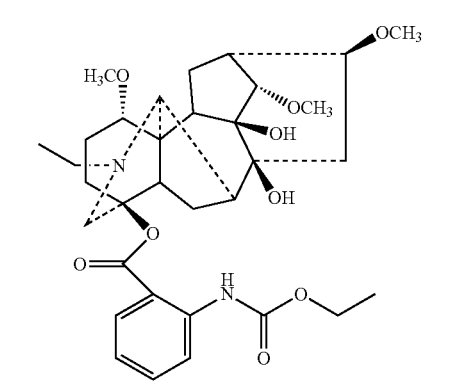
22
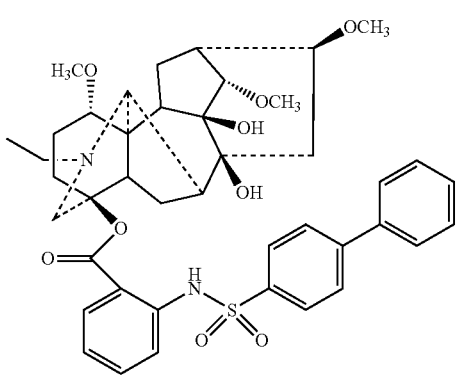
23
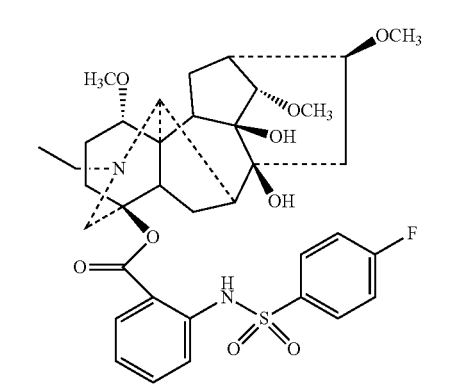
24
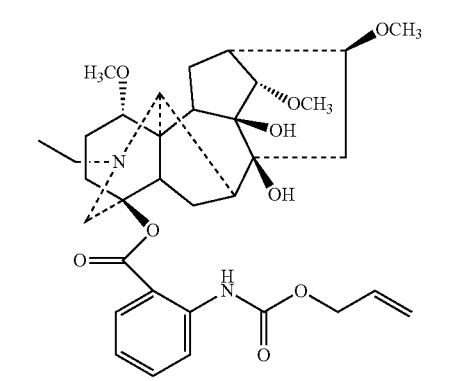
25
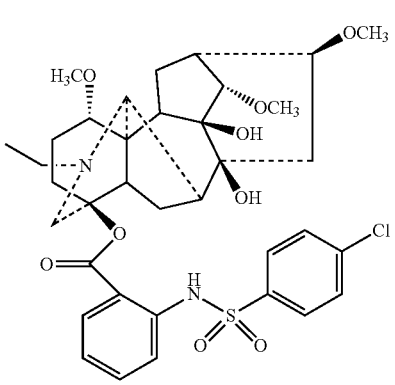
26
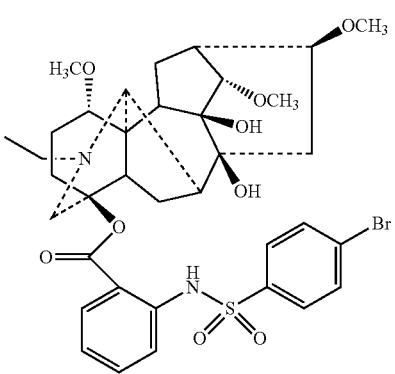
28
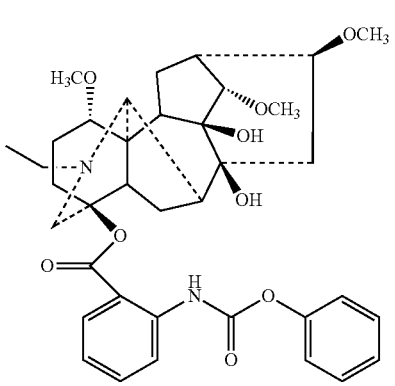
29
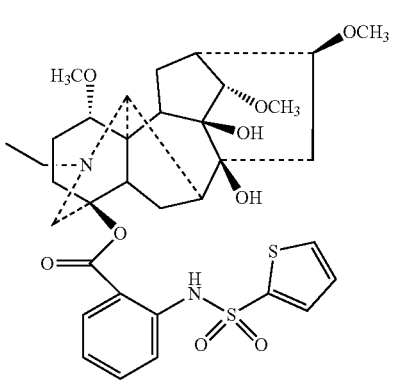

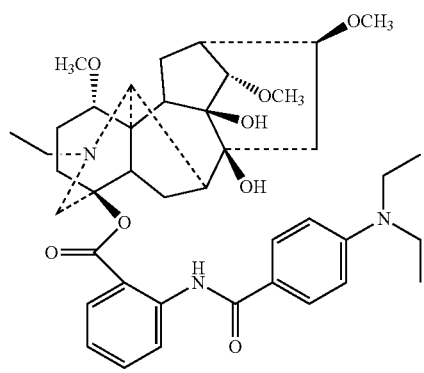
30
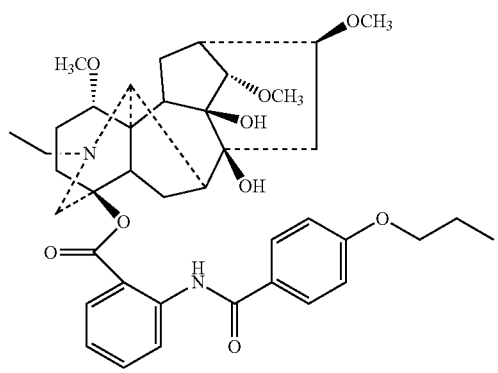
35
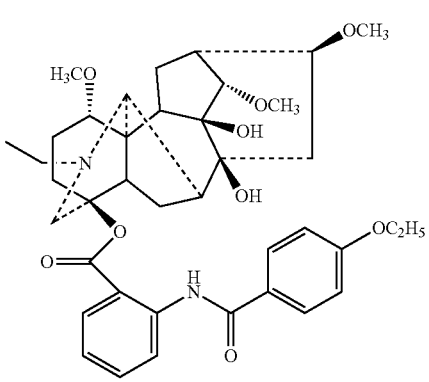
31
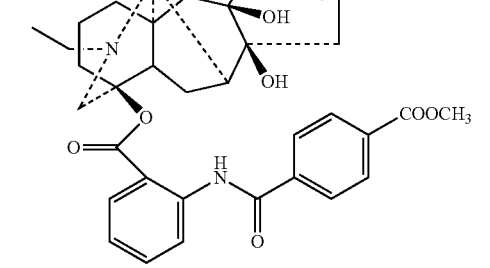
36
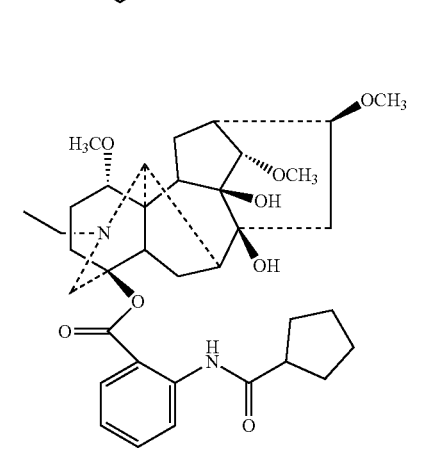
33
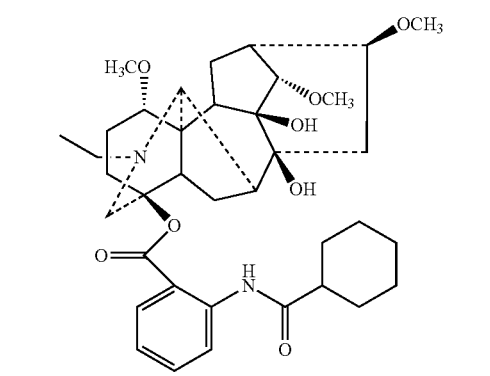
37
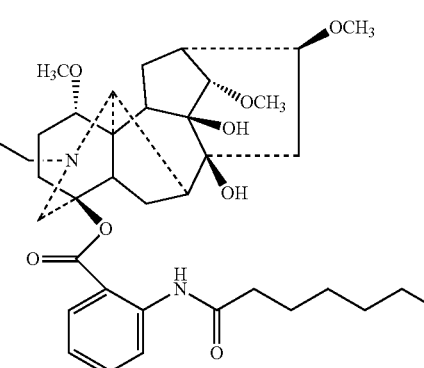
34
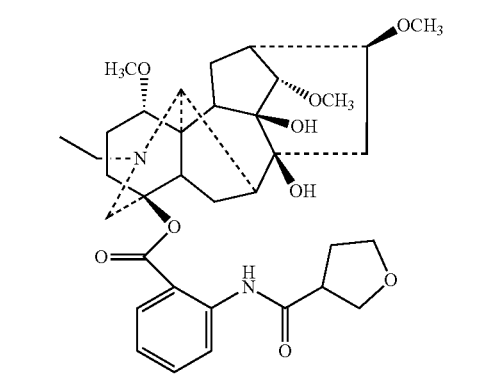
38

39
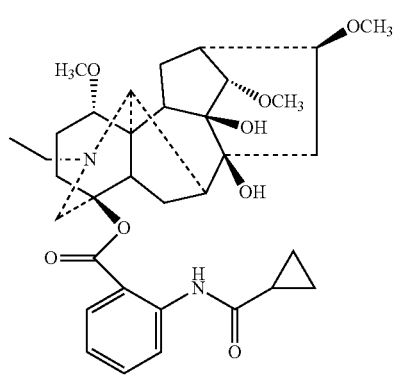
40
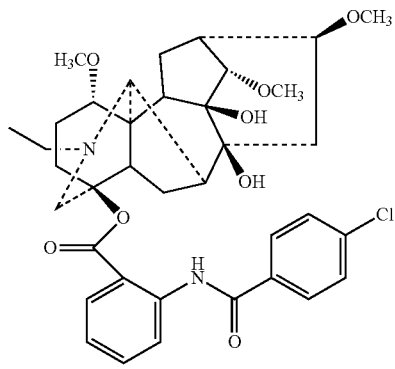
41
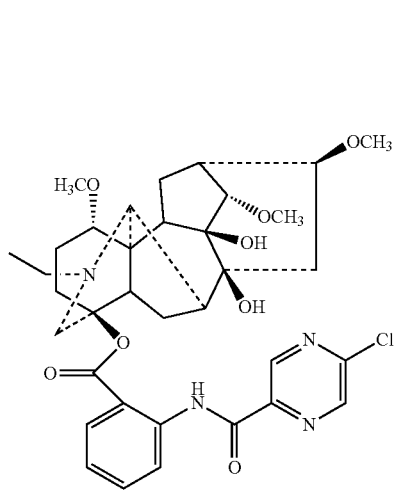
42
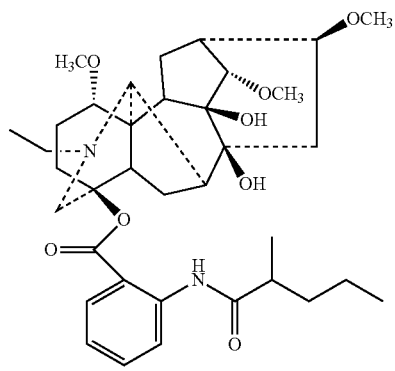
43
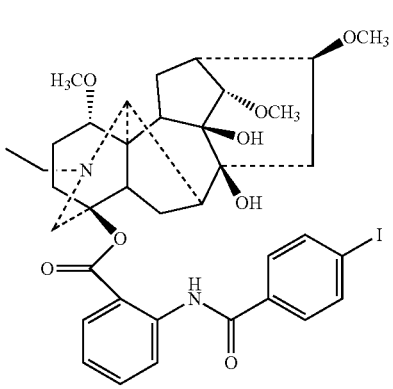
44
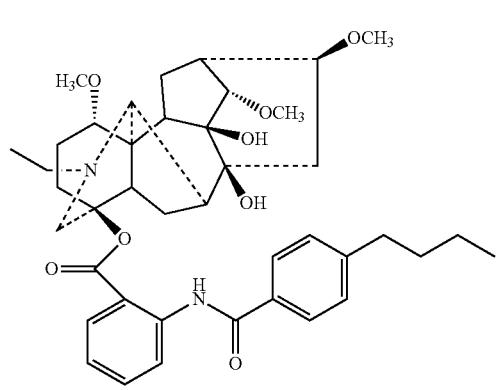
45
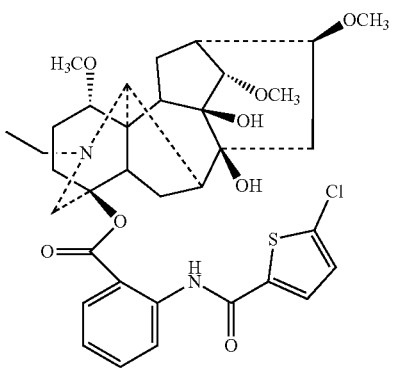
46
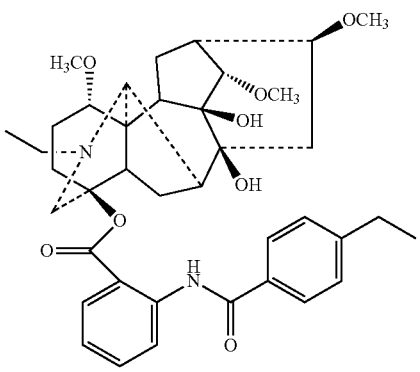

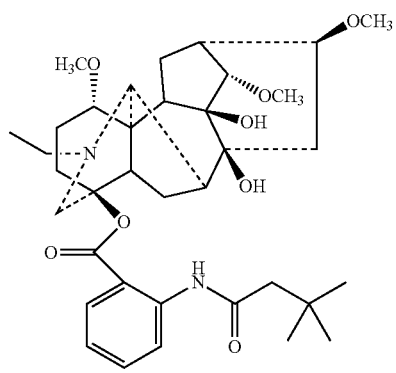
47
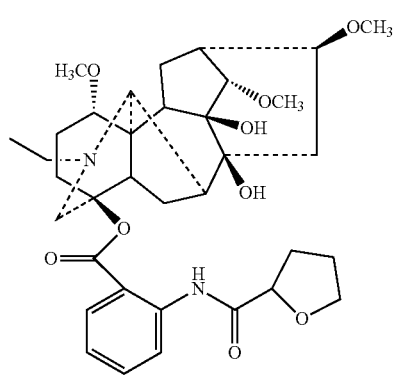
48
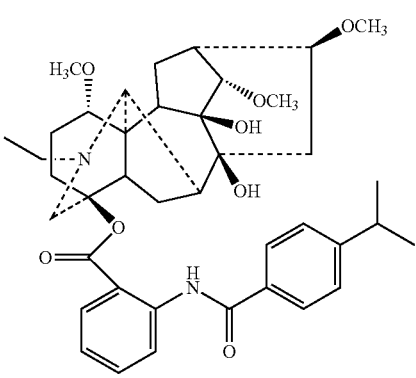
49
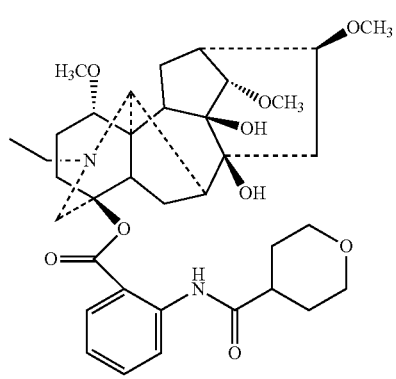
50
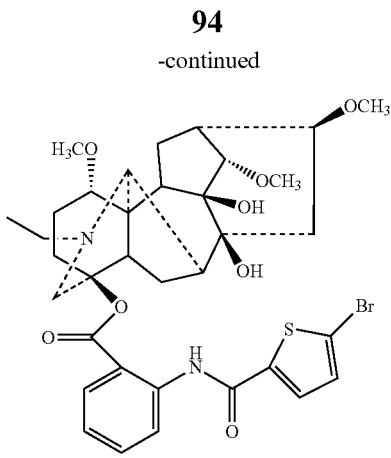
51
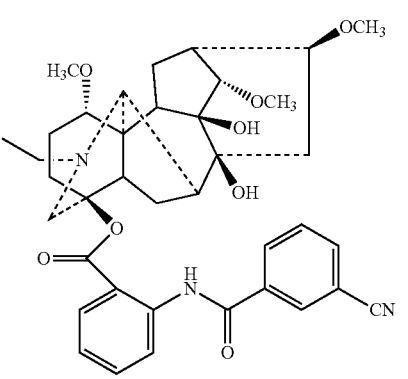
52
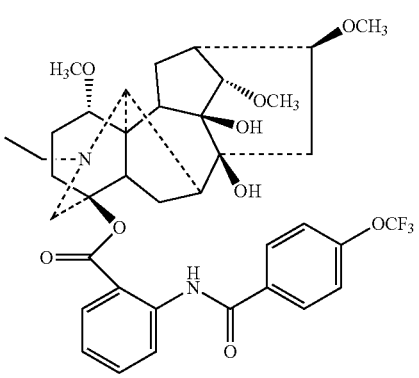
53
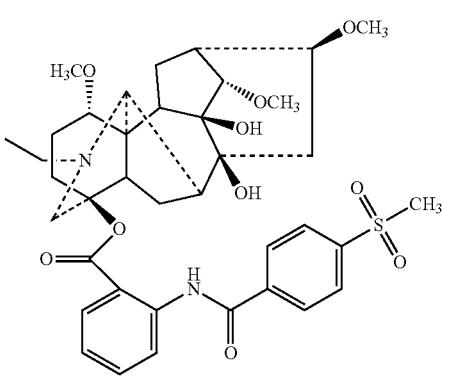
54

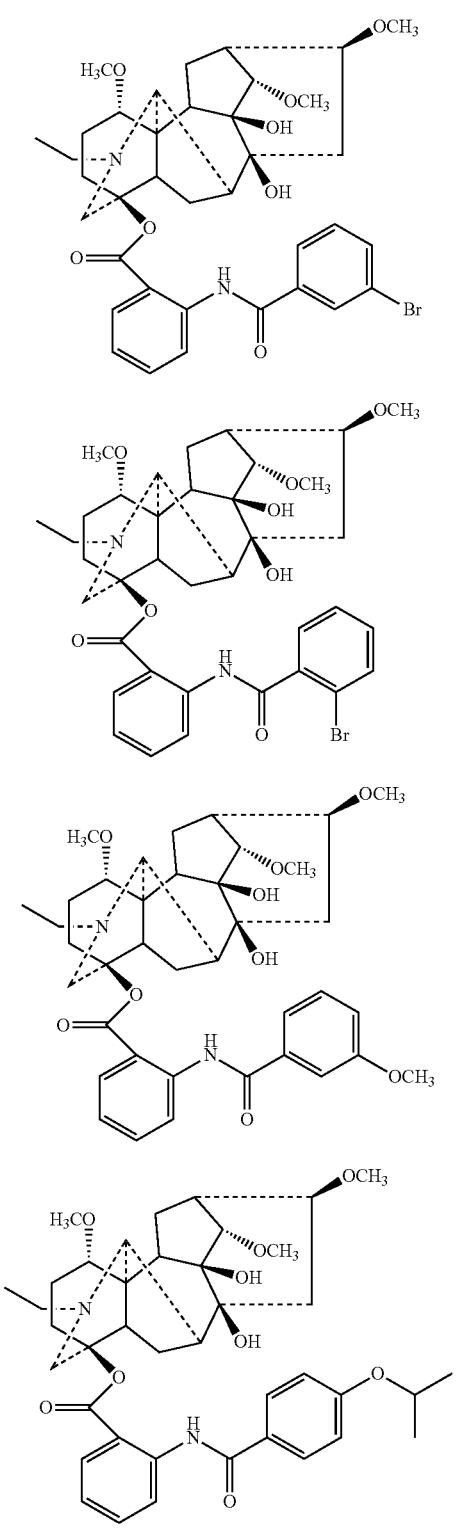

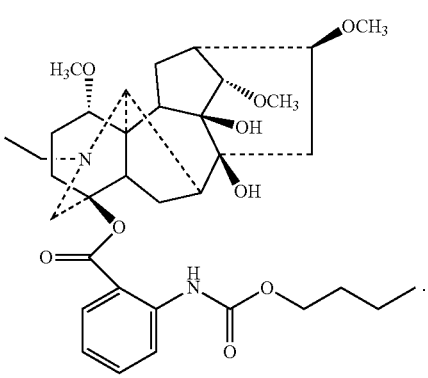

4. An analgesic composition, comprising:
the compound of claim 1, or a stereoisomer, a deuterated compound or a pharmaceutically acceptable salt thereof; and
a pharmaceutically acceptable excipient.

5. A method for relieving pain in a subject in need thereof, comprising:
administering to the subject a pharmaceutically effective amount of the compound of claim 1, or a stereoisomer, a deuterated compound or a pharmaceutically acceptable salt thereof.

6. The method of claim 5, wherein a median lethal dose of the compound is higher than a median lethal dose of lappaconitine.

7. An analgesic composition, comprising:
the compound of claim 2, or a stereoisomer, a deuterated compound or a pharmaceutically acceptable salt thereof; and
a pharmaceutically acceptable excipient.

8. A method for relieving pain in a subject in need thereof, comprising:
administering to the subject a pharmaceutically effective amount of the compound of claim 2, or a stereoisomer, a deuterated compound or a pharmaceutically acceptable salt thereof.

9. An analgesic composition, comprising:
the compound of claim 3, or a stereoisomer, a deuterated compound or a pharmaceutically acceptable salt thereof; and
a pharmaceutically acceptable excipient.

10. A method for relieving pain in a subject in need thereof, comprising:
administering to the subject a pharmaceutically effective amount of the compound of claim 3, or a stereoisomer, a deuterated compound or a pharmaceutically acceptable salt thereof.

* * * * *